United States Patent [19]
Goldin et al.

[11] Patent Number: 5,403,861
[45] Date of Patent: Apr. 4, 1995

[54] SUBSTITUTED GUANIDINES AND DERIVATIVES THEREOF AS MODULATORS OF NEUROTRANSMITTER RELEASE AND NOVEL METHODOLOGY FOR IDENTIFYING NEUROTRANSMITTER RELEASE BLOCKERS

[75] Inventors: Stanley M. Goldin, Lexington; Subbarao Katragadda, Belmont; Lain-Yen Hu, Bedford; N. Laxma Reddy, Malden; James B. Fischer, Cambridge; Andrew G. Knapp, Salem; Lee D. Margolin, Belmont, all of Mass.

[73] Assignee: Cambridge NeuroScience, Inc., Cambridge, Mass.

[21] Appl. No.: 833,421

[22] Filed: Feb. 10, 1992

Related U.S. Application Data

[63] Continuation-in-part of Ser. No. 652,104, Feb. 8, 1991, abandoned.

[51] Int. Cl.$^6$ .................. A61K 31/155; A61K 31/17; A61K 31/16; A61K 31/165
[52] U.S. Cl. ..................................... 514/634; 514/150; 514/519; 514/506; 514/588; 514/616; 514/623
[58] Field of Search ............ 564/237, 238, 240; 514/482, 414, 415, 367, 308, 310, 313, 352, 353, 339, 340, 341, 342, 275, 256, 255, 477, 444, 447, 426, 376, 372, 377, 380, 397, 398, 438, 365, 374, 378, 399, 634, 519, 506, 150, 588, 616, 623

[56] References Cited

U.S. PATENT DOCUMENTS

| | | | |
|---|---|---|---|
| 1,422,506 | 7/1922 | Weiss | 564/238 |
| 1,597,233 | 8/1926 | Heuser | 564/238 |
| 1,642,180 | 9/1927 | Scott | 564/238 |
| 1,672,431 | 6/1928 | Schotte | 564/238 |
| 1,677,235 | 7/1928 | Heuser | 564/238 |
| 1,756,315 | 4/1930 | Ter Horst | 564/238 |
| 1,795,738 | 3/1931 | Schotte | 564/238 |
| 1,850,682 | 3/1932 | Meis | 564/238 |
| 1,915,922 | 6/1933 | Christmann et al. | 564/238 |
| 2,145,214 | 1/1939 | Jayne | 167/37 |
| 2,254,009 | 8/1941 | Hechenbleikner | 260/564 |
| 2,274,476 | 2/1942 | Hechenbleikner | 167/30 |
| 2,289,541 | 7/1942 | Ericks et al. | 167/22 |
| 2,362,915 | 11/1944 | MacGregor | 3/74 |
| 2,633,474 | 3/1953 | Beaver | 260/565 |
| 2,704,710 | 3/1955 | Sprung | 95/2 |
| 3,117,994 | 1/1964 | McKay et al. | 260/564 |
| 3,140,231 | 7/1964 | Luskin et al. | 167/65 |
| 3,159,676 | 12/1964 | Spickett et al. | 260/564 |
| 3,228,975 | 1/1966 | Abraham et al. | 260/501 |
| 3,248,426 | 4/1966 | Dvornik | 260/564 |
| 3,252,861 | 5/1966 | Mull | 167/65 |
| 3,270,054 | 8/1966 | Gagneux et al. | 260/564 |
| 3,283,003 | 11/1966 | Jack et al. | 260/564 |

(List continued on next page.)

FOREIGN PATENT DOCUMENTS

WO88/00583 1/1988 WIPO.

(List continued on next page.)

OTHER PUBLICATIONS

Bean, B., Multiple Types of Calcium Channels in Heart Muscle and Neurons, *Ann. N.Y. Acad. Sci.* 560:334–345 (1989).

(List continued on next page.)

Primary Examiner—Richard L. Raymond
Assistant Examiner—Mary Cebulak
Attorney, Agent, or Firm—David G. Conlin; Peter F. Corless

[57] ABSTRACT

Modulators of neurotransmitter release including substituted guanidines, N''-aminoguanidines, and N,N'N'',N'''-tetrasubstituted hydrazinedicarboximidamides, and pharmaceutical compositions thereof are disclosed. Also disclosed are methods involving the use of such neurotransmitter release modulators for the treatment or prevention of pathophysiologic conditions characterized by the release of excessive or inappropriate levels of neurotransmitters. Also disclosed are screening assays for compounds which selectively inhibit glutamate release. Also disclosed are methods of blocking voltage sensitive sodium and calcium channels in mammalian nerve cells.

37 Claims, 15 Drawing Sheets

U.S. PATENT DOCUMENTS

| | | | |
|---|---|---|---|
| 3,301,755 | 1/1967 | Mull | 167/65 |
| 3,320,229 | 5/1967 | Szabo et al. | 260/96.5 |
| 3,391,189 | 7/1968 | Mull | 260/564 |
| 3,409,669 | 11/1968 | Dyke | 260/564 |
| 3,479,437 | 11/1969 | Szabo et al. | 424/304 |
| 3,547,951 | 12/1970 | Hardie et al. | 260/340.9 |
| 3,639,477 | 2/1972 | L'Italien | 260/564 |
| 3,681,459 | 8/1972 | Hughes et al. | 260/565 |
| 3,769,427 | 10/1973 | Hughes et al. | 424/326 |
| 3,803,324 | 4/1974 | Panneman | 260/564 |
| 3,908,013 | 9/1975 | Hughes et al. | 424/258 |
| 3,949,089 | 4/1976 | Maxwell et al. | 424/326 |
| 3,968,243 | 7/1976 | Maxwell et al. | 424/326 |
| 3,976,643 | 8/1976 | Diamond et al. | 260/247.5 |
| 3,976,787 | 8/1976 | Hughes et al. | 424/326 |
| 4,007,181 | 2/1977 | DuCharme et al. | 260/247.5 |
| 4,014,934 | 3/1977 | Hughes et al. | 260/565 |
| 4,051,256 | 9/1977 | Swallow | 424/304 |
| 4,052,455 | 10/1977 | Matier et al. | 260/562 |
| 4,060,640 | 11/1977 | Kodama et al. | 424/326 |
| 4,109,014 | 8/1978 | Liu et al. | 424/326 |
| 4,130,663 | 12/1978 | Matier et al. | 424/326 |
| 4,161,541 | 7/1979 | Rasmussen | 424/326 |
| 4,169,154 | 9/1979 | Cohen et al. | 424/322 |
| 4,471,137 | 9/1984 | Barton et al. | 564/240 |
| 4,709,094 | 11/1987 | Weber et al. | 564/238 |
| 4,742,054 | 5/1988 | Naftchi | 514/215 |
| 4,803,324 | 4/1974 | Winter et al. | 424/326 |
| 4,837,218 | 6/1989 | Olney | 514/646 |
| 4,891,185 | 1/1990 | Goldin | 422/69 |
| 4,898,978 | 2/1990 | Bergfeld et al. | 564/231 |
| 4,906,779 | 3/1990 | Weber et al. | 564/238 |
| 5,093,525 | 3/1992 | Weber et al. | 564/238 |
| 5,190,976 | 3/1993 | Weber et al. | 514/634 |
| 5,262,568 | 11/1993 | Weber et al. | 564/238 |

FOREIGN PATENT DOCUMENTS

| | | |
|---|---|---|
| 0001500 | 4/1979 | European Pat. Off. . |
| 0035374 | 9/1981 | European Pat. Off. . |
| 0179642 | 4/1986 | European Pat. Off. . |
| 514248 | 11/1930 | Germany . |
| 2029707 | 12/1970 | Germany . |
| 2133056 | 1/1973 | Germany . |
| 2452691 | 5/1975 | Germany . |
| 223410 | 10/1924 | United Kingdom . |
| 258203 | 9/1926 | United Kingdom . |
| 478525 | 1/1938 | United Kingdom . |
| WO87/04433 | 7/1987 | WIPO . |
| WO90/14067 | 11/1990 | WIPO . |
| WO91/12797 | 9/1991 | WIPO . |
| WO91/18868 | 12/1991 | WIPO . |
| WO92/14697 | 9/1992 | WIPO . |

OTHER PUBLICATIONS

Bean, B., Classes of Calcium Channels in Vertebrate Cells, *Annu. Rev. Physiol.* 51:367–384 (1989).

Bent et al., Antiviral aminoguanidines compositions, *Pesticides* 74:63479m (1971).

Bhargava et al., Synthesis of some new N,N'-di-(substituted 2-benzothiazolyl) guanidines as antituberculars and CNS depressants, *Chemical Abstracts* 86:189787b (1977).

Campbell et al., Sigma Receptors Regulate Contractions of the Guinea Pig Ileum Logitudinal Muscle/Myenteric Plexus Preparation Elicited By Both . . . , *Journal of Neuroscience* 9(10):3380–3391 (1989).

Chernevskaya et al., NMDA receptor agonists selectively block N-type calcium channels in hippocampal neurons, *Nature* 349:418–420 (1991).

Choi, D., Cerebral Hypoxia: Some New Approaches and Unanswered Questions, *Journal of Neuroscience* 10(8):2493–2501 (1990).

Choi, D., Methods for Antagonizing Glutamate Neurotoxicity, *Cerebrovascular and Brain Metabolism Reviews* 2:105–147 (1990).

Choi, D., Glutamate Neurotoxicity and Diseases of the Nervous System, *Neuron* 1:623–634 (1988).

Dreyer et al., HIV-1 Coat Protein Neurotoxicity Prevented by Calcium Channel Antagonists, *Science* 248:364–367 (1990).

Durant et al., Biologically Active Guanidines and Related Compounds. II. Some Antiinflamatory Aminoguanidines, *J. Med. Chem.* 9:22–27 (1966).

Durant et al., The Histamine H2 Receptor Agonist Impromidine: Synthesis and Structure-Activity Considerations, *J. Med. Chem.* 28:1414–1422 (1985).

Fox et al., Kinetic and Pharmacological Properties Distinguishing Three Types of Calcium Currents in Chick Sensory Neurones, *J. Physiol.* 394:149–172 (1987).

Fox et al., Single-Channel Recordings of Three Types of Calcium Channels in Chick Sensory Neurones, *J. Physiol.* 394:173–200 (1987).

Geluk et al., Synthesis and Antiviral Properties of (List continued on next page.)

OTHER PUBLICATIONS

1-Adamantylguanidine. A Modified Method for Preparing t-Alkylguanidines, *J. Med. Chem.* 12:712–715 (1969).

Ginsburg et al., Heterolytic reactions of polyfluorinated azoalkanes, *Chem. Abstr.* 4518 (1962).

Ginsburg et al., Polyfluoro Azo Compounds IV. Properties of Hexafluorohydrazomethane, *Zhurnal Organicheskoi Khimii* 7(11):2267–2270 (1971), Unverified Translation.

Godfraind et al., Increasing complexity revealed in regulation of Ca2+ antagonist receptor, *Trends in Pharmacological Sciences* 10(8):297–301 (1989).

Goldin, Stanley et al., Synthetic Neuroprotective Glutamate Release Blockers, Small Business Innovation Research Program Phase I Grant Application, funded Dec. 1991.

Heinisch, L., Darstellung neuer substituierter 1,2,4-Triazin-6-carbonsauren und 1,2,4-Triazin-6-yl-alkancarbonsauren, *Journal f. prakt. Chemie* 329:290–300 (1987).

Huisgen et al., Zur Bildung von 1.4-Dihydro-tetrazinen aus Nitriliminen; 1.4-Diphenyl-1-dihydro-1.2.4.5-tetrazin und isomere Verbindungen, *Chem. Ber.* 98:1476–1486 (1965).

Huisgen et al., 1,3-Dipolar cycloadditions. XVI. Formation of 1,4-dihydro-tetrazines from nitrilimines; 1,4-diphenyl-1,4-dihydro-1,2,4,5-tetrazine . . . , *Chemical Abstracts* 63:2975 (1965).

Kaneko et al., Anti-ischemic Effect of the Novel Anti-ischemic Agent 2-(4-(p-Fluorobenzoyl) piperidin-1-yl)-2'-acetonaphthone . . . , *Arzneim. Forsch./Drug Res.* 39(1):445–450 (1989).

Katragadda et al., Multiple Kinetically Distinguishable Components of 3H-Dopamine Release From Nerve Terminals, *Soc. for Neurosci. Abstr.* 16:64 (1990).

Kreutzberger et al., 2,2'-Azoimidazolbildung durch cyclische Acyloine, *Arch. Pharmz, Ber. Duet. Pharm. Ges.* 305:400–405 (1972).

Keana et al., Synthesis and characterization of a series of diarylguadines that are noncompetitive N-methyl-D-aspartate receptor antagonists . . . , *Proc. Natl. Acad. Sci. USA* 86:5631–5635 (1989).

Kroeger et al., 1,2,4-Triazoles. VI. Condensation of methyl-substituted aminoguanidines with aliphatic carborylic acids, *Chemical Abstracts* 60:9265 (1964).

Kroger et al., Die Kondensation methylsubstituierter Aminoguanidine mit aliphatischen Carbonsauren, *Ber.* 97:396–404 (1964).

Langlais et al., Protective Effects of the Glutamate Antagonist MK-801 on Pyrithiamine-Induced Lesions and Amino Acid Changes in Rat Brain, *J. Neuroscience* 10(5):1664–1674 (1990).

Lemos et al., Two Types of Calcium Channels Coexist in Peptide-Releasing Vertebrate Nerve Terminals, *Neuron* 2:1419–1426 (1989).

Leung et al., Spider Toxins Selectively Block Calcium Currents in Drosophila, *Neuron* 3:767–772 (1989).

Malgouris et al., Riluzole, a Novel Antiglutamate, Prevents Memory Loss and Hippocampal Neuronal Damage in Ischemic Gerbils, *J. Neuroscience* 9(11):3720–3727 (1989).

Maryanoff et al., A Convenient Synthesis of Guanidines from Thioureas, *J. Org. Chem.* 51:1882–1884 (1986).

Meldrum, B., Protection Against Ischaemic Neuronal Damage by Drugs Acting on Excitatory Neuro-transmission, *Cerebrovascular and Brain Metabolism Reviews* 2:27–57 (1990).

Miura et al., Water-thinned ink compositions for writing an ink-jet printing, *Chemical Abstracts* 109:75454d (1988).

Plaitakis et al., Abnormal Glutamate Metabolism in an Adult-Onset Degenerative Neurological Disorder, *Science* 216:193–196 (1982).

Plummer et al., Elementary Properties and Pharmacological Sensitivities of Calcium Channels in Mammalian Peripheral Neurons, *Neuron* 2:1453–1463 (1989).

Podrebarac et al., Studies on Methylglyoxal Bis(guanylhydrazone) Analogs. I. Homologs of Methylglyoxal Bis(guanylhydrazone), *J. Med. Chem.* 6:283–288 (1963).

Prasad et al., Acylation of guanidines and guanylhydrazones, *Can. J. Chem.* 45:2247–2252 (1967).

Price et al., Excitatory Amino Acid Antagonists as Anti-Emetics, *Soc. Neuroscience Abstracts* 16:377 (1990).

Safir et al., Experimental Chemotherapy of Trypanosomiasis. II. The Preparation of Compounds Related to p-Phenyllenediguanidine, *J. Org. Chem.* 13:924–932 (1948).

Sah et al., Calcium Channels in Rat Neurons: High-Threshold Channels that are Resistant to Both w-Conotoxin and Dihydropyridine Blockers, *Soc. Neuroscience Abstr.* 15:823 (1989).

(List continued on next page.)

OTHER PUBLICATIONS

Sasaki et al., Synthesis of Adamantane Derivatives XXXI. A Facile Synthesis of 2'-Iminoadamantane-2-spiro-5'-imidazolidin-4'-one . . . , *Synthesis November* (11):718–719 (1975).

Scherz et al., Synthesis and Structure–Activity Relationships of N,N'-Di-o-tolylguandine Analogues, High-Affinity Ligands for the Haloperidol . . . , *Journal of Medicinal Chemistry* 33:2421–2429 (1990).

Stolyarchuk et al., Synthesis of furoylguanidines and comparison of their pharmacological properties of furoylureas, *Chemical Abstracts* 86:121071h (1977).

Subbarao et al., Avermectin Enhances Depolarization Evoked 3H-Gaba Release from Rat Brain Synaptosomes, *Soc. for Neurosci. Abstr.* 15:601 (1989).

Sunderdiek et al., Reaction of benzonitrile oxide with 1,4-disubstituted 1,2,4-triazolidine-3,5-diones (urazoles), *Chemical Abstracts* 81:91438k (1974).

Suszkiw, J. B., Properties of Presynaptic Voltage-Sensitive Calcium Channels in Rat Synaptosomes, *NATO ASI Series* H21:285–291 (1988).

Turner et al., A Comparison of the Subsecond Kinetics of 3H-Glutamate and Endogenous glutamate Release from Neurons, *Soc. Neurosci. Abstr.* 16:1014 (1990).

Turner et al., Multiple Components of Synaptosomal [3H]-gamma-Aminobutyric Acid Release Resolved by a Rapid Superfusion System, *Biochemistry* 28:586–593 (1989).

Turner et al., A Superfusion System Designed to Measure Release of Radiolabeled Neurotransmitters on a Subsecond Time Scale, *Analytical Biochemistry* 178:8–16 (1989).

Turner et al., Calcium Channels in Rat Brain Synaptosomes:Identification and Pharmacological Characterization, *Journal of Neuroscience* 5(3):841–849 (1985).

Vasilev et al., Interaction of N,N-dicyclohexylcarbodiimide with some amines for producing compounds having an antiviral effect, *Chemical Abstracts* 93:150095u (1980).

Weakley et al., N-Adamant-1-yl-N'-(2-iodophenyl)-guanidinium Chloride, *Acta Cryst.* C46:2234–2236 (1990).

Weber et al., 1,3-Di(2-[5-3H]tolyl)guanidine: A selective ligand that labels $\sigma$-type receptors for psychotomimetic opiates and antipsychotic drugs, *Proc. Natl. Acad. Sci. USA* 83:8784–8788 (1986).

D. Lloyd et al., *Tetrahedron*, 33:1379–1389 (1977).

H. Shimazu et al., *Chemical Abstracts*, 111(2):16337m (1989).

T. Tada et al., *Chemical Abstracts*, 104(24):208252g (1986).

L. Kiselev et al., *Chemical Abstracts*, 91(21):175291b (1979).

A. Heesing et al., *Chemical Abstracts*, 64(11):15776h (1966).

A. Akiba et al., *Bull. Chem. Soc. Jap.*, 47(4):935–937 (1974).

Database Rtecs, "National Institute of Occupational Safety and Health", RTECS No. MF735000.

J. Keana et al., *Proc. Natl. Acad. Sci.*, 86:5631–5635 (1989).

S. Siddiqui et al., *Pakistan Journal of Scientific and Industrial Res.*, 30(3):163–181 (1987).

E. Maida et al., *Wiener Klinische Wochenschrift*, 90(2):43–48 (1978).

C. Chavkin et al., *Advances in the Biosciences*, 75:407–410 (1989).

SUBSTITUTED GUANIDINES AND DERIVATIVES THEREOF AS MODULATORS OF NEUROTRANSMITTER RELEASE AND NOVEL METHODOLOGY FOR IDENTIFYING NEUROTRANSMITTER RELEASE BLOCKERS

The present invention was made with U.S. Government support. The U.S. Government has certain rights in the invention.

CROSS REFERENCE TO RELATED APPLICATIONS

The present application is a continuation-in-part of U.S. application Ser. No. 07/652,104, filed Feb. 8, 1991, now abandoned, the contents of which are fully incorporated by reference herein.

FIELD OF THE INVENTION

This invention is in the field of medicinal chemistry. In particular, this invention relates to modulators of neurotransmitter release, and to pharmaceutical compositions comprising the same which possess neuroprotective and other therapeutic utilities. The invention also relates to screening assays for compounds which inhibit neurotransmitter release. This invention further relates to methods involving the use of such neurotransmitter release modulators for the treatment or prevention of certain pathophysiologic conditions characterized by the excessive or inappropriate release of neurotransmitters.

BACKGROUND OF THE INVENTION

A wide variety of substituted guanidines are disclosed in the patent literature. For example:

U.S. Pat. Nos. 1,411,731 and 1,422,506 discloses diphenylguanidine as a rubber accelerator;

U.S. Pat. No. 1,597,233 discloses N-o-tolyl-N'-phenyl-guanidine as a rubber accelerator;

U.S. Pat. No. 1,672,431 discloses N,N'-di-o-methoxyphenylguanidine as being useful for therapeutic purposes, especially in the form of water-soluble salts;

U.S. Pat. No. 1,730,338 discloses N-p-dimethyl-amino-phenyl-N'-phenylguanidine as a rubber accelerator;

U.S. Pat. No. 1,795,738 discloses a process for the production of N,N'-dialkyl-di-substituted guanidines, including N-di-ethyl-N'-phenyl-guanidine, N-diethyl-N-isoamylguanidine, N-dimethyl-N'-isoamylguanidine and N-dimethyl-N'-ethylguanidine;

U.S. Pat. No. 1,850,682 discloses a process for the preparation of disubstituted guanidine rubber accelerators bearing an additional substituent on the imine nitrogen atom;

U.S. Pat. No. 2,145,214 discloses the use of disubstituted guanidines, e.g., diarylguanidines especially dixylylguanidine, as parasiticides;

U.S. Pat. No. 2,254,009 discloses sym-di-2-octylguanidine and U.S. Pat. Nos. 2,274,476 and 2,289,542 disclose sym-dicyclohexylguanidine as insecticides and moth larvae repellents;

U.S. Pat. No. 2,633,474 discloses 1,3-bis(o-ethylphenyl)guanidine and 1,3-bis(p-ethylphenyl)guanidine as rubber accelerators;

U.S. Pat. No. 3,117,994 discloses N,N',N''-trisubstituted guanidines and their salts as bacteriostatic compounds;

U.S. Pat. No. 3,140,231 discloses N-methyl- and N-ethyl-N'-octylguanidines and their salts as antihypertensive agents;

U.S. Pat. No. 3,248,246 describes (Example 5) a 1,3-disubstituted guanidine whose substituents are hydrophobic hydrocarbon groups, one of which is naphthylmethyl and the other is n-butyl;

U.S. Pat. No. 3,252,816 discloses various N-substituted and unsubstituted cinnamyl-guanidines and generically the corresponding N'- and N''-alkyl substituted compounds and their salts as antihypertensive agents;

U.S. Pat. No. 3,270,054 discloses N-2-adamant-1-yl- and N-2-homoadamant-1-yl-oxy-ethyl-thioethyl- and aminoethylguanidine derivatives bearing at most two lower alkyl groups on the N'- and/or N''-nitrogen atom as sympathicolytic and anti-viral agents;

U.S. Pat. No. 3,301,755 discloses N-ethylenically unsubstituted-alkyl-guanidines and the corresponding N'- and/or N''-lower alkyl compounds as hypoglycemic and antihypertensive agents;

U.S. Pat. No. 3,409,669 discloses N-cyclohexylamino-(3,3-dialkyl-substituted-propyl)-guanidines and the corresponding N'-alkyl- and/or N''-alkyl-substituted compounds as hypotensive agents;

U.S. Pat. No. 3,547,951 discloses 1,3-dioxolan-4-yl-alkyl-substituted guanidines which have anti-hypertensive activity and discloses lower alkyl, including n-butyl, as a possible substituent on the other amino group;

U.S. Pat. No. 3,639,477 discloses propoxylguanidine compounds as having anorectic properties;

U.S. Pat. Nos. 3,681,459; 3,769,427; 3,803,324; 3,908,013; 3,976,787; and 4,014,934 disclose aromatic substituted guanidine derivatives wherein the phenyl ring can contain hydroxy and/or halogen substituents for use in vasoconstrictive therapy;

U.S. Pat. No. 3,804,898 discloses N-benzylcyclobutenyl and N-benzylcyclobutenyl-alkyl-guanidines and the corresponding N-alkyl and/or N''-alkyl-substituted compounds as hypotensive agents;

U.S. Pat. No. 3,968,243 discloses N-aralkyl substituted guanidines and the corresponding N'-alkyl-N''-alkyl and N',N'-aralkyl compounds as being useful in the treatment of cardiac arrhythmias;

U.S. Pat. No. 3,795,533 discloses o-halo-benzylideneaminoguanidines and their use as anti-depressants for overcoming psychic depression;

U.S. Pat. No. 4,007,181 discloses various N,N'-disubstituted guanidines substituted on the imine nitrogen atom by a adamantyl as possessing antiarrhythmic and diuretic activities;

U.S. Pat. No. 4,051,256 discloses N-phenyl- and N-pyridyl-N'-adamantyl and cycloalkyl-guanidines as antiviral agents;

U.S. Pat. No. 4,109,014 discloses N-hydroxysubstituted guanidines and the corresponding N-methyl disubstituted guanidines as vasoconstrictor agents;

U.S. Pat. No. 4,169,154 discloses the use of guanidines in the treatment of depression;

U.S. Pat. No. 4,393,007 discloses N-substituted and unsubstituted, N-substituted methyl-N'-unsubstituted, monosubstituted and disubstituted-N''-unsubstituted and substituted guanidines as ganglionic blocking agents; and U.S. Pat. No. 4,471,137 discloses N,N,N'N''-tetraalkyl guanidines as being sterically hindered bases useful in chemical synthesis.

U.S. Pat. No. 4,709,094 discloses 1,3-disubstituted-guanidines, e.g., 1-3-dibutyl-guanidine and 1,3 di-o-tolyl-guanidine (DTG), as sigma brain receptor ligands.

For examples of other substituted guanidines, see, e.g., U.S. Pat. Nos. 1,422,506; 1,642,180; 1,756,315; 3,159,676; 3,228,975; 3,248,426; 3,283,003; 3,320,229; 3,479,437; 3,547,951; 3,639,477; 3,784,643; 3,949,089; 3,975,533; 4,060,640 and 4,161,541.

Geluk, H. W., et al., *J. Med. Chem.* 12:712 (1969) describe the synthesis of a variety of adamantyl disubstituted guanidines as possible antiviral agents, including N,N'-di-(adamantan-1-yl)-guanidine hydrochloride, N-(adamantan-1-yl)-N'-cyclohexyl-guanidine hydrochloride and N-(adamantan-1-yl)-N'-benzylguanidine hydrochloride.

PCT Application Publication No. WO88/00583 discloses diadamantylguanidine and N,N'-di-(2adamantyl)-guanidine. These compounds are reportedly useful for treating schizophrenia, psychosis, and depression.

Vasilev, P., et al., *Chem. Abstr.* 93:150095u, discloses a compound with the following formula:

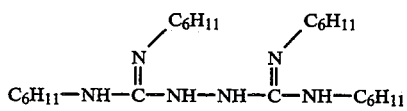

This compound reportedly has virucidal activity.

Ginsburg, V. A., et al., *Chem. Abstr.* 4518d (1962), and Ginsburg, V. A., et al., *Zhurnal Organ. Khimii* 7:2267–2270 (1971), disclose a compound having the formula:

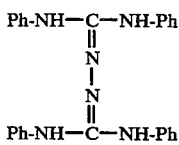

Kreutzberger and Schuker, *Arch Pharmz. Ber. Deut. Pharm. Ges.* 305:400–405 (1975), disclose a compound having the formula:

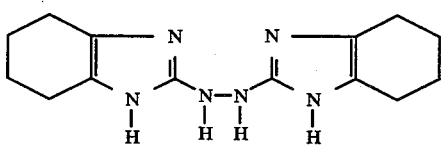

German Patent No. DE 2,452,691, discloses a compound having the formula:

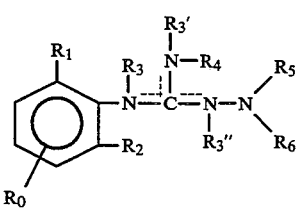

wherein, inter alia,
$R_0$ is hydrogen, halogen, hydroxy, alkoxy or $C_1$-$C_6$alkyl;
$R_1$ and $R_2$ are halogen, hydroxy, $C_1$-$C_4$ alkyl or $C_1$-$C_4$alkoxy;
$R_3$, $R_3'$ and $R_3''$ are hydrogen or $C_1$-$C_4$ alkyl;
$R_4$ is hydrogen, $C_1$-$C_4$ alkyl, hydroxy, $C_1$-$C_4$ alkoxy or an amino group;
$R_5$ and $R_6$ are hydrogen, $C_1$-$C_6$ alkyl, or an acyl group, or form a cyclic ring. Particular compounds disclosed in this patent document include 1-(2,6-dichlorophenyl)-2-(2,6-dichlorobenzylidine) aminoguanidine.HCl and 1-(2,6-dichlorophenyl)-2-cyclohexylidene-aminoguanidine. These compounds reportedly have antihypertensive properties.

Sunderdiek, R., et al., *Chem. Abstr.* 81:91439m (1974), disclose a compound having the formula:

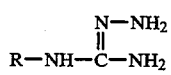

wherein R=Ph or cyclohexyl.

Bent, K. J., et al., *Chem. Abstr.* 74:63479m (1971), is an abstract of German Patent No. 2,029,707. This patent discloses antiviral compounds having the formula:

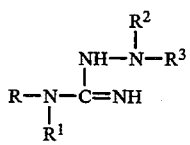

wherein:
R is amino, methyl, iso-butyl or p-substituted phenyls;
$R^1$ is hydrogen, methyl or iso-butyl;
$NRR_1$ is morpholino;
$R_2$ and $R_3$ are hydrogen, $CHC_6H_3Cl_2(2,4-)$, isopropyl, $C_6H_4p$-Cl, $CH(CH_2)_{10}CH_3$ or 1-(4-pyridyl)ethylidene.

Huisgen et al., *Chem. Abstr.* 63:2975d (1965), disclose a compound having the formula:

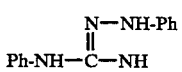

Kroeger, F., et al., *Chem. Abstr.* 60:9264f, disclose a compounds having the formulae:

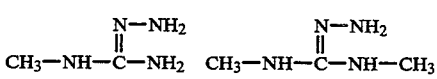

Heinisch, L., *J. Pract. Chem.* 329:290–300 (1987), discloses a compound having the formula:

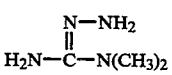

Kramer, C.-R., et al., *Biochem. Physiol. Pflanzen.* 178:469–477 (1983), disclose a compound having the formula:

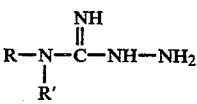

wherein R is hydrogen, methyl, butyl, hexyl, benzyl and phenyl, and R' is hydrogen or methyl. These compounds reportedly have algicidic activity.

Prasad, R. N., et al., *Can. J. Chem.* 45:2247–2252 (1967), disclose a compound having the formula:

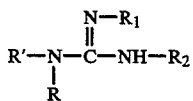

wherein R and R' are hydrogen or $Cl_2$—CH—CO—, $R_2$ is hydrogen, and R' is any one of a number of substituents having the general formula alkyl=N—. These compounds were evaluated for their antibacterial activity.

Huisgen et al., *Chem. Ber.* 98:1476–1486 (1965), disclose a compound having the formula:

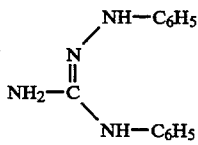

Podrebarac, E. G., et al., *J. Med. Chem.* :283–288 (1963), disclose compounds having the formula:

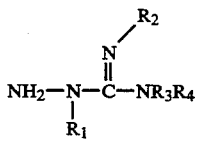

wherein the R groups may be hydrogen or methyl. These compounds were intermediates for the preparation of methylglyoxal bis(guanylhydrazone) analogs which may have activity against adult acute myelocytic leukemia.

Kroger et al., *Ber.* 97:396–404 (1964), disclose a compound having the formula:

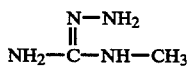

Durant, G. J., et al., *J. Med. Chem.* :22–27 (1966), disclose a compound having the formula:

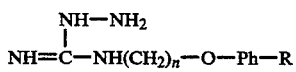

wherein R is an alkyl, halo, or alkoxy group. These compounds reportedly have antiinflammatory activity.

The amino acid L-glutamate is widely thought to act as a chemical transmitter substance at excitatory synapses within the central nervous system. Neuronal responses to glutamate are complex and appear to be mediated by at least three different receptor types, i.e., KA, QA and NMDA subtypes, each being named for their relatively specific ligands, i.e., kainic acid, quisaqualic acid and N-methyl-D-aspartic acid, respectively. An amino acid which activates one or more of these receptor types is referred to as an excitatory amino acid (EAA).

The NMDA subtype of excitatory amino acid receptors is activated during normal excitatory synaptic transmission in the brain. Activation of NMDA receptors under normal conditions is responsible for the phenomena of long-term potentiation, a memory-like phenomenon, at excitatory synapses. Excessive excitation of neurons occurs in epileptic seizures and it has been shown that over-activation of NMDA receptors contributes to the pathophysiology of epilepsy.

NMDA receptors are also strongly involved in nerve cell death which occurs following brain or spinal chord ischemia. Upon the occurrence of ischemic brain insults such as stroke, heart attack or traumatic brain injury, an excessive release of endogenous glutamate occurs, resulting in the over-stimulation of NMDA receptors. Associated with the NMDA receptor is an ion channel. The recognition site, i.e., the NMDA receptor, is external to the ion channel. When glutamate interacts with the NMDA receptor, it causes the ion channel to open, thereby permitting a flow of cations across the cell membrane, e.g., $Ca^{2+}$ and $Na^+$ into the cell and $K^+$ out of the cell. It is believed that this flux of ions, especially the influx of $Ca^{2+}$ ions, caused by the interaction of glutamate with the NMDA receptor, plays an important role in nerve cell death. See, e.g., Rothman, S. M. and Olney, J. W., *Trends in Neurosci.* 10(7):299–302 (1987).

In vitro studies have clearly demonstrated that activation of KA receptors can cause excitatory neuronal damage, although longer exposures are required (Koh, J. Y. et al., *J. Neurosci.* 10:693–705 (1990); and Frandsen, A. J. et al., *J. Neurochem.* 33:297–299 (1989)). The competitive KA receptor antagonist 2,3-dihydroxy-6-nitro-7-sulfamoylbenzoquinozaline (NBQX) is effective in preventing delayed neuronal degeneration following transient forebrain ischemia in rodents (Sheardown, M. J. et al., *Science* 247:571–574 (1990). However, such effects require relatively large and potentially toxic systemic doses of NBQX, apparently because this compound exhibits poor penetration of the blood-brain barrier.

At present, there is a critical need for effective treatments which limit the extent of nerve cell death following a stroke or traumatic brain injury. Recent advances in the understanding of the mechanisms underlying this nerve cell death have led to the hope that a drug treatment can be developed. Research and development efforts in this area have focussed on blocking the actions of glutamate that are mediated by the NMDA receptor-channel complex. Two approaches are well developed: competitive NMDA receptor antagonists (Choi D. W. (1990) *Cerebrov. Brain Metab. Rev.* 1:165–211; Watkins, J. C. and Olverman, H. J. (1987) *Trends Neurosci.* 10:265–272) and blockers of the ion channel of the NMDA receptor-channel complex (Meldrum, B. (1990) *Cerebrovascular Brain Metab. Rev.* 2:27–57; Choi, D. W. (1990) *Cerebrovascular Brain Metab. Rev.* 2:105–147; and Kemp, J. A. et al., *Trends Neurosci.* 10:265–272 (1987)). The ion-channel blocker MK-801 is an effective neuroprotective agent in a variety of in vivo models of stroke (Meldrum, B. (1990) *Cerebrovascular Brain Metab. Rev.* 2:27–57; Albers, G. W. et al., *Annals Neurol.* 25:398–403 (1989)). However, there is some toxicity associated with this class of compounds (Olney, J. W. et al., *Science* 244:1360–1362 (1989); Koek, W. and Colpaert, J. (1990) *J. Pharmacol. Exp. Ther.* 252:349–357) and NMDA antagonists have been shown to inhibit memory acquisition (Morris, R. G. M. (1988) in *Excitat. A.A.'s in Health*

*and Disease,* D. Lodge (ed.), Wiley, 297–320). These side effects may limit the clinical use of such agents to acute situations.

Blockers of neurotransmitter release have also received some attention as potential neuroprotective agents. For example, adenosine analogs may indirectly attenuate neurotransmitter release via G-protein-mediated inhibition of presynaptic Ca channels (Meldrum, B. *Cerebrovascular and Brain Metab. Rev.* 2:27–57 (1990); Dolphin, A. C. *Nature* 316:148–150 (1985)). It has been shown that such compounds are neuroprotective during ischemia in various rodent models of stroke (Evans, M. C. et al. *Neurosci. Lett.* 83:287–292 (1987)). Ault, B. and Wang, C. M., Br. *J. Pharmacol.* 87:695–703 (1986), disclose that adenosine inhibits epileptiform activity in hippocampal slices.

Other putative blockers of glutamate release act by an as yet undefined mechanism. The substituted piperidine derivative2-(4-(p-fluorobenzoyl)piperidin-1-yl)-2'-acetonaphthone (E-2001) (Kaneko, T. et al. *Arzneim-Forsch./Drug Res.* 39:445–450 (1989)) and the compound PK 26124 (riluzole, 2-amino-6-trifluoromethoxybenzothiazole) (Malgouris, C. et al. *J. Neurosci* 9:3720–3727 (1989)) have been shown to be neuroprotective in rodents. PK 26124, at therapeutic dosages in rats, does not seem to produce MK-801-like behavioral side effects in a controlled comparison of its efficacy/safety ratio with that of MK-801 (Koek, J. W. and Colpaert, F. C., *J. Pharmacol. Exp. Ther.* 252:349–357 (1990)). E-2001 ameliorates the degeneration of pyramidal neurons in the hippocampal CA1 sector following transient ischemia in Mongolian gerbils. In addition, E-2001 improves stroke symptoms induced by permanent unilateral carotid artery ligation in gerbils, prolonged the survival time following permanent bilateral carotid artery ligation in gerbils and mice, and prolonged the survival time following intravenous injection of KCN into mice. Kaneko, T. et al., *Arzneim.-Forsch./Drug Res.* 39:445–450 (1989).

It is believed that glutamate neurotoxicity is involved in acute injury to the nervous system as observed with seizure, hypoxia, hypoglycemia, and trauma, as well as in chronic degenerative diseases such as Huntington's disease, olivopontocereballar atrophy associated with glutamate dehydrogenase deficiency and decreased glutamate catabolism, Guam amyotrophic lateral sclerosis/Parkinsonium-dementia, Parkinson's disease, and Alzheimer's disease. Choi, D. W., *Neuron* 1:623–634 (1988); Choi, D. W., *Cereb. Brain Met. Rev.* 2:105–147 (1990).

Langlais, P. L. et al., *J. Neurosci* 10:1664–1674 (1990), disclose that glutamate and GABA may be involved in pyrithiamine-induced thiamine deficiency (PTD) which causes the formation of thalamic lesions and seizures. Administration of the NMDA receptor antagonist MK-801 during the late stages of PTD resulted in a marked attenuation of necrotic damage to the thalamus and periacqueductal gray and a reduction in the number and size of hemorrhagic lesions. Since thiamine deficiency is responsible for similar damage in Wernicke-Korsakoff's syndrome, Langlais et al. suggest that these results provide an important rational for the treatment of this human neuropathic condition.

Malgouris, C. et al., *J. Neurosci.* 9:3720–3727 (1989), disclose that PK 26124 (riluzole), a compound which inhibits glutamate release from nerve terminals, has anticonvulsant activity, improves sleep quality in rodents, and is active in protecting the rodent brain from the cellular and functional consequences of ischemia, including the prevention of memory loss and hippocampal neuronal damage.

Miller, et al., *New Anticonvulsant Drugs,* Meldrum, B. S. and Porter R. J. (eds), London:John Libbey, 165–177 (1986), disclose that the glutamate release blocker lamotragine is an anticonvulsant.

Price, M. T. and Olney, J. W., *Soc. Neurosci. Abstr.* 16:377, abstr. 161.16 (1990), disclose that the administration of EAA antagonists completely prevented emesis in ferrets that were subject to chemotherapy with cisplatin. The EAA antagonists employed did not penetrate the blood-brain barrier, and it was thus suggested that such compounds way prevent nausea, a common side effect during cancer chemotherapy.

Calcium antagonists such as nimodipine act both as cerebral vasodilators (Wong, M. C. W. and Haley, E. C. Jr., *Stroke* 24:31–36 (1989)), and to block calcium entry into neurons (Scriabine, A. *Adv. Neurosurg.* (1990)). Modest improvement in the outcome of stroke has been observed in clinical trials (Gelmers, H. J. et al., *N. Eng. J. Med.* 318:203–207 (1988)). While there are significant cardiovascular side effects, nimodipine appears less toxic than the NMDA antagonists and may find a role in the chronic treatment of stroke and other neurological disorders.

There are at least 3 subclasses of Ca channels, "T", "N", and "L", that differ in their pharmacology, location in neuronal and non-neuronal tissues, and physiological properties (Nowycky, M. C. et al. *Nature* 316:440–443 (1985); Bean, B. P. *Ann. Rev. Physiol.* 51:367–384 (1989)). Voltage-sensitive calcium channels (VSCC) in presynaptic nerve terminals control the influx of $Ca^{2+}$ and thereby determine the quantity and duration of transmitter released by the presynaptic action potentials. Biochemical $^{45}Ca$ tracer flux experiments with isolated nerve endings (synaptosomes) indicate that $K^+$-depolarization dependent $^{45}Ca$ entry consists of fast transient and slow sustained components. The transient Ca influx has been determined to represent a channel mediated process, whereas the sustained component reflects Ca entry via reversed Na/Ca exchange (Turner, T. and Goldin, S., *J. Neurosci.* 5:841–849 (1985); Suskziw, J. B. *NATO ASI Series,* H21:286–291 (1988); Suszkiw, J. B. et al. *J. Neurochem.* 42:1260–1269 (1989)).

European Patent Application No. 0 266 574, discloses that calcium overload blockers will be useful in the treatment of anoxia, ischemia, migraine and epilepsy. This application also discloses that certain piperidine derivatives have activity against calcium overload in the brain and may be used in the treatment of migraine.

Dreyer, E. B. et al., *Science* 248:364–367 (1990), disclose that the HIV-1 coat protein gp120 produces neuronal cell injury which may be responsible for the dementia and blindness encountered in acquired immunodeficiency syndrome (AIDS). Calcium channel antagonists prevented the gp120-induced neuronal injury of retinal ganglion cells. Dreyer et al. propose that calcium channel antagonists may prove useful in mitigating HIV-1 related neuronal injury.

SUMMARY OF THE INVENTION

It is an object of this invention to provide substituted guanidines, amino guanidines and N,N',N",N"'-tetrasubstituted hydrazinedicarboximidamides which modulate the release of neurotransmitters (e.g., glutamate) from neuronal cells.

Some disorders (e.g., neuronal damage in stroke) may be alleviated by inhibiting the release of EAAs such as glutamate. Some disorders (e.g., depression) may be alleviated by inhibiting the release of inhibitory neurotransmitters such as gamma-aminobutyric acid (GABA). Furthermore, inhibiting the release of an excitatory neurotransmitter (glutamate) may indirectly potentiate the release or the subsequent actions of an inhibitory transmitter (e.g., GABA), and thus serve to treat disorders known to be alleviated by more direct potentiation of inhibitory neurotransmission (in this example, anxiety and/or insomnia). This serves to illustrate the broad scope of the therapeutic potential of the compounds of the present invention. Thus, any disease that results from modulation of a particular neurotransmitter system can be counteracted by the substituted guanidines, amino guanidines and N,N',N'',N'''-tetrasubstituted hydrazinedicarboximidamides of the invention which act either on the same or another class of neurotransmitters.

It is yet a further object of the invention to treat or prevent nerve cell death resulting from hypoxia, hypoglycemia, brain or spinal cord ischemia, brain or spinal chord trauma, stroke, heart attack, or drowning, by the administration of effective amounts of substituted guanidines, amino guanidines and N,N', N'',N'''-tetrasubstituted hydrazinedicarboximidamides which inhibit the release of neurotransmitters from neuronal cells.

It is yet a further object of the present invention to treat or prevent various neurodegenerative diseases such as Huntington's disease, Amyotrophic Lateral Sclerosis, Alzheimer's disease, Down's Syndrome, Korsakoff's disease, olivopontocerebellar atrophy, HIV-induced dementia and blindness or multi-infarct dementia, by the administration of effective amounts of substituted guanidines, amino guanidines and N,N',N'',N'''-tetrasubstituted hydrazinedicarboximidamides which inhibit the release of neurotransmitters.

A further object of the invention is to provide substituted guanidines, amino guanidines and N,N',N'',N'''-tetrasubstituted hydrazinedicarboximidamides which are useful for the treatment or prevention of neurological conditions such as epilepsy and convulsions, carbon monoxide poisoning, cyanide poisoning, toxic brain damage caused by, for example, tetrodotoxin or shellfish toxins, anxiety, amnesia, migraine, river blindness, and nausea which may result from chemotherapy.

It is also an object of the present invention to provide a screening assay for inhibitors of neurotransmitter release (e.g. glutamate, dopamine, norepinephrine, glycine, aspartate, serotonin, and other neurotransmitters), from brain nerve terminals. It is also an object of the invention to provide a new screening assay which allows for the identification of new compounds which inhibit certain kinetic subcomponents of glutamate release. Such subcomponents can only be identified by an assay system capable of resolving neurotransmitter release on the subsecond time scale.

The screening assay of the invention comprises the following steps:

(a) contacting immobilized synaptosomes containing radiolabelled neurotransmitter with a compound suspected of inhibiting neurotransmitter release;

(b) inducing, by depolarization, the release of radiolabelled neurotransmitter from the immobilized radiolabelled synaptosomes obtained in step (a);

(c) washing the immobilized radiolabelled synaptosomes obtained in step (b) with a buffer comprising said compound and fractionating the effluent every 15 to 500 msec; and (d) detecting the relative amount of radiolabelled neurotransmitter in each fraction compared to control synaptosomes which have not been exposed to the compound of interest;

wherein a reduced amount of released radiolabelled neurotransmitter in the fractions from synaptosomes treated with the compound relative to control synaptosomes indicates that the compound inhibits neurotransmitter release.

The screening assay may be conducted in the presence or absence of $Ca^{2+}$ in order to identify those compounds which are selective inhibitors of one or more subcomponents or neurotransmitter release.

It is a further object of the present invention to provide novel substituted guanidines, amino guanidines and N,N',N'',N'''-tetrasubstituted hydrazinedicarboximidamides as well as pharmaceutical compositions thereof.

Upon further study of the specification and appended claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying Figures wherein:

FIG. 4 further depicts the non-correlation between inhibition of synaptosomal $^{45}Ca$-uptake by 10 $\mu M$ of the above-mentioned compounds and the inhibition of the phasic component of glutamate release.

DESCRIPTION OF THE PREFERRED EMBODIMENTS

The invention is related to the discovery that certain substituted guanidines, amino guanidines and N,N',N'',N'''-tetrasubstituted hydrazinedicarboximidamides have the ability to modulate, i.e. inhibit or potentiate the release of, or lengthen the time course of action of, neurotransmitters from neuronal tissue. As a result, these compounds may be used to treat or prevent those pathophysiologic conditions which result from excessive or inadequate release of neurotransmitters. Although applicants do not wish to be bound by any particular theory, it appears that the substituted guanidines, amino guanidines and N,N',N'',N'''-tetrasubstituted hydrazinedicarboximidamides of the invention mediate the inhibition of neurotransmitter release by blocking presynaptic calcium channels.

Figure 1:
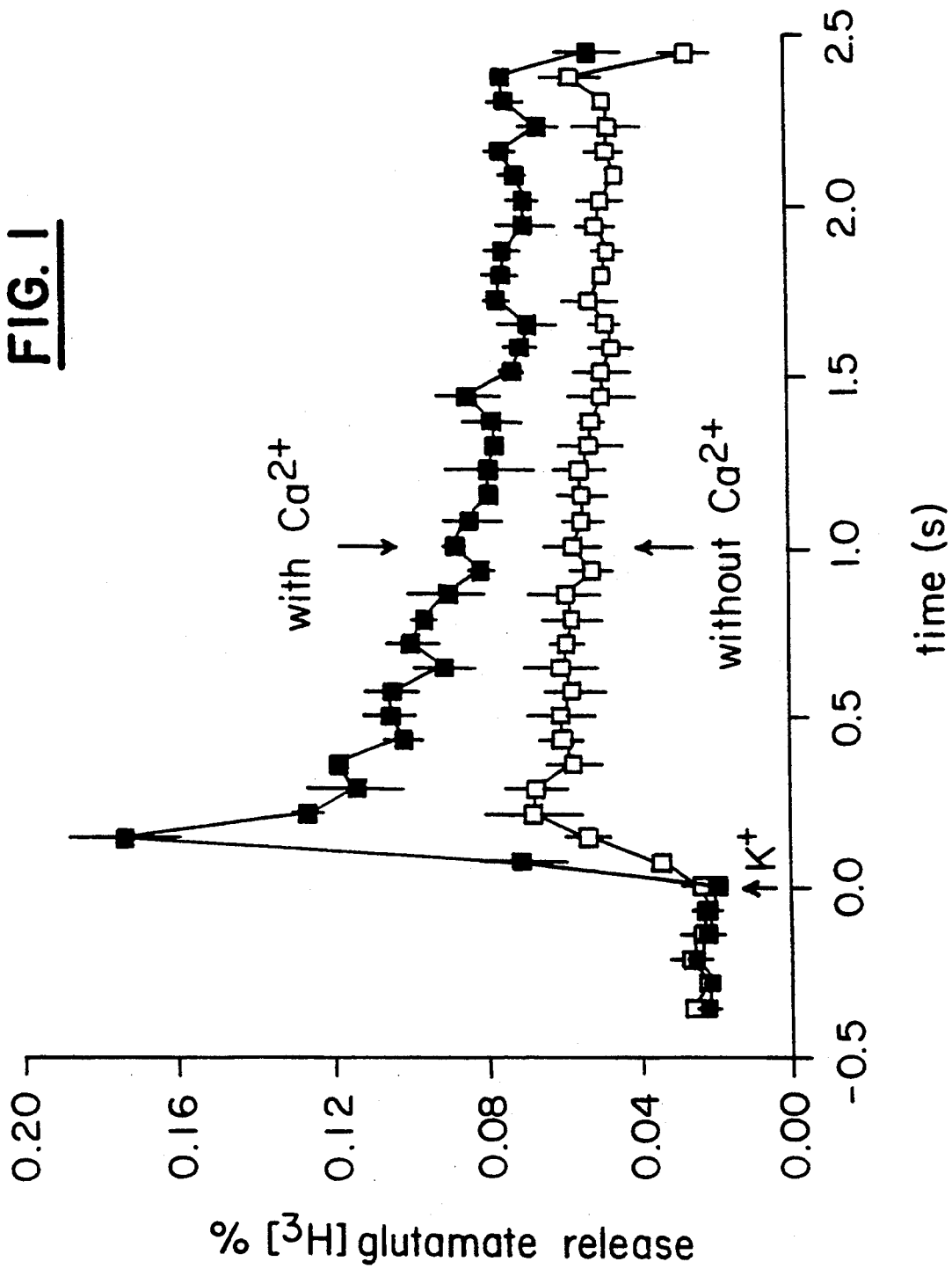
FIG. 1 depicts a graph showing $^3H$ glutamate release from rat brain synaptosomes in the presence and absence of 2.4 mM $Ca^{2+}$.
Figure 4:
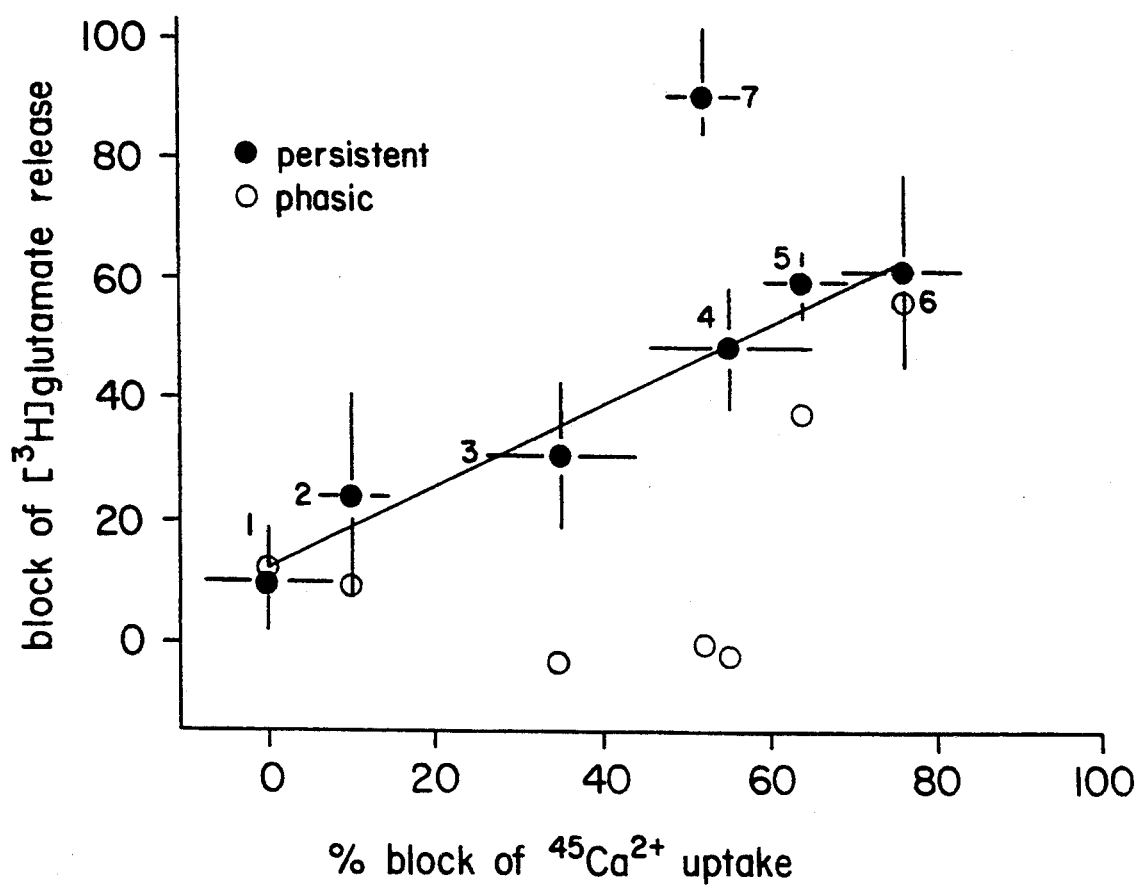
FIG. 4 depicts a graph showing the correlation between inhibition of synaptosomal $^{45}Ca$ uptake by 10 82 M of N-(adamantan-1-yl)-N'-(2-methylphenyl)guanidine (#1), N-(1-naphthyl)-N'-(m-ethylphenyl)-N'-methylguanidine (#2), N,N'-di-(1-naphthyl)guanidine (#3), N,N'-di-(adamantan-1-yl)guanidine (#4), N,N'-di-(adamantan-2-yl)guanidine (#5), N,N',N'',N'''-tetracyclohexylhydrazinedicarboximidamide (#6) and N,N'-di(5-acenaphthyl)guanidine (#7) and the inhibition of the tonic (persistent) Ca-dependent component of glutamate release, i.e. the component of release which does not rapidly decay, but persists for at least several seconds following depolarization.

Unexpectedly, the applicants have discovered that there are three distinct subcomponents of glutamate release from depolarized-stimulated neuronal cells. As shown in FIG. 1, the first component is a rapidly decaying Ca$^{2+}$-dependent phasic component with a decay time constant of <200 msec (termed the phasic component). A second component (termed tonic) is Ca$^{2+}$-dependent and persists for at least one second and generally for the duration of the depolarization. A third component is Ca$^{2+}$-independent and may result from the reversal of electrogenic Na-dependent glutamate uptake system. As shown in FIG. 4, blockage of the tonic Ca$^{2+}$-dependent component correlates well with the blockage of calcium uptake. Calcium influx into the nerve terminals is an important step in the cascade of changes which occur in neuronal cell death from ischemia. These results suggest that the substituted guanidines, amino guanidines and N,N',N'',N'''-tetrasubstituted hydrazine-dicarboximidamides of the invention hold promise in the prevention of neuronal death from ischemia.

The inhibition of glutamate release by the compounds of the invention does not appear to be related to any sigma receptor binding activity. Both N,N'-di-(adamantan-1-yl)guanidine and N,N'-di-(adamantan-2-yl)guanidine have similar inhibitory activity on glutamate release (55% and 60% inhibition at 30 μM, respectively) but widely different sigma receptor binding activities (IC$_{50}$=16.5 nM and 92.7 nM against $^3$H-DTG, respectively).

The identification of three subcomponents of inhibition of glutamate release allow for the screening of compounds which exhibit selectivity for the Ca$^{2+}$-dependent persistent component of glutamate release. The identification of such compounds will provide for more efficacious drugs with fewer side effects.

In general, substituted guanidines which may modulate neurotransmitter release and which are useful in the practice in the practice of the invention include compounds having the Formula (I):

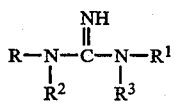

wherein

R and R$^1$ are the same or different and are cycloalkyl of 3 to 12 carbon atoms, e.g., cyclopropyl, cyclopentyl, cyclohexyl, cyclohexenyl, cycloheptyl, 1,4-methylenecyclohexyl, 1- or 2-adamantyl, exo or endo 2-norbornyl, exo or endo 2-isobornyl, menthyl, cyclopentyl-methyl, cyclohexylmethyl, 1- or 2-cyclohexylethyl and 1-, 2- or 3-cyclohexylpropyl; carbocyclic aryl, alkaryl, aralkyl or heterocyclic, e.g., of 6 to 18 carbon atoms and containing 1–3 separate or fused rings, and 0–5 O, N and/or S ring atoms in an aryl, alicyclic or mixed ring system, e.g., phenyl, benzyl, 1- and 2-phenylethyl, 1-, 2-, or 3-phenylpropyl; o-, m-, or p-tolyl, m,m'-dimethylphenyl, o-, m-, or p-ethylphenyl, m,m'-diethylphenyl, m-methyl-m'-ethylphenyl, o-propylphenyl, p-isopropylphenyl, p-tert-butylphenyl, p-n-propylphenyl, p-cyclopropylphenyl, p-cyclohexylphenyl, p-n-butylphenyl; naphthyl, e.g. 1- or 2-naphthyl; biphenyl; or a heterocyclic group such as indanyl, e.g. 4-indanyl; indenyl, e.g. 1- or 4-indenyl; acenaphthyl, e.g. 3- or 5-acenaphthyl; acenaphthylenyl, e.g. 5-acenaphthylenyl; indolyl, for example, 7-indolyl; benzthiazole, quinolinyl, isoquinolinyl, pyridyl, pyrimidinyl, pyrazinyl, furanyl, thienyl, pyrrolyl, thiazolyl, oxazolyl, imidazolyl and coumarinyl; and R$^2$ and R$^3$ are the same or different and are hydrogen, C$_1$–C$_6$ alkyl, lower C$_1$–C$_6$ alkylamino, aryl or substituted aryl; or R and R$_2$ or R$^1$ and R$^3$ form a C$_4$ to C$_6$ heterocyclic ring together with the guanidine nitrogen which may be fused to or substituted by a benzene ring.

The groups R, R$^1$, R$^2$ and R$^3$ may be substituted with one or more substituents including hydroxy, amino, oxo, lower C$_{1-6}$ alkyl, C$_1$–C$_6$ cycloalkyl, lower C$_1$–C$_6$ alkylamino, C$_1$–C$_6$ alkoxy, nitro, azido, cyano, isocyanato, amido, carbamido, sulfonate, or halogen, e.g. fluorine, chlorine, bromine or iodine.

Particular compounds within the scope of Formula I include N,N'-di(adamant-1-yl)guanidine, N,N'-di(adamant- 2-yl)guanidine, N-(adamantan-1-yl)-N'-(1-naphthyl)guanidine, N-(adamantan-2-yl)-N'-(1-naphthyl)guanidine, N-(adamantan-1-yl)-N'-(2-iodophenyl)guanidine, N-(adamantan-1-yl)-N'-(2-methylphenyl)guanidine, N-(adamantan-2-yl)-N'-(2-methylphenyl)guanidine, N-((±)-endo-2-norbornyl)-N'-(2-iodophenyl)guanidine, N-(α-naphthyl)-N'-(2-iodophenyl)guanidine, N-(3-ethylphenyl)-N'-(1-naphthyl)guanidine, N-(1-naphthyl)-N'-(m-ethylphenyl)-N'-methylguanidine, N,N'-di(4-n-butylphenyl)guanidine, N,N'-di(4-cyclohexylphenyl)guanidine, N,N'-di(4-biphenyl)guanidine, N,N'-di(4-neopentylphenyl)guanidine, N,N'-di(4-cyclopropylphenyl)guanidine, N,N'-di(4-isopropylphenyl)guanidine, and N,N'-di(4-tert.butylphenyl)guanidine.

Preferred disubstituted guanidines within the scope of general Formula (I) include compounds having the Formula (II):

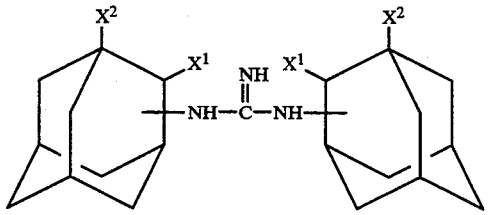

wherein the guanidine nitrogen may be substituted at any position of the adamantyl groups;

$R^2$ and $R^3$ are as defined above;

$X^1$ and $X^2$ are the same or different and are selected from the group consisting of hydrogen, hydroxy, acetate, oxo, amino, lower $C_{1-6}$ alkyl, amino, alkoxy of 1-6 carbon atoms, e.g., methoxy, ethoxy and propoxy; lower $C_{1-6}$ alkyl amino, di-lower $C_{2-12}$ alkyl amino, nitro, azido, sulfhydryl, cyano, isocyanato, or halogen, e.g. fluoro, chloro, bromo, or iodo; amido, e.g., acetamido, N-ethylacetamido; carbamido, e.g., carbamyl, N-methylcarbamyl, N,N'-dimethylcarbamyl; etc., wherein at least one of $X^1$ and $X^2$ is other than hydrogen.

Other preferred guanidines within the scope of general Formula (I) include compounds having the Formula (III):

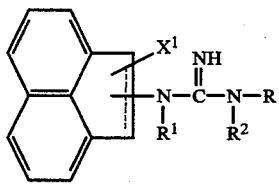

wherein R, $R^1$, $R^2$, and $X^1$ are as defined above.

Preferred compounds within the scope of general Formula III include N,N'-di-(1-acenaphthyl)guanidine, N,N'-di-(3-acenaphthyl)guanidine, N,N'-di-(5-acenaphthyl)guanidine, N,N'-di-(acenaphthylen-1-yl)guanidine, N-(adamantan-1-yl)-N'-(5-acenaphthyl)guanidine; N-(adamantan-2-yl)-N-(5-acenaphthyl)guanidine; N-(adamantan-1-yl)-N-(3-acenaphthyl)guanidine; N-(adamantan-2-yl)-N'-(3-acenaphthyl)guanidine; N-(adamant-1-yl)-N'-(adamant-2-yl)guanidine; N-(3-acenaphthyl)-N'-(4-fluoronaphthyl)guanidine; N-(5-acenaphthyl)-N'-(4-fluoronaphthyl)guanidine; N-(3-acenaphthyl)-N'-(4-hydroxynaphthyl)guanidine; N-(5-acenaphthyl)-N'-(4-hydroxynaphthyl)guanidine; N-(3-acenaphthyl)-N'-(4-methoxynaphthyl)guanidine; N-(5-acenaphthyl)-N'-(4-methoxynaphthyl)guanidine; N-(3-acenaphthyl)-N'-(4-nitronaphthyl)guanidine; N-(5-acenaphthyl)-N'-(4-nitronaphthyl)guanidine; N-(3-acenaphthyl)-N'-(4-aminonaphthyl)guanidine; N-(5-acenaphthyl)-N'-(4-aminonaphthyl)guanidine; N-(3-acenaphthyl)-N'-(4-azidonaphthyl)guanidine; N-(5-acenaphthyl)-N'-(4-azidonaphthyl)guanidine; N-(3-acenaphthyl)-N'-(4-bromonaphthyl)guanidine; N-(3-acenaphthyl)-N'-(4-bromonaphthyl)guanidine; N-(3-acenaphthyl)-N-(4-cyanonaphthyl)guanidine; N-(5-acenaphthyl)-N-(4-cyanonaphthyl)guanidine; N-(3-acenaphthyl)-N'-(4-amidonaphthyl)guanidine; N-(5-acenaphthyl)-N'-(4-amidonaphthyl)guanidine; N-(3-acenaphthyl)-(4-iodonaphthyl)guanidine; N-(5-acenaphthyl)-(4-iodonaphthyl)guanidine; N-(3-acenaphthyl)-N'-(7-fluronaphthyl)guanidine; N-(5-acenaphthyl)-N'-(7-fluronaphthyl)guanidine; N-(3-acenaphthyl)-N'-(2-fluoronaphthyl)guanidine; N-(5-acenaphthyl)-N'-(2-fluoronaphthyl)guanidine; N-(3-acenaphthyl)-N'-(2-methoxynaphthyl)guanidine; N-(5-acenaphthyl)-N'-(2-methoxynaphthyl)guanidine; N-(3-acenaphthyl)-N'-(2-hydroxynaphthyl)guanidine; N-(5-acenaphthyl)-N'-(2-hydroxynaphthyl)guanidine; N-(3-acenaphthyl)-N'-(2-aminonaphthyl)guanidlne; N-(5-acenaphthyl)-N'-(2-aminonaphthyl)guanidine; N-(3-acenaphthyl)-N'-(4-isopropylphenyl)guanidine; N-(5-acenaphthyl)-N'-(4-isopropylphenyl)guanidine; N-(3-acenaphthyl)-N'-(4-n-propylphenyl)guanidine; N-(5-acenaphthyl)-N'-(4-n-propylphenyl)guanidine; N-(3-acenaphthyl)-N-(2-isopropylphenyl)guanidine; N-(5-acenaphthyl)-N-(2-isopropylphenyl)guanidine; N-(3-acenaphthyl)-N-(4-cyclopropylphenyl)guanidine; N-(5-acenaphthyl)-N-(4-cyclorpopylphenyl)guanidine; N-(3-acenaphthyl)-N'-(coumarinyl)guanidine; N-(5-acenaphthyl)-N'-(coumarinyl)guanidine; N-(3-acenaphthyl)-N'-(quinolinyl)guanidine; N-(5-acenaphthyl)-N'-(quinolinyl)guanidine; N-(4-hydroxy-3-acenaphthyl)-N'-(adamant-1-yl)guanidine; N-(4-hydroxy-3-acenaphthyl)-N'-(adamant-2-yl)guanidine; N(4-hydroxy-5-acenaphthyl)-N'-(adamant-1-yl)guanidine; N-(4-hydroxy-5-acenaphthyl)-N'-(adamant-b 2-yl)guanidine; N-(4-nitro-5-acenaphthyl)-N'-(adamant-1-yl)guanidine; N-(4-nitro-5-acenaphthyl)-N'-(adamant-2-yl)guanidine; N-(4-amino-3-acenaphthyl)-N'-(adamant-1-yl)guanidine; N-(4-amino-3-acenaphthyl)-N'-(adamant-2-yl)guanidine; N-(4-amino-5-acenaphthyl)-N'-(adamant-1-yl)guanidine; N-(4-amino-5-acenaphthyl)-N'-(adamant-2-yl)guanidine; N-(4-methoxy-3-acenaphthyl)-N'-(adamant-1-yl)guanidine; N-(4-methoxy-3-acenaphthyl)-N'-(adamant-2-yl)guanidine; N-(4-methoxy-5-acenaphthyl)-N'-(adamant-1-yl)guanidine; N-(4-methoxy-5-acenaphthyl)-N'-(adamant-2-yl)guanidine; N-(4-bromo-3-acenaphthyl)-N'-(adamant-1-yl)guanidine; N-(4-bromo-3-acenaphthyl)-N'-(adamant-2-yl)guanidine; N-(4-bromo-5-acenaphthyl)-N'-(adamant-1-yl)guanidine; N-(4-bromo-5-acenaphthyl)-N'-(adamant-2-yl)guanidine; N-(1-oxo-3-acenaphthyl)-N'-(adamant-1-yl)guanidine; N-(1-oxo-3-acenaphthyl)-N'-(adamant-2-yl)guanidine; N-(1-oxo-5-acenaphthyl)-N'-(adamant-1-yl)guanidine; N-(1-oxo-5-acenaphthyl)-N'-(adamant-2-yl)guanidine; N-(2-oxo-3-acenaphthyl)-N'-(adamant-1-yl)guanidine; N-(2-oxo-3-acenaphthyl)-N'-(adamant-2-yl)guanidine; N-(2-oxo-5-acenaphthyl)-N'-(adamant-1-yl)guanidine; N-(2-oxo-5-acenaphthyl)-N'-(adamant-2-yl)guanidine; N-(1-bromo-3-acenaphthyl)-N'-(adamant-1-yl)guanidine; N-(1-bromo-3-acenaphthyl)-N'-(adamant-2-yl)guanidine; N-(1-bromo-5-acenaphthyl)-N'-(adamant-1-yl)guanidine; N-(1-bromo-5-acenaphthyl)-N'-(adamant-2-yl)guanidine; N-(2-bromo-3-acenaphthyl)-N'-(adamant-2-yl)guanidine; N-(2-bromo-3-acenaphthyl)-N'-(adamant-2-yl)-guanidine; N-(2-bromo-5-acenaphthyl)-N'-(adamant-1-yl)guanidine; N-(2-bromo-5-acenaphthyl)-N'-(adamant-2-yl)guanidine; N-(1-hydroxy-3-acenaphthyl)-N'-(adamant-1-yl)guanidine; N-(1-hydroxy-3-acenaphthyl)-N'-(adamant-2-yl)guanidine; N-(1-hydroxy-5-acenaphthyl)-N'-(adamant- 1-yl)guanidine; N-(1-hydroxy-5-acenaphthyl)-N'-(adamant-2-yl)guanidine; N-(2-hydroxy-3-acenaphthyl)-N'-(adamant-1-yl)guanidine; N-(2-hydroxy-3-acenaphthyl)-N'-(adamant-2-yl)guanidine; N-(2-hydroxy-5-acenaphthyl)-N'-(adamant-1-yl)guanidine; N-(2-hydroxy-5-acenaphthyl)-N'-(adamant-2-yl)guanidine; N-(3-acenaphthylenyl)-N'-(adamant-1-yl)guanidine; N-(3-acenaphthylenyl)-N'-(adamant- 2-yl)guanidine; N-(5-acenaphthylenyl)-N'-(adamant-1-yl)guanidine; N-(5-acenaphthylenyl)-N'-(adamant-2-yl)guanidine; N,N'-bis(4-bromo-3-acenaphthyl)guanidine; N,N'-bis(4-bromo-5-acenaphthyl)guanidine; N,N'-bis(4-hydroxy-3-acenaphthyl)-guanidine; N,N'-bis(4-hydroxy-5-acenaphthyl)guanidine; N,N'-bis(4-amino-3-acenaphthyl)guanidlne; N,N'-bis(4-amino-5-acenaphthyl)guanidine; N,N'-bis(4-nitro-3-acenaphthyl)guanidine; N,N'-bis(4-nitro-5-acenaphthyl)guanidine; N,N'-bis(1-bromo-3-acenaphthyl)-guanidine; N,N'-bis(1-bromo-5-acenaphthyl)guanidine; N,N'-bis(2-bromo-3-acenaphthyl)guanidine; N,N'-bis(2-bromo-5-acenaphthyl)guanidine; N,N'-bis(1-hydroxy-3-acenaphthyl)guanidine; N,N'-bis(1-hydroxy-5-acenaphthyl)-guanidine; N,N'-bis(2-hydroxy-3-acenaphthyl)guanidine; N,N'-bis(2-hydroxy-5-acenaphthyl)guanidine; N,N'-bis(1-oxo-3-acenaphthyl)guanidine; N,N'-bis(1-oxo-5-acenaphthyl)guanidine; N,N'-bis(2-oxo-3-acenaphthyl)guanidine; N,N'-bis(2-oxo-5-acenaphthyl)-guanidine; N,N'-bis(3-acenaphthylenyl)guanidine; N,N$^1$-bis(4-azido-5-acenaphthyl)guanidine; N,N$^1$-bis(4-sulfonyl-5-acenaphthyl)guanidine; and N,N'-bis(5-acenaphthylenyl)guanidine.

Other substituted guanidines which may modulate neurotransmitter release and which are useful in the practice in the practice of the invention include compounds having the Formula (IV):

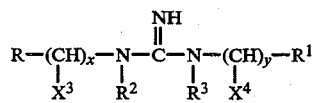

wherein R, R$^1$, R$^2$ and R$^3$ are as described above, X$^3$ and X$^4$ have the same meaning as X$^1$ and X$^2$; and X and y are the same or different and are 0, 1, 2, 3 or 4.

Preferred substituted guanidines within the scope of general Formula (I) include compounds having the Formula (V):

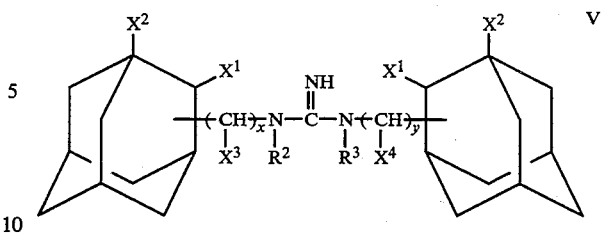

wherein R$^2$, R$^3$, X$^1$, X$^2$, X$^3$, X$^4$, x any y are as described above.

Preferred substituted guanidines within the scope of Formula (V) include N,N'-di-(3-nitroadamantan-1-yl)guanidine, N,N'-di-(3-hydroxyadamantan-1-yl)guanidine, N,N'-di-(3-amino-adamantan-1-yl)guanidine, N,N'-di-(3-nitro-adamantan-2-yl)guanidine, N,N'-di-(3-hydroxyadamantan-2-yl)guanidine, N,N'-di-(3-aminoadamantan-2-yl)-guanidine, N,N'-di-(5-nitroadamantan-2-yl)-guanidine, N,N'-di-(5-hydroxyadamantan-2-yl)-guanidine, N,N'-di-(5-aminoadamantan-2-yl)guanidine, N,N'-di-(methylene-adamantan-1-yl)guanidine, N,N'-di-(methylene-adamantan-2-yl)guanidine, N-(adamantan- 1-yl)-N'-(methyleneadamantan-1-yl)-guanidine, N-(adamantan-2-yl)-N'-(methyleneadamantan-2-yl)-guanidine, N-(adamantan-1-yl)-N'-(methyleneadamantan-2-yl)guanidine, N-(adamantan-2-yl)-N'-(methyleneadamantan-1-yl)guanidine, N,N'-di-(methylene-(3-aminoadamantan-1-yl) )guanidine, N,N'-di-(methylene-(3-aminoadamantan-2-yl) )guanidine, N,N'-di-(methylene-(3-hydroxyadamantan-1-yl) )guanidine, N,N'-di-(methylene-(3-hydroxyadamantan-2-yl) )guanidine, N,N'-di-(methylene-(3-mercaptoadamantan-1-yl))guanidine, N,N'-di-(methyl-ene-( 3-mercapto-adamantan-2-yl))guanidine, N,N'-di-(methyl-ene-(3-mercaptoadamantan-1-yl))guanidine, N,N'-di-(methylene-(3-mercaptoadamantan-2-yl))guanidine, N,N'-di-(methylene-(3-cyanoadamantan-1-yl))guanidine, N,N'-di-(methylene-(3-cyanoadamantan-2-yl))guanidine, N,N'-di-(methylene-(3-cyanoadamantan-1-yl))guanidine and N,N'-di-(methylene-(3-cyanoadamantan-2-yl))guanidine.

Other substituted guanidines which may modulate neurotransmitter release and which are useful in the practice in the practice of the invention include compounds having the Formula (VI):

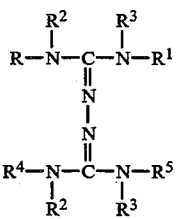

wherein R, R$^1$, R$^2$ and R$^3$ are as defined above and R$^4$ and R$^5$ have the same meaning as R and R$^1$. Compounds having Formula (V) may be either symmetrical dimers of a single guanidine or conjugates of different guanidines.

Especially preferred compounds within the scope of Formula (VI) which may be used in the practice of the invention include N,N',N'',N'''-tetracyclohexylhydrazinedicarboximidamide, N,N',N'',N'''tetraphenylhydrazinedicarboximidamide, N,N'-di-(adamantan-1-yl)-N'',N'''-dicyclohexylhydrazinedicarboximidamide, N,N'-di-(adamantan-2-yl)-N'',N'''-dicyclohexylhydrazinedicarboximidamide, N,N',N'',N'''-tetra-(adamantan-1-yl)-hydrazinedicarboximidamide, N,N',N'',N'''-tetra-(adamantan-2-yl)-hydrazinedicarboximidamide, N,N'-di-(adamantan-1-yl)-N'',N'''-di-(adamantan-2-yl)-hydrazinedicarboximidamide, N,N'-di(2-norbornyl)-N'',N'''-dicyclohexylhydrazinedicarboximidamide, N,N'-di-(2-isobornyl)-N'',N'''-dicyclohexylhydrazinedicarboximidamide, N,N'-di-(2isobornyl)-N'',N'''-di-(adamantan-1-yl)hydrazinedicarboximidamide, and N,N'-di-(2-isobornyl)-N'',N'''-di-(adamantan-2-yl)hydrazinedicarboximidamide.

Other substituted guanidines which may modulate neurotransmitter release and which are useful in the practice in the practice of the invention include compounds having the Formula (VII):

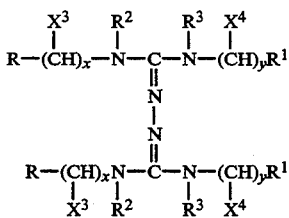

wherein R, $R^1$, $R^2$, $R^3$, $X^3$, $X^4$, x and y are as defined above. Preferred compounds having Formula (VI) are wherein R and $R^1$ are adamantyl groups.

Other substituted guanidines which may modulate neurotransmitter release and which are useful in the practice in the practice of the invention include compounds having the Formula (VIII):

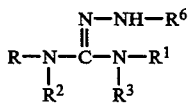

wherein R, $R^1$ $R^2$ and $R^3$ are as described above and $R^6$ is hydrogen, $C_1$-$C_6$ alkyl, $C_3$-$C_{12}$ cycloalkyl, carbocyclic aryl, nitrile, $C_1$-$C_6$ alkoxycarbonyl, $C_1$-$C_6$ acyl or benzoyl.

Other substituted guanidines which may modulate neurotransmitter release and which are useful in the practice in the practice of the invention include compounds having the Formula (IX):

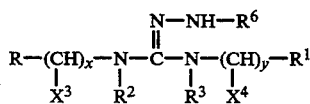

wherein R, $R^1$, $R^2$, $R^3$, $R^6$, $X^3$, $X^4$, x and y are as defined above.

Preferred compounds within the scope of Formula (IX) include N,N'-dicyclohexyl-N''-aminoguanidine, N,N'-di-(adamantan-1-yl)-N''-aminoguanidine, N,N'-di-(adamantan-2-yl)-N''-aminoguanidine, N,N'-di-(2-norbornyl)-N''-aminoguanidine, and N,N'-di-(2-isobornyl)-N''-aminoguanidine.

Preferably, 0, 1, 2, 3 or more polar groups defined by $X^1$ and $X^2$ may be present on the R groups of compounds having Formulae (I)–(IX). Especially preferred are compounds of Formulae (I )–(IX) wherein at least one of R and $R^1$ is a 1- or 2-substituted adamantyl group or a 3- or 5-acenaphthyl group. Other especially preferred compounds are those with increased aqueous solubility. Such compounds are where at least one of $X^1$ or $X^2$ is a polar group or at least one of R and $R^1$ is substituted by a polar group.

The substituted guanidines, amino guanidines and N,N',N'',N'''-tetrasubstituted hydrazinedicarboximidamides of the invention may exist as any one of a number of tautomeric isomers. Any one of these tautomeric isomers are within the scope of compounds which are useful in the claimed invention.

The substituted guanidines, amino guanidines and N,N',N'',N'''-tetrasubstituted hydrazinedicarboximidamides of the invention are effective modulators of neurotransmitter release from ischemic neuronal cells. Modulation of neurotransmitter release involves either the inhibition of neurotransmitter release, the potentiation of neurotransmitter release, or the modulation of the time course of action of neurotransmitters.

The compounds of the invention are effective inhibitors if they cause at least about a 50% inhibition of neurotransmitter release at a concentration of about 100 μM according to the protocol disclosed herein. More preferably, the compounds cause at least about a 50% inhibition of neurotransmitter release at a concentration of about 30 μM. The compounds of the invention are effective potentiators of neurotransmitter release if they cause at least about a 50% potentiation of neurotransmitter release at a concentration of about 100 μM. More preferably, the compounds cause at least about a 50% potentiation of neurotransmitter release at a concentration of about 30 μM. The compounds of the invention are effective upward or downward modulators of neurotransmitter decay kinetics if they cause a doubling or halving, respectively, of the neurotransmitter release kinetics. For example, effective upward modulators of neurotransmitter release kinetics may cause a doubling of decay kinetics from about 100 msec (as observed for the $Ca^{2+}$-dependent tonic component of glutamate release) to about 200 msec.

The neurotransmitters which may modulate neurotransmitter release include, but are not limited to glutamate, dopamine, norepinephrine, glycine, aspartate, and serotonin. One of ordinary skill in the art can identify those compounds which are effective modulators of neurotransmitter release using the procedures disclosed herein with no more than routine experimentation.

The most promising compounds for treatment or prevention of neuronal death can be evaluated in vivo in one or more variations of the rat middle cerebral artery occlusion model. Such models are generally considered to be particularly predictive or neuroprotective efficacy in stroke (Ginsburg, M. D. and Busto, R. B., Stroke 20:1627–1642 (1989)).

In parallel, the efficacy of lead candidates may be assessed in the widely accepted 4-vessel occlusion model of global ischemia (Pulsinelli, W. A. and Buchan, A. M., Stroke 19: 913–941 (1988)). Initially, clasps are placed around each common carotid artery of anaesthetized rats, and the vertebral arteries are electrocoagulated. After 24 hours, the clasps are tightened for 10–30 minutes and then loosened to allow reperfusion. Three days later, the animals are sacrificed and the brains are examined histologically.

Numerous studies have emphasized the importance of administration of neuroprotective drugs very soon after the ischemic insult (Ginsburg, M. D., and Busto, R. B.,

*Stroke* 20:1627–1642 (1989)). Therefore, in both models, candidate compounds may be administered intravenously or intraperitoneally at varying time intervals within 1 hour after the onset of ischemia, to evaluate the optimum window of therapeutic efficacy.

Disubstituted guanidines are the subject of copending application Ser. No. 07/237,367 filed Aug. 29, 1988, and U.S. Pat. No. 4,709,094, whose disclosures are incorporated herein by reference. The preferred guanidines in U.S. Pat. No. 4,709,094 are described therein by the formula:

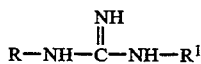

wherein R and $R^1$ are each independently alkyl, cycloalkyl, carbocyclic aryl, alkaryl or aralkyl. As a class, these compounds are described in this patent as exhibiting a highly selective binding activity to the sigma brain receptor. In copending application Ser. No. 07/237,367, it is disclosed that additional specific members of this class of disubstituted guanidines exhibit a high binding activity for the PCP receptor.

These N,N'-disubstituted guanidines of Formula III can readily be prepared by conventional chemical reactions, e.g., when R and $R^1$ are the same, by reaction of the corresponding amine with cyanogen bromide. Other methods which can be employed include the reaction of an amine with a preformed cycloalkyl or aryl cyanamide. See Safer, S. R., et al., *J. Org. Chem.* 13:924 (1948). This is the method of choice for producing asymmetrical N,N'-disubstituted guanidines. For a recent synthesis of asymmetrical guanidines, see G. J. Durant et al., *J. Med. Chem.* 28:1414 (1985), and C. A. Maryanoff et al., *J. Org. Chem.* 51:1882 (1986), the disclosures of which are incorporated by reference herein.

The compounds having Formulae (VI) and (VII) may be prepared by reacting a symmetrical or unsymmetrical carbodiimide with hydrazine in an organic solvent (see the Examples). The compounds having Formulae (VIII) and (IX) may be prepared by reacting a symmetrical or unsymmetrical carbodiimide with hydrazine to give a 1:1 adduct. See Example 2; Weygand and Hilgetag in *Preparative Organic Chemistry*, Hilgetag and Martini (eds.), John Wiley & Sons, New York, N.Y., page 408 (1972); or Vasilev, P. et al., *Chem. Abstr.* 93:150095u.

The compounds of the invention bearing R and $R^1$ groups having polar substituents may be prepared using the above-noted methods wherein the starting material (R—$NH_2$ or $R^1$—$NH_2$) has a polar group or a protected form thereof. Methods for preparing such starting materials are taught, for example, in U.S. Pat. No. 4,649,222, Morat and Rassat, *Tet. Lett.*:4561–4564 (1979); Sollott and Gilbert, *J. Org. Chem.* 45:5405–5408 (1980); and Zajac, W. W. et al., *J. Org. Chem.* 54:2468–2471 (1989); the disclosures of which are incorporated by reference herein in their entirety.

N,N'-disubstituted-N''-aminoguanidines may be prepared according to any of the methods which are well known in the art. See, for example, German Patent No. DE 2,452,691, Sunderdiek, R., et al., *Chem. Abstr.* 81:91439m (1974), Bent, K. J., et al., *Chem. Abstr.* 74:63479m (1971), German Patent No. 2,029,707, Huisgen et al., *Chem. Abstr.* 63:2975d (1965), Kroeger, F., et al., *Chem. Abstr.* 60:9264f, Heinisch, L., *J. Pract. Chem.* 329:290–300 (1987), Kramer, C.-R., et al., *Biochem. Physiol. Pflanzen.* 178:469–477 (1983), Prasad, R. N., et al., *Can. J. Chem.* 45:2247–2252 (1967), Huisgen et al., *Chem. Ber.* 98:1476–1486 (1965), Podrebarac, E. G., et al., *J. Med. Chem.* 6:283–288 (1963), Kroger et al., *Ber.* 97:396–404 (1964), and Durant, G. J., et al., *J. Med. Chem.* 9:22–27 (1966).

In a compositional aspect, this invention relates to a pharmaceutical composition in unit dosage form and adapted for systemic administration to a subject, e.g., a human being, comprising per unit dosage an amount of a substituted guanidine, amino guanidine or N,N',N'',N'''-tetrasubstituted hydrazinedicarboximidamide of the invention effective to modulate the release of a neurotransmitter. Preferably, the neurotransmitter is glutamate. Such compounds are preferably effective modulators of neurotransmitter release from ischemic neuronal cells.

In another compositional aspect, this invention relates to a neuroprotecting substituted guanidine, amino guanidine or N,N',N'',N'''-tetrasubstituted hydrazinedicarboximidamide of the invention which modulates the release of a neurotransmitter, in particular glutamate, and the physiologically acceptable salts thereof. Preferably, such compounds are effective inhibitors of neurotransmitter release from ischemic neuronal cells.

In a method aspect, this invention relates to a method for treating or preventing certain neurological disorders, including nausea resulting from chemotherapy, the consequences of stroke or traumatic brain injury, epilepsy or neurological diseases, carbon monoxide poisoning, cyanide poisoning, toxic brain damage caused by, for example, tetrodotoxin or shellfish toxins, anxiety, and river blindness, comprising the administration of an effective amount of a substituted guanidine, amino guanidine or N,N',N'',N'''-tetrasubstituted hydrazinedicarboximidamide of the invention which inhibits the release of a neurotransmitter to a subject in need of such treatment. Such substituted guanidines, amino guanidines and N,N',N'',N'''-tetrasubstituted hydrazinedicarboximidamides of the invention may be non-competitive blockers of neurotransmitter (e.g. glutamate) release. Preferably, compounds are effective inhibitors of neurotransmitter release from ischemic neuronal cells.

In a further method aspect, this invention relates to a method of ameliorating the neurotoxic effect of ischemia, comprising administering to a subject, e.g., a human being exhibiting symptoms of or susceptible to such ischemia, a substituted guanidine, amino guanidine or N,N',N'',N'''-tetrasubstituted hydrazinedicarboximidamide of the invention, which inhibits the release of a neurotransmitter, in an amount effective to ameliorate the neurotoxic effect.

In another method aspect, the present invention relates to a method of treating Korsakoff's disease, a chronic alcoholism-induced condition, comprising administering to a mammal a substituted guanidine, amino guanidine or N,N',N'',N'''-tetrasubstituted hydrazinedicarboximidamide of the invention, in an amount effective to treat the disease. Pretreatment of animals with the substituted guanidines, amino guanidines and N,N',N'',N'''-tetrasubstituted hydrazinedicarboximidamides of the invention may markedly attenuate the extent of cell loss, hemorrhages and amino acid changes in a rat model of Korsakoff's disease. See Langlais, P. J. et al., *Soc. Neurosci. Abstr.* 14:774 (1988).

In another method aspect, the present invention relates to a method of treating or preventing HIV-induced dementia and blindness, comprising administering to a mammal a substituted guanidine, amino guanidine or N,N',N",N'''-tetrasubstituted hydrazinedicarboximidamide of the invention, in an amount effective to treat the disease. As disclosed by Dreyer et al., *Science* 248:364–367 (1990), gp120 neurotoxicity is associated with increased levels of $Ca^{2+}$ which are apparently mediated by excitatory amino acids binding at the NMDA receptor site. Therefore, the substituted guanidines, amino guanidines and N,N',N",N'''-tetrasubstituted hydrazinedicarboximidamides will find utility in treating or preventing HIV-induced dementia and blindness by preventing the release of excessive glutamate.

Figure 7:
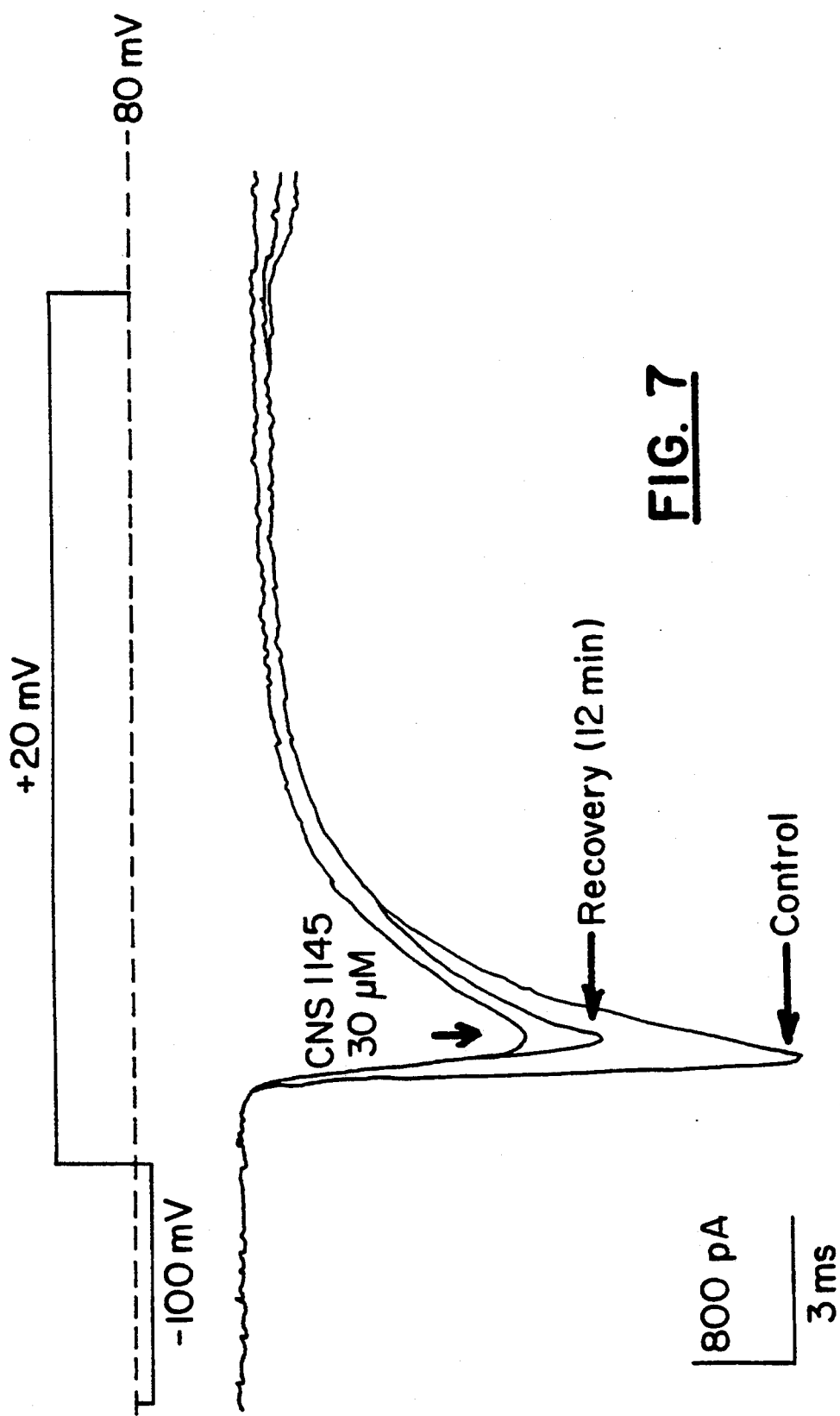
FIG. 7 depicts a graph showing the sodium channel blockade by N,N'-di(5-acenaphthyl)guanidine in N1E-115 cells, compared to control cells not treated with the drug. The stimulus protocol is shown on the top of the figure.

The substituted guanidines, amino guanidines and N,N',N",N'''-tetrasubstituted hydrazinedicarboximidamides will find utility in treating or preventing conditions treatable by the blockage of sodium ion channels, e.g. epilepsy. Although the mechanism of blockage of neurotransmitter release by PK 26124 is not yet clearly defined, this compound may antagonize not the presynaptic calcium channels but, instead, the sodium channels in or near the nerve terminals. See Hays, S. J. et al., Abstr. 201st Amer. Chem. Soc. Natl. Meeting, Med. Chem. Abstr. No. 14 (1991). In addition, certain antiepileptic agents, for example phenytoin (ibid; McLean and MacDonald, *J. Pharmacol. Exp. Ther.* 227:779 (1990)) and lamotrigine (Leach, M. J. et al., *Epilepsia* 27:490–497 (1986)) block sodium channels in a use-dependent fashion. Specifically, they inhibit the ability of neurons to sustain repetitive firing, and their maximum efficacy occurs under situations where bursts of sodium channel-mediated action potentials occur, such as in epilepsy. N,N'-di(5-acenaphthyl)guanidine is shown in FIG. 7 to block sodium channels, in addition to the presynaptic calcium channels. This dual action may be a desirable property of neuroprotective agents, as they may be more effective blockers of neurotransmitter release. Moreover, the use-dependence, ability to block release of glutamate and other neurotransmitters under conditions causing sustained depolarization of neurons and/or repetitive firing of action potentials, may be desirable properties of neuroprotective agents.

The invention also relates to the treatment of amnesia with the compounds of the invention. The glutamate release blocker riluzole has been shown to prevent memory loss in ischemic animals. Therefore, it is expected that the disubstituted guanidines, aminoguanidines, and N,N',N",N'''-tetrasubstituted hydrazinedicarboximidamides of the invention are also useful for treating or preventing memory loss.

The invention also relates to the treatment of migraine with the compounds of the invention. The calcium channel blocker disclosed in EP 0 266 574 reportedly is useful for the treatment of migraine. Therefore, it is expected that the disubstituted guanidines, aminoguanidines, and N,N',N",N'''-tetrasubstituted hydrazinedicarboximidamides of the invention are also useful for treating or preventing migraines.

The invention also relates to the treatment or prevention of multi-infarct dementia, a progressive deterioration of brain function and intellect due to multiple small strokes over time. The disubstituted guanidines, aminoguanidines, and N,N',N",N'''-tetrasubstituted hydrazinedicarboximidamides of the invention are expected to be useful in treating elderly patients who suffer from multi-infarct dementia as well as arteriosclerosis.

The methods of the present invention may be practiced on any animal, especially mammals and, more particularly, humans. However, it is intended that any animal which may experience benefit from administration of the disubstituted guanidines, aminoguanidines, and N,N',N",N'''-tetrasubstituted hydrazinedicarboximidamides of the invention are within the scope of animals which may be treated according to the invention.

The new drug screening method of the invention allows the identification of drugs which may be antagonists of the presynaptic calcium channel and which inhibit certain subcomponents of neurotransmitter release from neuronal tissue subject to ischemia.

Such compounds which inhibit neurotransmitter release can be determined by a method involving:
(a) contacting immobilized synaptosomes containing radiolabelled neurotransmitter with a compound suspected of inhibiting neurotransmitter release;
(b) inducing, by depolarization, the release of radiolabelled neurotransmitter from the immobilized radiolabelled synaptosomes obtained in step (a);
(c) washing the immobilized radiolabelled synaptosomes obtained in step (b) with a buffer comprising said compound and fractionating the effluent every 15 to 500 msec; and
(d) detecting the relative amount of radiolabelled neurotransmitter in each fraction compared to control synaptosomes which have not been exposed to the compound of interest;

wherein a reduced amount of released radiolabelled neurotransmitter in the fractions from synaptosomes treated with the compound relative to control synaptosomes indicates that the compound inhibits neurotransmitter release.

This drug screening method requires that the entrapped synaptosomes be housed in a superfusion chamber having a very small dead volume to allow subsecond time resolution. Such superfusion chambers are taught, for example, in U.S. Pat. No. 4,891,185 and by Turner, T. J. et al., *Anal. Biochem.* 178:8–16 (1989), the disclosures of which are fully incorporated by reference herein.

This method also allows for the screening of drugs which selectively inhibit a $Ca^{2+}$-dependent or $Ca^{2+}$-independent subcomponent of neurotransmitter release. As shown in FIG. 1, there are both phasic and tonic components of glutamate release in the presence of $Ca^{2+}$ and a $Ca^{2+}$-independent component which can be seen in the absence of $Ca^{2+}$. Preferably, drugs are identified which selectively inhibit the $Ca^{2+}$-dependent tonic component of glutamate release. Such drugs may be identified by running the assay in the presence of $Ca^{2+}$ and the drug in question. Preferably, the concentration of $Ca^{2+}$ is about $>50$ $\mu$M. More preferably, the concentration of $Ca^{2+}$ is about 2 mM. The selective inhibition of the tonic component of neurotransmitter release indicates that the drug may be particularly effective in preventing neuronal loss due to ischemia and in treating other pathophysiologic conditions which are the consequence of elevated levels of release of neurotransmitters such as glutamate.

Figure 2:
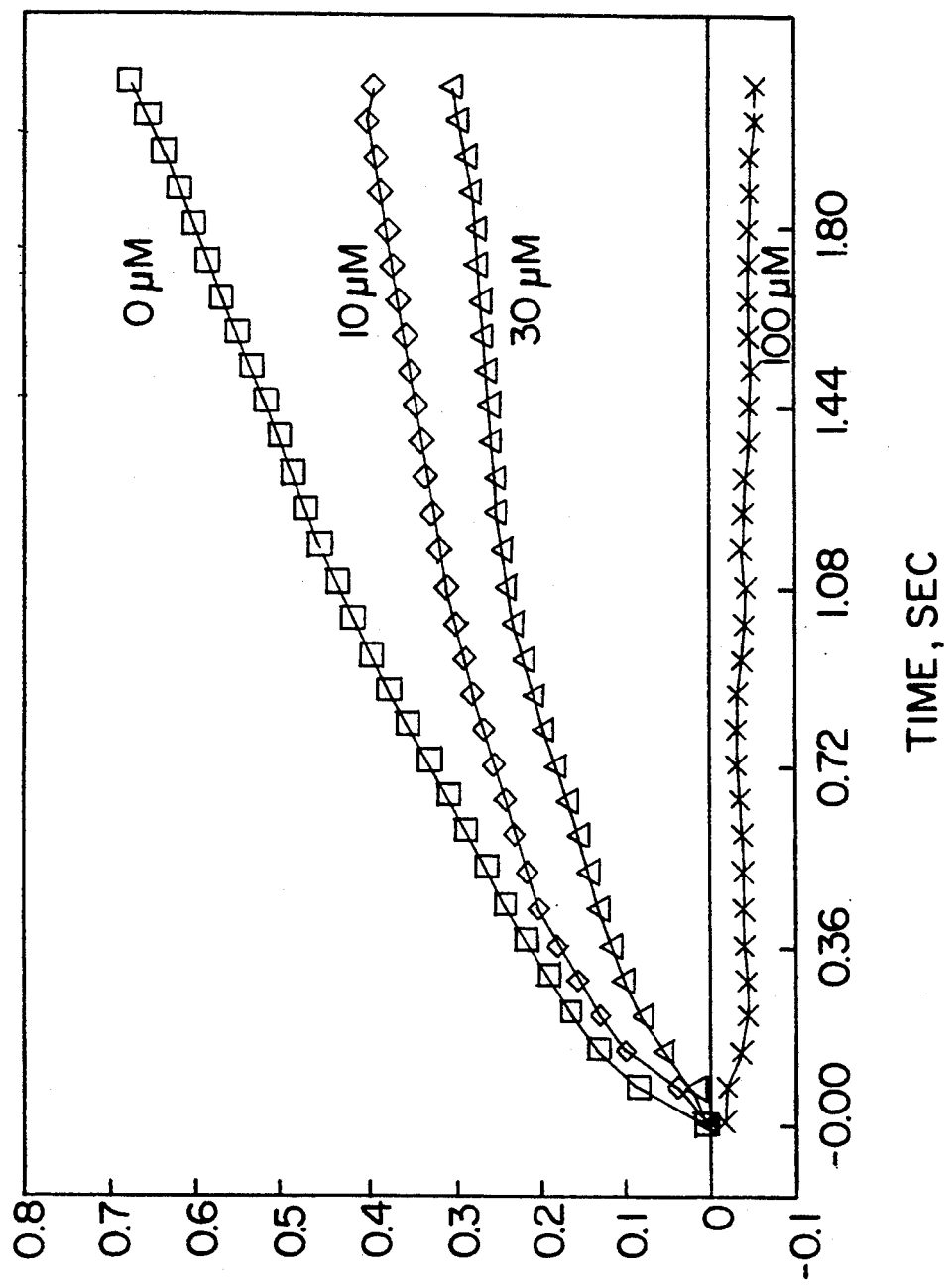
FIG. 2 depicts a graph showing the effect of 0 $\mu M$, 10 $\mu M$, 30 $\mu M$, and 100 $\mu M$ N,N'-di-(adamantan-1-yl)guanidine on the $Ca^{2+}$-dependent $^3H$ glutamate release from rat brain synaptosomes.

Preferably, the synaptosomes are immobilized. Methods for preparing immobilized cells are taught, for example, in U.S. Pat. Nos. 4,390,627, 4,212,943, and 4,337,313, the disclosures of which are fully incorporated by reference herein. Most preferably, the synaptosomes are entrapped in a filter matrix, as more fully described below, in a housing with a very small dead volume, and a physiologic buffer is passed therethrough. The effluent is then fractionated over very short periods of time (15 to 500 msec) and the relative amounts of radiolabelled neurotransmitter (preferably glutamate) in each fraction is determined. A plot of the amount of radiolabelled glutamate over time gives a measure of the ability of the compound to inhibit neurotransmitter release. An example of such a plot is shown in FIG. 2.

A more detailed, but not limiting, protocol is as follows:
  (a) contacting brain synaptosomes with radiolabelled glutamate for a time sufficient to allow uptake of the radiolabelled glutamate via the Na-dependent glutamate uptake system, to give radiolabelled synaptosomes;
  (b) preparing a suspension of the radiolabelled synaptosomes obtained in step (a) in a physiologic buffer and passing the suspension through a filter matrix to entrap the radiolabelled synaptosomes;
  (c) washing the entrapped radiolabelled synaptosomes obtained in step (b) with a physiologic buffer;
  (d) contacting the entrapped radiolabelled synaptosomes obtained in step (c) with a compound suspected of being an inhibitor of glutamate release;
  (e) depolarizing the membranes of the entrapped radiolabelled synaptosomes obtained in step (d);
  (f) washing the entrapped radiolabelled synaptosomes obtained in step (e) with a physiologic buffer comprising the organic compound of interest and fractionating the effluent every 15 to 500 msec; and
  (g) detecting the relative amount of radiolabelled glutamate in each fraction compared to control effluent which has not been exposed to the compound of interest.

Where there is a reduced amount of radiolabelled glutamate in the effluent fractions of synaptosomes treated with the compound relative to control synaptosomes, the compound is an inhibitor of glutamate release. As discussed above, the assay may be conducted in the presence and absence of $Ca^{2+}$, and the kinetics of the Ca-dependent component of neurotransmitter release may be analyzed to determine the effect of the compound on the three subcomponents of glutamate release.

In the above method, synaptosomes are isolated and radioisotopically labeled with radiolabelled neurotransmitter. The radiolabelled synaptosomes are then entrapped in a filter matrix and allowed to equilibrate with a physiologic buffer solution that flows into the sample chamber through a valve. This valve is then closed simultaneously with the opening of a second valve allowing a physiologic solution comprising the organic test compound to flow through the filter matrix and contact the entrapped synaptosomes. The second valve is then closed simultaneously with the opening of a third valve comprising a substance, with or without $Ca^{2+}$, which causes depolarization of the synaptosome membranes, together with the organic test compound. The third valve is then closed simultaneously with the opening of the second valve. During the entire superfusion period, the effluent comprising each physiologic buffer, test compound and radiolabelled glutamate is continuously fractionated. This method allows for the rapid kinetic measurement of radiolabelled glutamate release from synaptosomes. Optionally, one or more of the test solutions comprising >50 $\mu$M $Ca^{2+}$ may be delivered through the third valve.

The synaptosomes may be derived from any animal, including the rat. They may be isolated according to Example 3, herein, or according to Gray and Whittaker, *J. Anat.* 96:79-88 (1962); or Suszkiw et al., *J. Neurosci.* 6:1349-1357 (1986).

Any radiolabelled form of the neurotransmitter may be used in the practice of the screening assay including $^3H$ and $^{14}C$ labelled neurotransmitter. Both $^3H$ and $^{14}C$ labelled glutamate are commercially available.

The entrapped synaptosomes are contacted with the radiolabelled neurotransmitter for a time sufficient to allow uptake of the radiolabelled neurotransmitter by the synaptosomes. A preferred time is about 10 minutes.

The physiologic buffer may be any buffer known to those of ordinary skill in the art which is compatible with synaptosomes. See Example 3 (basal buffer); Gray and Whittaker, *J. Anat.* 96:79-88 (1962); or Suszkiw et al., *J. Neurosci.* 6:1349-1357 (1986).

Filters which may be used to entrap the synaptosomes are matrices of randomly-oriented fibers or beads pressed, wound, or otherwise bonded together into a tortuous maze of flow channels (definition obtained from Millipore Corp. Catalogue and Purchasing Guide, Lit. No. PA085, printed 9/85). A depth filter is capable of trapping the substrate in a three dimensional matrix thereby allowing a maximum amount of synaptosomes to be loaded onto the filter without causing a blockage (clogging) of the solution flow. The preferred depth filters are glass fiber filters such as Whatman GF/F filters; ceramic filters can also be used. Glass fiber filters are particularly desirable because of their flexibility, chemical inertness, and low cost. A Millipore SC filter may be used to maintain the integrity of glass fiber filters. See Turner, T. J. et al., *Anal. Biochem.* 178:8-16 (1989), incorporated by reference herein, for a detailed description of the superfusion system and the filter configuration for entrapping synaptosomes.

The concentration of test organic compound in the physiologic buffer may range from 0 to about 1 mM, more preferably, from 0 to about 100 $\mu$M. If the guanidine is not soluble in the physiologic buffer, then an equivalent amount of a soluble pharmacologically acceptable salt of the organic compound, as disclosed herein, may be utilized. Alternatively, the compounds may be diluted from a suitable organic solvent.

The flow rates of the physiologic solutions and test solutions should be at least 0.1 ml/sec. Preferably, the flow rate is about 1.0 ml/sec.

Induction of the neurotransmitter release may be accomplished by depolarizing the synaptosome membranes by contact with relatively high concentrations of cations such as $K^+$ or by the application of a voltage across the synaptosomes. Alternatively, the release of the neurotransmitter may be induced by contacting the synaptosomes with veratramine. The concentration of $K^+$ necessary to cause depolarization may range from about 10 to about 150 mM. A preferred concentration is about 110 mM (as KCl). The corresponding transmembrane voltage necessary to cause depolarization may range from about $-40$ mV to about 60 mV.

The effluent fractions may be collected using any means which allow the collection of fractions over periods of time as short as about 15 msec. The fractions may be collected in a series of separate tube or may be continuously applied to an absorbent substrate such as filter paper. Preferably, the fractions are obtained and collected with the superfusion instrument described in the present Examples and disclosed in U.S. Pat. No. 4,891,185, the content of which is fully incorporated by reference herein. In general, the effluent is collected in vials positioned as a spiral or a circle on a turntable which rotates at 16, 33, 45 and 78 rpm, giving 3.75, 1.82, 1.33 and 0.77 seconds per rotation. Fifty collection vials in each single revolution allows for the collection of fractions for as long as 66 msec. or as short as 15 msec.

The compounds of this invention can be administered intranasally, orally or by injection, e.g., intramuscular, intraperitoneal or intravenous injection or by transdermal, intraocular or enteral means. The optimal dose can be determined by conventional means. Because many of the substituted guanidines employed in this invention are substantially water insoluble, they are ordinarily administered in the protonated form, e.g., as a pharmaceutically acceptable salt of an organic or inorganic acid, e.g., hydrochloride, sulfate, hemisulfate, phosphate, nitrate, acetate, oxalate, citrate, malate, etc.

The compounds of this invention can be employed in mixture with conventional excipients, i.e., pharmaceutically acceptable organic or inorganic carrier substances suitable for parenteral, enteral or intranasal application which do not deleteriously react to the active compounds. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or a carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Intravenous or parenteral administration, e.g., subcutaneous, intraperitoneal, or intramuscular are preferred. The compounds of this invention being particularly valuable in the treatment of mammalian subjects, e.g., humans. Typically, such subjects include those suffering from or likely to suffer from nervous system dysfunctions resulting from, for example, epilepsy or nerve cell degeneration which is the result of hypoxia, hypoglycemia, brain or spinal chord trauma, or brain or spinal chord ischemia. Typical candidates for treatment include heart attack, stroke, brain or spinal cord injury patients, patients undergoing major surgery where brain ischemia is a potential complication, patients [divers] suffering from decompression sickness due to gas emboli in the blood stream, drowning victims, and patients suffering from carbon monoxide poisoning, cyanide poisoning, and toxic brain damage from ingestion of tetrodotoxin or shellfish toxin. Other candidates include patients suffering from amnesia, migraine, and multi-infarct dementia. Other candidates for treatment include those patients afflicted with neurodegenerative diseases such as Huntington's disease, Amyotrophic Lateral Sclerosis, Alzheimer's disease, Down's Syndrome olivopontocerebellar atrophy, and Korsakoff's disease. In addition, HIV-infected individuals may be treated with the substituted guanidines, amino guanidines and N,N',N", N'"-tetrasubstituted hydrazinedicarboximidamides of the invention to treat or prevent blindness and HIV-associated dementia. Moveover, the substituted guanidines, amino guanidines and N,N',N", N'"-tetrasubstituted hydrazinedicarboximidamides of the invention may be administered to those patients who are susceptible to generalized anxiety disorder (GAD) in order to treat or prevent anxiety.

The compounds of the invention may also be employed in cryopreservation solutions for tissues, organs and animals. The compounds of the invention in such solutions may be effective for reducing the amount of neuronal loss associated with the freezing of tissues, organs and animals.

It will be appreciated that the actually preferred amounts of active compounds used will vary according to the specific compound being utilized, the particular compositions formulated, the mode of application and the particular site of administration. Optimal administration rates for a given protocol of administration can be readily ascertained by those skilled in the art using conventional dosage determination tests conducted with regard to the foregoing guidelines.

Like the guanidines of U.S. Pat. Nos. 1,411,713, 1,422,506 and 1,597,233, the substituted guanidines and related compounds of the present invention may also be used as rubber accelerators.

The invention also relates to radiolabeled derivates of the guanidines and related compounds of the present invention. Preferably, the radiolabel is $^3$H, $^{11}$C, $^{14}$C, $^{18}$F, $^{125}$I, $^{131}$I, $^{15}$N, $^{35}$S or $^{32}$P. These radiolabeled compounds may be used to study the receptors responsible for their pharmacologic activity as well as for imaging of tissue samples for the distribution of receptors for these compounds.

The invention also relates to the compounds of the invention in the form of pharmaceutically acceptable salts, e.g. salts with pharmaceutically acceptable acids such as hydrochloric, sulfuric, acetic, malic, phosphoric or succinic acid, etc.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire text of all applications, patents and publications cited above and below are hereby incorporated by reference.

EXAMPLES

Example 1

Synthesis of N,N'-(Adamantan-2-yl)guanidine Hydrochloride

2-Adamantylcyanamide

2-Adamantanamine hydrochloride (25 g, 133.2 mmol, Aldrich) was partitioned between 200 mL of toluene and 200 mL of 1N NaOH and the mixture stirred for 30 minutes. The layers were separated and the aqueous layer extracted with toluene (75 mL). The combined organic layers were washed with water (100 mL), dried (MgSO$_4$) and the resultant filtrate utilized as is (the amount of 2adamantanamine was assumed to be 133 mmol). To this ice cold solution was added dropwise with stirring a solution of cyanogen bromide (8.74 g, 82.5 mmol) in 25 mL of toluene. As the addition proceeded, a precipitate formed. After the addition of the cyanogen bromide was completed, the reaction mixture was allowed to warm to room temperature and stir for an additional two hours. The precipitate was filtered off and the filtrate concentrated in vacuo to afford 10 g of a light yellow solid. The crude product was recrystallized (methanol/water) and the product dried in vacuo (1 torr, over P$_2$O$_5$/KOH) to give 9.04 g (62% yield) of the desired product.

N,N'-(Adamantan-2-yl)guanidine Hydrochloride

A mixture of 2-adamantylcyanamide (3.4 g, 19.35 mmol) and 2-adamantanamide hydrochloride (2.9 g, 15.48 mmol) was heated in an oil bath at 205° C. under an atmosphere of argon. The mixture gradually fused to a semisolid residue (but never yielded a clear melt) and then solidified. The reaction mixture was allowed to cool and methanol (30 mL) and water (30 mL) were then added to the solid. The mixture was filtered and the solid obtained warmed with methanol (150 mL) and the insoluble material removed by gravity filtration. The filtrate was clarified with activated charcoal and concentrated in vacuo to afford a white solid. This material was dissolved in 150 mL of boiling ethanol and the resultant solution concentrated over a hot plate to give 60 mL. On cooling, crystallization occurred to give 3 g of product which was again recrystallized, but this time from ethanol and water, to give (after drying in vacuo over P$_2$O$_5$ at 65° C. for 24 hrs) 2.92 g of N,N'-(Adamantan-2-yl)guanidine Hydrochloride. M.p.>340° C. Anal. calcd. for C$_{21}$H$_{34}$N$_3$Cl: C, 67.08; H, 9.11; N, 11.18. Found C, 67.21; H, 9.26; N, 11.34.

Example 2

Synthesis of N,N'N'',N'''-tetracyclohexylhydrazinedicarboximidamide

DCC (1.03 g, 4.97 mmol) was dissolved in tetrahydrofuran (15 mL). Hydrazine (135 mg, 4.22 mmol) was added via syringe. Stirring 30 hours at room temperature produced a clear yellow mixture which was evaporated to a white powder (922 mg). Solution of this powder in diethyl ether, filtration and acidification with HCl (60 mL of saturated Et$_2$O) gave a yellow white precipitate (856 mg). Two recrystallizations (EtOH in an Et$_2$O chamber) gave white prisms (133 mg, 18% M.P. 288°–290° C.). The low percentage of nitrogen in the elemental analysis of this compound indicates that two equivalents of DCC have reacted to hydrazine, forming the title compound. $^1$H NMR ([$^2$H]—CH$_3$OH) δ3.21 (s, 4, N-bearing cyclohexyl), 2.0–1.5 (m, 44, cyclohexyls). $^{13}$C NMR ([$^2$H]—CH$_3$OH) δ154.1 (guanidine), 51.7 (N-bearing cyclohexyl), 32.4 and 24.8 (cyclohexyls). IR shows peaks at 1639 and 1589 cm$^{-1}$. Elem. Analysis (C$_{26}$N$_6$H$_{50}$Cl$_2$:½ H$_2$O). Theor. C 59.30, H 9.76, N 15.96. Found C 58.94, H 9.76, N 16.01.

Example 3

Synthesis of N,N'-Bis(5-acenaphthyl)guanidine hydrobromide

5-Aminoacenaphthene 40 gms (Aldrich lot #CY 02301 HX, containing 15% of the 3-nitro isomer) of 5-nitroacenaphthene was dissolved in a mixture of tetrahydrofuran (150 ml) and acetic acid (25 ml.). To this solution was added 1.0 of 10% Pd/C and the mixture hydrogenated (40 psi) at room temperature. After 2 hours, the mixture was filtered through a bed of celite and the filtrate concentrated in vacuo to give a mixture of a solid which darkened (to purple) considerably on exposure to air. This material was redissolved in methylene chloride and decolorized with activated charcoal and then the product recrystallized from a mixture of cyclohexane:ethyl acetate (3:1) to give 8.3 g of clean material—only the major 5-amino isomer being present by TLC. This material was used as is directly in the next step.

N,N'-Bis(5-acenaphthyl)guanidine hydrobromide:

To a stirred solution of 5-aminoacenaphthene (8.1 g, 49 mmol) in ethanol (35 ml) was added, dropwise with stirring, a solution of cyanogen bromide (2.6 g, 24.5 mmol) in ethanol (25 ml). The mixture was then refluxed for 6 h and allowed to stand for 48 h for convenience. The crystals were collected by filtration and washed with a little ethanol and then ether to give 7.7 g of crude product. This material was combined with a smaller 1.1 g lot and the total amount dissolved in boiling ethanol (approximately 1 L) and decolorized with activated charcoal. The charcoal was removed by gravity filtration and the filtrate concentrated over a hot plate to 200 mL. On cooling, off white crystals were deposited which were dried in vacuo at 100° C. under 1 torr, to give 5.9 gms; mp 288°–290° C.

Anal. Calcd. for C$_{25}$H$_{22}$N$_3$Br(444.35); C, 67.56; H, 4.99; N, 9.46. Found: C, 67.46; H, 5.06; N, 9.21.

HPLC (reverse phase): MeCN/H$_2$O (50:50 with 0.1% TFA), single component Rt=12.91 minutes.

Example 4

Synthesis of N,N'-Bis(3-acenaphthyl)guanidine hydrobromide

3-Aminoacenaphthene

A 25 g sample of commercial 5-nitroacenaphthene (containing 15% of the 3-nitro isomer) was chromatographed (600 g silica gel, 230–400 mesh, hexane/ethyl acetate (10:1)) to give 400 mg of the 3-nitro isomer. The remainder of the fractions were a mixture of both isomers and this method was abandoned as a method to separate the two isomers. The 400 mg sample was hydrogenated (40 PSI, 10% Pd/C, 5% acetic acid in THF) on a Parr apparatus to give the amino compound which solidified after removal of the solvent in vacuo. This material was used directly, in the next step.

N,N'-Bis(3-acenaphthyl)guanidine Hydrobromide:

To a solution of 3-aminoacenaphthene in 15 mL of absolute ethanol was added 85 mg of cyanogen bromide. The solution was heated at reflux, under an nitrogen atmosphere, for 11 hours. The solution was concentrated in vacuo to ~8 mL and the mixture cooled in an ice bath to give 120 mg of crude product. This material was recrystallized from ethanol to give 60 mg of product, mp 291°–293° C. The HPLC of this material showed the presence of a single impurity (15%). Therefore, this material was partitioned between a 10% aqueous solution of sodium bicarbonate and ethyl acetate, with the intention of converting it to the free base and then running a prep TLC. However, a good portion of the material formed an emulsion in the organic layer. This solid was collected by filtration and turned out to be free of the impurity. It was redissolved in 0.7M HCl in methanol and concentrated in vacuo to afford a cream white solid; wt 20 mg; mp 210(s)–230° C. (slow dec). This step should probably have been omitted, since it is hard to predict if the material is a hydrochloride or hydrobromide. Since we have such a small quantity of material, and it is clean by TLC and HPLC we made no attempt to carry out an elemental analysis.

HPLC: C18 Reverse phase, MeCN: $H_2O$ 50:50 with 0.1% TFA, Rt=16.7 min (98.85%), impurities at 4.62 min (0.625%) and 15.83 min (0.517%).

Example 5

Synthesis of N-(3- and 5-Acenaphthyl)-N'-(4-isopropylphenyl)-guanidine.HCl

A mixture of 3- and 5-nitroacenaphthene (5 g) was dissolved in EtOAc and placed into a hydrogenating flask containing Palladium on activated carbon (10%, 0.5 g). The reaction mixture was hydrogenated at 40 psi for 1.5 hr. The pressure of hydrogen dropped due to the consuming of the hydrogen, and it was brought back to 50 psi a few times during the reaction. When all the starting material was used, the hydrogen was released and the resulting solution was filtered through a pad of celite and washed with EtOAc (20 mL). The clear filtrate was concentrated and dried under vacuum to yield a mixture of 3- and 5aminoacenaphthene as a brown solid (4.2 g, 100% yield).

TLC ($SiO_2$, $CH_2Cl_2$): $R_f$ 0.2.

3- and 5-aminoacenaphthene.HCl

Mixture of 3- and 5-aminoacenaphthene (0.8 g) in MeOH (40 mL) was treated with HCl/MeOH (0.5 M, 20 mL), and the reaction mixture was stirred at room temperature for 30 min. Then the solution was concentrated and dried under vacuum to yield a mixture of 3- and 5-aminoacenaphthene.HCl as a gray solid.

Isopropylphenyl Cyanamide

A solution of cyanogen bromide (1.59 g, 15 mmol) in diethylether (20) was added dropwise to a solution of 4-isopropylaniline (3.24 g) in diethylether (50 mL) at 4° C. with stirring. After the addition, the reaction mixture was kept stirring at room temperature for 18 h. Then a solution with white precipitates formed and the precipitates were removed by filtration. The etherate solution was washed with aqueous HCl (1N, 30 mL, two times) as well as brine, dried over $MgSO_4$, filtered, concentrated, and dried under vacuum to yield 4-isopropylphenyl cyanamide (2.0 g, 84%).

TLC ($SiO_2$, $CH_2CL_2$): $R_f$ 0.2
IR($CH_2CL_2$): 2220 $cm^{-1}$.

Synthesis of Di-(3- and 5-Acenaphthyl)-N'-(4-isopropylphenyl)-guanidine.HCl

A stirred solution of 4-isopropylphenyl cyanamide (160 mg) in chlorobenzene (35 mL) as added a mixture of 3- and 5-aminoacenaphthene.HCl (230 mg, 1 mmol) at 25° C. under Argon. The reaction mixture was heated at 150° C. in an oil bath for 20 hr. A homogenous solution was obtained and this solution was concentrated to dryness by rotavap. The obtained product was further purified by prep. TLC to yield N-(3- and 5-Acenaphthyl)-N'-(4-isopropylphenyl)-guanidine.HCl as a light brown solid (0.28 g, 71% yield).

TLC ($SiO_2$, $CH_2CL_2$/MeOH=9/1): $R_f$=0.36
IR($CH_2CL_2$): 1660 $cm^{-1}$ (guanidine peak).
$^1H$ NMR($CD_3OD$) ppm: 1.07 (d, J=8.57 Hz, 6H), 2.76 (m, 1H), 3.24 (m, 4H), 7.08–7.52 (m, 9H).
$^{13}C$ NMR($CD_3OD$) ppm: 24.30, 30.94, 31.54, 35.01, 118.48, 120.35, 121.35, 126.45, 126.86, 127.61, 128.38, 128.98, 129.53, 130.24, 133.85, 141.63, 147.99, 148.76, 149.68, 149.87, 157.30.

High Resolution Mass Spec: $C_{22}H_{23}N_3$ 329.1892 (Calc.), 329.1889 (Exp.).

Example 6

Synthesis of N-(3- and 5-Acenaphthyl)-N-(4-fluoronaphthyl)-guanidine.HCl 3- and 5-Acenaphthyl cyanamide A solution of cyanogen bromide in $CH_3CN$ (5M, 5.1 mL, 25.6 mmol) was added slowly into a stirred solution of 3- and 5-aminoacenaphthene (41 mmol) in diethylether (65 mL) and EtOAc (10 mL) at 0° C. After the addition, the reaction mixture was stirred at room temperature for 23 h. Finally, the reaction mixture became a green solution with gray precipitates; the precipitates were removed by filtration. The green filtrate was further washed by aqueous HCl (1N, three times), water (100 mL), and brine (200 mL). Then the solution was dried over $MgSO_4$, filtered, concentrated, and dried under vacuum to yield 3- and 5-acenaphthyl cyanamide. The product was a brown solid (3.64 g; 92% in yield).

TLC ($SiO_2$, $CH_2Cl_2$/MeOH=9/1): $R_f$=0.67.

4-Fluoro-1-aminoaphthalene

4-Fluoro-1-nitro-naphthalene (1 g) was dissolved in EtOAc (20 mL) and placed into a hydrogenating flask containing Palladium on activated charcoal (10%, 0.3 g). The reaction mixture was hydrogenated at 50 psi for 5 hr. During the reaction, the pressure of the hydrogen dropped due to the consuming of the hydrogen, and it was brought back to 50 psi a few times. Finally, the reaction stopped when all the starting material was used. The resulting solution was filtered through a pad of celite and washed with EtOAc (20 mL). The clear filtrate was concentrated and dried under vacuum to yield 4-Fluoro-1-aminonaphthalene.

TLC ($SiO_2$, $CH_2Cl_2$): $R_f$=0.33.

4-Fluoro-1-aminoaphthalene.HCl

To 4-fluoro-1-aminoaphthalene in MeOH (5 mL) was added HCl/MeOH (0.5M, 20 mL), then the reaction mixture was stirred at room temperature for 30 min. A white precipitate formed during the reaction; the precipitate was collected by filtration and dried under vacuum to yield 4-fluoro-1-aminoaphthalene.HCl as a white solid (0.81 g; 80% yield).

N-(3- and 5-Acenaphthyl)-N'-(4-fluoronaphthyl)guanidine.HCl

A mixture of 3- and 5-acenaphthyl cyanamide (516 mg, 2.66 mmol) and 4-fluoro-1-aminonaphthalene.HCl (500 mg, 2.53 mmol) in chlorobenzene (15 mL was heated to 150° C. for 24 hr with stirring. After the reaction mixture was cooled to room temperature, diethylether (50 mL) was added and a white precipitate formed. The precipitate was collected by filtration, redissolved in methanol, treated with Norit for 30 min, filtered and concentrated to yield the crude product. The crude product was further recrystallized in EtOH/Et$_2$O to yield pure (N-(3- and 5-acenaphthyl)-N'-(4fluoronaphthyl)guanidine.HCl (0.52 g, 53% yield).

TLC (SiO$_2$, CH$_2$Cl$_2$/MeOH=9/1): R$_f$=0.37

$^1$H NMR (CD$_3$OD) ppm: 3.33–3.38 (m, 4H), 7.22–8.10 (m, 11H).

$^{13}$C NMR (CD$_3$OD) ppm: 30.97, 31.55, 110.64, 118.41, 120.39, 121.45, 122.09, 123.38, 125.84, 127.23, 127.68, 128.02, 128.44, 128.97, 129.56, 129.84, 130.37, 133.18, 141.67, 148.09, 149.19, 158.43, 160.13 (d, j=253.4 Hz).

High Resolution Mass Spec: C$_{23}$H$_{18}$N$_3$F 355.1484 (Cacl.), 355.1479 (Exp.).

Example 7

Synthesis of N-(3- and 4-Acenaphthyl)-N-(4-methoxynaphthyl)guanidine.HCl

4-Methoxy-1-aminonaphthalene

A mixture of 4-methoxy-1-nitro-naphthalene (2 g, 9.84 mmol) was dissolved in EtOAc (100 mL) and placed into a hydrogenating flask containing Palladium on activated carbon (10%, 0.2 g). The reaction mixture was hydrogenated at 50 psi for 1.5 hr. During the reaction, the pressure of the hydrogen dropped a few times due to the consuming of the hydrogen, and the pressure was brought back to 50 psi. When the starting material was used, the reaction was stopped and the hydrogen was released. The resulting solution was filtered through a pad of celite and washed with EtOAc (20 mL). The clear filtrate was concentrated and dried under vacuum to yield 4-Fluoro-1-aminonophthalene (100% yield).

TLC (SiO$_2$, CH$_2$Cl$_2$): R$_f$=0.24

4-Methoxy-1-aminonaphthalene.HCl

4-Methoxy-1-aminonaphthalene (0.53 g, 3.1 mmol) was dissolved in HCl/MeOH (0.5M, 15 mL), then the reaction mixture was stirred at room temperature for 60 min. The reaction mixture was concentrated to dryness to yield the crude product as a solid. The solid was further washed by EtOAc, collected by filtration, and dried under vacuum to yield 4-methoxy-1-aminonaphthalene.HCl as a white solid (0.61 g; yield: 96%).

N-(3- and 5-Acenaphthyl)-N'-(4-methoxynaphthyl)guanidine.HCl

Mixture of 3- and 5-acenaphthyl cyanamide (243 mg, 1.25 mmol and 4-methoxy-1-aminonaphthalene.HCl (250 mg, 1.19 mmol) in chlorobenzene was heated to 150° C. for 7 hr with stirring. After the reaction mixture was cooled to room temperature, it became a mixture of a brown solution and white precipitates. The precipitates were collected by filtration, washed thoroughly with CH$_2$Cl$_2$ (30 mL) as well as EtOAc (15 mL), and dried under vacuum to yield N-(3- and 5-acenaphthyl)-N'-(4-methoxynaphthyl)guanidine.HCl (0.41 g, 86% yield) as a white powder.

TLC (SiO$_2$, CH$_2$Cl$_2$/MeOH=9/1): R$_f$=0.33

$^1$H NMR (CD$_3$OD) ppm: 3.32–3.36 (m, 4H), 3.96 (s, 3H), 6.89–8.24 (m, 11H).

$^{13}$C NMR (CD$_3$OD) ppm: 30.96, 31.55, 104.76, 118.44, 120.37, 121.42, 122.79, 123.64, 123.82, 123.86, 127.08, 127.31, 127.77, 128.32, 128.87, 128.98, 130.06, 132.62, 141.67, 148.07, 149.13, 157.62, 158.57.

High Resolution Mass: C$_{24}$H$_{21}$N$_3$O 367.1685 (Cacl.), 367.1686 (Exp.).

Example 8

Basic Protocol for the Preparation of Synaptosomes and Superfusion

Solutions:
0.32M sucrose solution
0.80M sucrose solution

| Basal buffer is of the following composition: | |
| --- | --- |
| NaCl | 147 mM |
| KCl | 3 mM |
| HEPES | 10 mM |
| Dextrose | 10 mM |
| MgCl$_2$ | 1.2 mM |
| EGTA-TRIS | 1 mM |
| pH | 7.4 |
| High-K$^+$ buffer | |
| NaCl | 95 mM |
| KCl | 55 mM |

The rest of the components in high-K$^+$ buffer are of the same composition as Basal buffer. For studying total $^3$H-glutamate release, Ca$^{+2}$ is added to the high-K$^+$ buffer at 2.4 mM.

To study the release of presynaptic $^3$H-glutamate, synaptosomes from young rats were used. CD Male rats of 4 to 6 weeks (50–75 g) were used for the preparation of synaptosomes. Rats were killed by decapitation with guillotine and the skull bone was opened in the center with the pointed blade of dissection scissors. The bone is then peeled away with a bone cutter and the brain is pried with a micro spatula. The cerebellum is removed and the rest of the brain is placed in 35 ml of 0.32M Sucrose solution and homogenized in a Thomas glass teflon homogenizer C at the maximum power setting (about 450 rpm) with 16 strokes. The pestle is rinsed with 5 ml of sucrose solution and added to the homogenate. The homogenate is centrifuged for 10 min at 3500 rpm (1500 g) in a SS-34 rotor in Sorvall RC-5B. The resulting pellet (P$_1$) is discarded and the supernatant (S$_1$) is recentrifuged for 20 min at 8700 rpm (8500 g). The supernatant (S$_2$) is discarded and the pellet (P$_2$) is resuspended in 5 ml of 0.32M sucrose and hand homogenized with 4 strokes (Thomas C) and the volume was made up to 8 ml. This homogenate was layered on 20 ml of 0.8M sucrose solution in two centrifuge tubes and spun for 25 minutes at 8700 rpm (8500 g). At the end of this spin, most of the myelin stays at the interphase of 0.32M and 0.8M sucrose and mitochondria pellet as a brown pellet. The synaptosomes are dispersed in the 0.8M sucrose. Using a 10 ml pipette, the 0.8M sucrose layer is collected (without disturbing the top myelin layer or the pellet) and diluted slowly with an equal volume of chilled basal buffer, while stirring gently with a Pasteur pipette. This diluted solution is centrifuged for 10 min at 10,000 rpm (12,000 g) and the pellet is resuspended in 1.5 ml of basal buffer and hand-homogenized in a Wheaton glass-glass 7 ml homogenizer with 8 strokes.

DILUTION OF SYNAPTOSOME PREP FOR SUPERFUSION

The synaptosomal homogenate is diluted 1 ml to 10 ml with basal buffer. This dilution gives a protein concentration of 500 to 600 μg/ml. One hundred μl of this diluted prep with 50–60 μg of protein is used for each superfusion event. This amount of protein is found to be optimum for a rapid washout of released tracer. The diluted synaptosomal solution was kept on ice until the end of the experiment.

LOADING SYNAPTOSOMES WITH $^3$H-GLUTAMATE $^3$H-glutamate (purchased from NEN) is stored in the refrigerator. Pipette 6 μl (6 Ci; 40 to 55 Ci/mmol) into a disposable test tube. Add 100 μl of diluted prep and mix gently on vortex and incubate at 30° C. for 10 min. $^3$H-glutamate is taken up by sodium-coupled glutamate transporter present in synaptosomal membranes. After 10 min, dilute the incubation mixture with 690 μl of basal buffer. This solution is then transferred in Tygon tubing that is connected to the synaptosome loading chamber. Using a syringe filler with air, the solution is forced through the Millipore SC-GF/F-Millipore SC filter sandwich. These filters retain the synaptosomes and the solution flows through.

LOADING CHAMBER

The loading chamber is assembled from a "General Valve" tube-tube connector. One end is connected to a barbed fitting which in turn is connected to a 12 gm Tygon tube and serves as inlet to the chamber. On the other end of the connector is attached to the filter assembly. The filter assembly consists of a stainless steel washer with a flat side facing the filter, a SC Millipore filter, GF/F Whatman glass fiver filter disc with grid facing into the flow, another SC filter followed by a stainless steel screen and a stainless steel washer with the flat side facing the screen. This whole assembly is secured with a teflon nut. After the synaptosomes are loaded, by unscrewing the nut and tapping it to the workbench, the filter sandwich can be dislodged.

SUPERFUSION

An important component of the superfusion setup is the custom made stainless steel "General Valve" three-valve solenoid operated superfusion chamber with an outlet for the effluent. The three inlets are connected to stainless steel buffer reservoirs that contain (1) wash buffer, (2) control buffer and (3) experimental buffer which are kept under 40 psi of nitrogen gas through teflon tubing connections. The superfusion is controlled through a menu-driven program on an Apple IIe computer. See Turner, J. T. et al., *Anal. Biochem.* 178:8–16 (1989), and U.S. Pat. No. 4,891,185, the disclosures of which are fully incorporated by reference herein.

The superfusion chamber has a teflon bushing and a stainless steel washer fixed with the flat surface facing the filters. A GF/B filter disc is placed first in the chamber to eliminate the switching related artifacts. The synaptosome loaded sandwich is then placed facing the synaptosomes into the flow followed by RA filter, stainless steel screen and a washer with the flat side facing the screen. This assembly is secured with a teflon nut that has two layers of teflon tubing fixed inside with epoxy to reduce the dead volume and improve the effluent flow.

The time protocol can be varied as for the requirements of the particular experiment. Before superfusion the synaptosomes are subjected to two 5 sec washes with basal buffer, with a flow rate of about 1.2 ml/sec and the effluent is collected for radioactive disposal. After the wash, the outlet is centering on the fraction collection vials. A typical protocol (with 16 rpm) consists of a first 1.08 sec superfuse with basal buffer and switch to a high-K+ buffer for 2.1 sec and a switch back to basal buffer for the remaining time. By selecting "Do the superfusion" from the menu and activating by returning, the effluent flows into vials on a rotating turntable platter.

EFFLUENT COLLECTION

This is done using a turntable which rotates at 16, 33, 45 and 78 rpm, giving 3.75, 1.82, 1.33 and 0.77 seconds for each rotation. On the turntable a platter with 50 uniformly drilled holes in a circle to allow for glass vials for collecting the effluent. So, depending on the rpm of turntable, one can collect fraction of as long as 66 msec or as short as 15 msec.

The superfusion event and the fraction collection are synchronized with a magnetic reed switch that is activated by a permanently fixed magnet to the turntable. If the flow rate is 1.25 ml/sec, at 33 rpm each fraction is 45 ul.

To the fractions, one ml of "Hydrofluor" (National Diagnostics, Manville, N.J.) is added, and the fractions are counted in a liquid scintillation counter. After superfusion, all the filters in the chamber are taken out and suspended in 1 ml of counting fluid and counted after placing it overnight on a shaking platform and counted the next day.

DATA ANALYSIS

Lotus 123 spreadsheet software is used to analyze the data. The liquid scintillation counter gives the averaged cpm directly. Using a spreadsheet, the counts are entered against time (and fraction number). In the next column, the counter background is subtracted for each fraction. All of the counts are summed, including the ones retained on the filter. This represents the total amount taken up by the synaptosomes. From this sum, each fraction is calculated as a percent release and plotted against time. This plot would clearly show the pattern of baseline, valve opening and tracer release. Plotting these net results against valve 3 time gives the net release of radiolabelled guanidine in response to experimental buffer as a function of time.

FIG. 1 depicts a graph showing $^3$H glutamate release from rat brain synaptosome which had been loaded with $^3$H-glutamate for 10 minutes at 30° C. The synaptosomes (50 μg protein) were loaded into the superfusion chamber and washed for 10 seconds with the basal buffer containing 145 mM NaCl and 5 mM KCl. The superfusion was then started immediately. At time 0, the synaptosomes were depolarized by switching to a high K buffer (40 mM NaCl, 110 mM KCl). The upper curve in FIG. 1 denotes release evoked in the presence of 2.4 mM $Ca^{2+}$. The lower curve displays release evoked in Ca-free buffer. The data are expressed as a percent of the total $^3$H-glutamate pool released in each 72 millisecond fraction collected. Error bars are for triplicate determinations.

Example 9

Assay for Inhibition of Glutamate Release

The experimental drugs are first dissolved in methanol to make a stock of 20 mM. This solution is diluted into the basal buffer as well as high-K+ buffer to give the required concentration of this drug. All solutions including the controls are made to have the same concentration of methanol. Methanol concentration never exceeded 0.3% (v/v) of buffers. Synaptosomes were first exposed to the drugs during the wash before superfusion and also during the entire superfusion protocol. The total time synaptosomes were exposed to the test organic compounds before the glutamate release was <25 sec.

FIG. 2 depicts a graph showing the effect of 0 uM, 10 uM, 30 uM and 100 uM N,N'-di-(adamantan-1-yl)guanidine on the release of $^3$H-glutamate from rat brain synaptosomes. The same concentrations of the guanidine were maintained in all superfusion solutions. The results are plotted in terms of cumulative amount of glutamate release in a single 2.1 second K+ depolarizing pulse, as the percent of total radioactive glutamate loaded in the synaptosomes. As is clear from FIG. 2, increasing concentrations of N,N'-di(adamantan-1-yl)guanidine resulted in decreasing release of glutamate from synaptosomes.

Following the above procedure, a number of additional compounds were screened for glutamate-release inhibitory activity. The relative levels of glutamate release in the presence of these compounds of the invention appear in Table I.

TABLE I

| Compound | 30 μM[1] | 100 μM[1] |
|---|---|---|
| N,N'-di-(o-tolyl)guanidine | nd[2] | 91 |
| N,N'-di-(2-iodophenyl)guanidine | nd | 61 |
| N,N-di-(3-methylphenyl)guanidine | nd | 106 |
| N-cyclohexyl-N'-(2-methylphenyl)-guanidine | 100 | nd |
| N-(adamantan-1-yl)-N'-cyclohexyl-guanidine | 120 | nd |
| N,N-di-(adamantan-1-yl)guanidine | 45 | 13 |
| N-(adamantan-1-yl)-N'-(2-iodophenyl)guanidine | 39 | nd |
| N-(adamantan-1-yl)-N'-(2-methylphenyl)guanidine | 52 | 45 |
| N-(adamantan-2-yl)-N'-(2-iodophenyl)guanidine | 74 | nd |
| N-(adamantan-2-yl)-N'-(2-methylphenyl)guanidine | 100 | nd |
| N-((±)-endo-2-norbornyl)-N'(2-iodophenyl)guanidine | 77 | nd |
| N,N'-di-(adamantan-2-yl)guanidine | 40 | 20 |
| N,N'-di-(1-naphthyl)guanidine | 19 | 29 |
| N-(α-naphthyl)-N'-(2-iodophenyl)-guanidine | 77 | nd |
| N-(3-ethylphenyl)-N'-(1-naphthyl)-guanidine | 59 | nd |
| Di-(o-methyl)benzyl)amine | 100 | nd |
| N,N'-di-(3-ethylphenyl)-N-methyl-guanidine | 88 | nd |
| N,N',N'',N'''-tetracyclohexylhydrazinedicarboximidamide | 51 | nd |
| N-(1-naphthyl)-N'-(o-isopropylphenyl)guanidine | 100 | nd |
| N-(1-naphthyl)-N-methyl-N'-(o-isopropylphenyl)guanidine | 95 | nd |
| N-(1-naphthyl)-N'-(m-ethylphenyl)-N'-methylguanidine | 76 | 21 |
| Control | 100 | 100 |

[1]Concentration.
[2]nd = not done.

Figure 3:
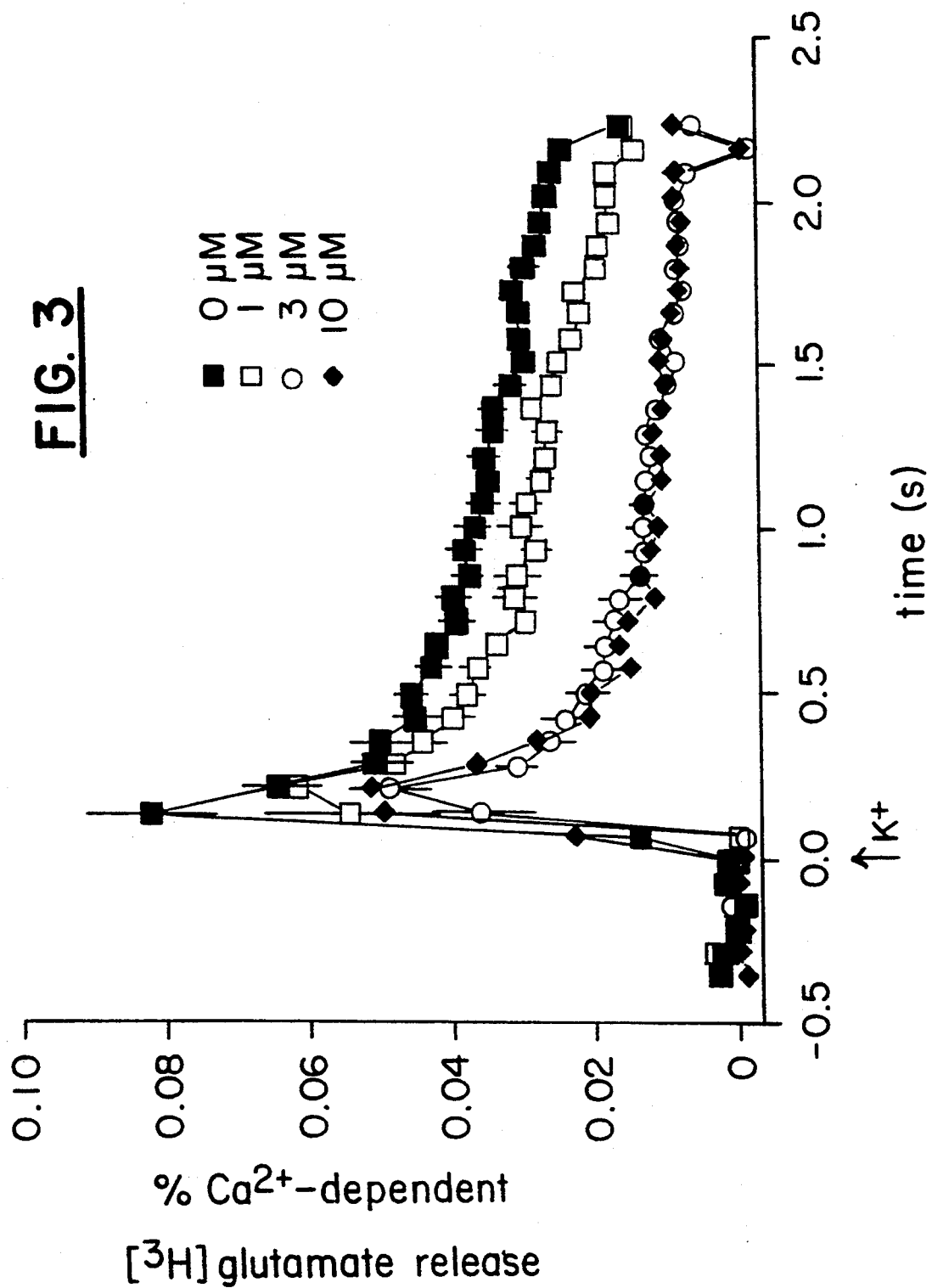
FIG. 3 depicts a graph showing the effect of 0 uM, 1 uM, 3 uM and 10 uM of N,N'-di(5-acenaphthyl)guanidine over time on the $Ca^{2+}$-dependent release of [$^3H$]glutamate from radiolabelled synaptosomes after $K^+$ depolarization (at time 0).

FIG. 3 depicts a graph showing the effect of 0 uM, 1 uM, 3 uM and 10 uM of N,N'-di(5-acenaphthyl) guanidine over time on the Ca$^{2+}$-dependent release of [$^3$H]glutamate from radiolabelled synaptosomes after K+ depolarization (at time 0). FIG. 3 indicates that this compound is a potent inhibitor of glutamate release from brain nerve terminal preparations. At 3–10 uM concentrations, it blocks the persistent component of Ca$^{2+}$-dependent glutamate release more than the initial transient component.

Example 10

Correlation Between Inhibition of Ca Uptake with Inhibition of Glutamate Release Several compounds were also tested to determine whether the Ca$^{2+}$ dependent and independent components of glutamate release are related to the blockage of $^{45}$Ca uptake. Calcium uptake is one step in the cascade of events which occur in neuronal cell death from ischemia. See Bassaclough and Leach, *Current Patents Ltd.*, 2–27 (19__). The Ca-flux protocol is as follows. Rat brain synaptosomes were prepared according to Hajos, *Brain Res.* 93:485 (1975). Synaptosomes were suspended in low potassium "LK" buffer (containing 3 mM KCl) at 2 mg/ml. Drugs in LK were added to synaptosomes to a final concentration of 10 μM and incubated for 5 min at room temperature. $^{45}$Ca uptake was then measured by adding isotope in either LK or high potassium (150 mM KCl) containing buffer. After 5 seconds, the $^{45}$Ca flux was stopped with 0.9 ml quench solution (LK+10 mM EGTA). The solution was filtered under vacuum and the filters washed with 15 ml of quench buffer. The effect of drug is expressed as % inhibition (or block) of control potassium-stimulated $^{45}$Ca influx. This method is an adaptation of the method disclosed by Nachsen and Blaustein, *J. Physiol.* 361:251–268 (1985).

As shown in FIG. 4, there is a near linear correlation between the inhibition of synaptosomal $^{45}$Ca uptake and inhibition of the persistent component (Δ) of glutamate release by N-(adamantan-1-yl)-N'-(2-methylphenyl)-guanidine (#1), N-(1-naphthyl)-N'-(m-ethylphenyl)-N'-methylguanidine (#2), N,N'-di-(1-naphthyl)guanidine (#3), N,N'-diadamantan-1-yl)guanidine (#4), N,N'-di-(adamantan-2-yl)guanidine (#5), N,N',N'',N'''-tetracyclohexylhydrazinedicarboximidamide (#6) and N,N'di-(5-acenaphthyl)guanidine. In contrast, there was no correlation between the inhibition of synaptosomal $^{45}$Ca uptake and the inhibition of the phasic component (o) of glutamate release (FIG. 4). An exception is N,N'-di(5-acenaohthyl)guanidine which inhibits the persistent component of glutamate release to a greater degree than predicted by its ability to inhibit $^{45}$Ca uptake.

Figure 6:
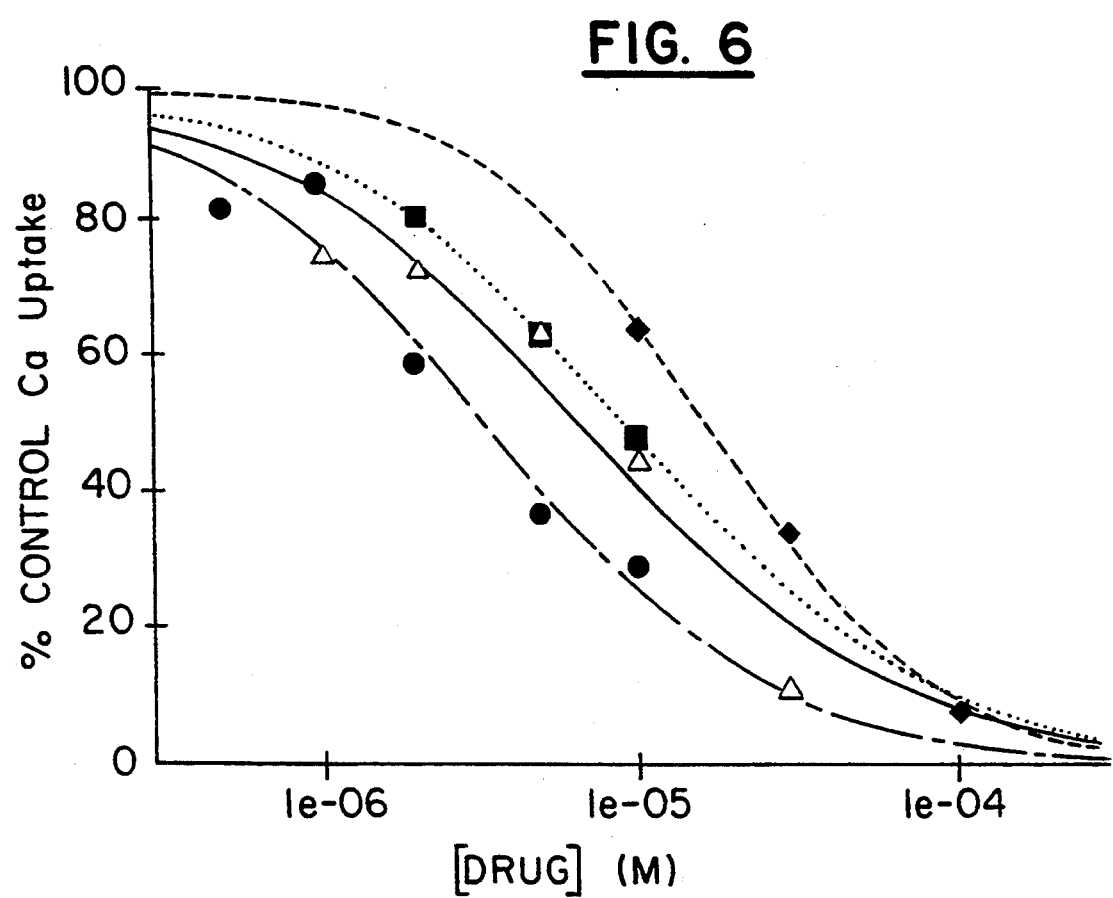
FIG. 6 depicts a graph showing the inhibition of potassium-stimulated Ca uptake of synaptosomes by N,N'-di-(adamantan-2-yl)guanidine (■), N,N'-di-(1-naphthyl)guanidine (♦;...$IC_{50}=9.1$ $\mu M$, ---$IC_{50}=16$ $\mu M$), N,N',N'', N'''-tetracyclohexylhydrazinedicarboximidamide (•; _._ $IC_{50}=3.3$ $\mu M$), and N,N'-di-(adamantan-1-yl)guanidine (Δ; __ IC$_{50}$=6.6 μM) against the percent of Ca uptake compared to control synaptosomes.

FIG. 6 depicts a graph showing the inhibition of potassium-stimulated Ca uptake of synaptosomes by N,N'-di-(adamantan-2-yl)guanidine (■), N,N'-di-(1-naphthyl)guanidine (♦;...IC$_{50}$=9.1 μM, ---IC$_{50}$=16 μM), N,N',N'', N'''-tetracyclohexylhydrazinedicarboximidamide (•; __.__ IC$_{50}$=3.3 μM), and N,N'-di-(adamantan-1-yl)guanidine (Δ; __ IC$_{50}$=6.6 μM) against the percent of Ca uptake compared to control synaptosomes. As shown in FIG. 6, the drugs caused an inhibition of potassium-stimulated Ca uptake in a dose-dependent manner.

A number of additional compounds (at 10 μM) were tested for activity in inhibiting/potentiating the potassium-stimulated uptake of calcium into synaptosomes. The results are shown in Table II:

TABLE II

| Compound | % Uptake vs. Control |
| --- | --- |
| N-(α-Naphthyl)-N'-(1-piperidinyl)-guanidine | 131 |
| N-(Cyclohexyl)-N'-(1-piperidinyl)-guanidine | 108 |
| N-(α-Naphthyl)-N'-(4-phenylpiperidinyl)-guanidine | 79 |
| N,N'-Bis(indan-1-yl)-guanidine | 88 |
| N,N'-Bis(m-ethylphenyl)-2-imino-imidazolidine | 101 |
| N,N'-Bis(o-tolyl)-N,N'-butanyl(bridge)-guanidine | 119 |
| N-N'-Bis(1-Adamantanemethyl)-guanidine | 111 |
| N-(8-Aminocoumarinyl)-N'-(m-ethylphenyl)-N'-methyl-guanidine | 151 |
| N,N'-Bis(1,2,3,4-tetrahydro-1-quinolinyl)-guanidine | 87 |
| N,N'-Bis(5-acenaphthyl)-guanidine | 43 |
| N-(m-Ethylphenyl)-N'-(2-carboethoxy-7-benzofuranyl)-N-methyl guanidine | 71 |
| N-(α-Naphthyl)-N'-(m-ethylphenyl)-N''-cyanoguanidine | 95 |
| N-(Adamantan-1-yl)-N'-(4,5-benzo-2-thia-1,3-diazol-6-yl)guanidine | 98 |

Table III shows the percentage inhibition of synaptosomal $^{45}$Ca uptake by certain N,N'-disubstituted guanidines of the invention.

TABLE III

Inhibition of Synaptosomal $^{45}$Ca Uptake By Substituted Guanidines and Related Compounds

| Compound | % Inhibition @ 10 μM (SEM) | IC50, μM |
| --- | --- | --- |
| N,N'-Bis(5-acenaphthyl)guanidine | 46 (±15) | 10.7 ± 3 |
| N-(Adamantan-1-yl)-N'(α-naphthyl)guanidine | 31 (±14) | — |
| N-(5-acenaphthyl)-N'-(4-isopropyl-phenyl)guanidine | 68 (±1) | 6.5 ± 1 |
| N-(Adamantan-1-yl)-N'-(adamantan-2-yl)guanidine | 49 (±8) | — |
| N,N'-Bis(p-tert.-butylphenyl)guanidine | 47 (±7) | — |
| N-(5-acenaphthyl)-N'-(4-fluoro-naphthyl)guanidine | 47 (±4) | — |
| N-(5-acenaphthyl)-N'-(4-hydroxy-naphthyl)guanidine | 35 (±7) | — |
| N-(5-acenaphthyl)-N'-(4-methoxy-naphthyl)guanidine | 56 (±3) | — |
| N-(Adamantan-2-yl)-N'-(5-acenaphthyl)guanidine | 69 (±3) | 4.8 |
| N,N'-Bis (3-acenaphthyl)guanidine | 36 (±14) | 11 |
| N,N',N'', N'''-tetracyclohexyl-hydrazine-dicarboximidamide | 74 (±6) | 3 |
| N,N'-Di-(adamantan-2-yl)guanidine | 35 (±12) | 16.1 ± 10 |
| N,N'-Bis(1-naphthyl)guanidine | 27 (±5) | 23.6 ± 10 |
| N,N'-Di-(4-isopropylphenyl)guanidine | 48 (±14) | 19 ± 7 |
| N-(5-acenaphthyl)-N'-(adamant-1-yl)-guanidine | 47 ± 11 | 9.7 ± 3 |
| N-(5-acenaphthyl)-N'-(1-naphthyl)guanidine | 40 ± 6 | 16.2 ± 0.4 |
| N,N'-Di-(adamantan-1-yl)guanidine | 25 (±11) | 25 ± 9 |

Table IV shows the percentage inhibition of glutamate release (persistent component) by certain N,N'-disubstituted guanidines of the invention.

TABLE IV

Inhibition of Glutamate Release (Persistent Component) By Substituted Guanidines and Related Compounds

| Compound | % Inhibition @ 10 μM | IC50, μM |
| --- | --- | --- |
| N,N'-Bis(5-acenaphthyl)guanidine | 92 | 3 |
| N-(5-acenaphthyl)-N'-(4-fluoronaphthyl)guanidine | 85 | <5 |
| N-(5-acenaphthyl)-N'-(4-hydroxynaphthyl)guanidine | 25 | |
| N-(5-acenaphthyl)-N'-(4-methoxynaphthyl)guanidine | 90 | |
| N-(Adamantan-2-yl)-N'-(5-acenaphthyl)guanidine | 63 | 5 |
| N,N',N'', N'''-tetracyclohexylhydrazine-dicarboximidamide | 67 | |
| N,N'-Di-(adamantan-2-yl)guanidine | 60 | |
| N,N'-Bis(1-naphthyl)guanidine | 31 | |
| N,N'-Di-(adamantan-1-yl)guanidine | 49 | |

Example 11

Inhibition of Glutamate Release of Synaptosomes Depolarized with Veratridine

Figure 5:
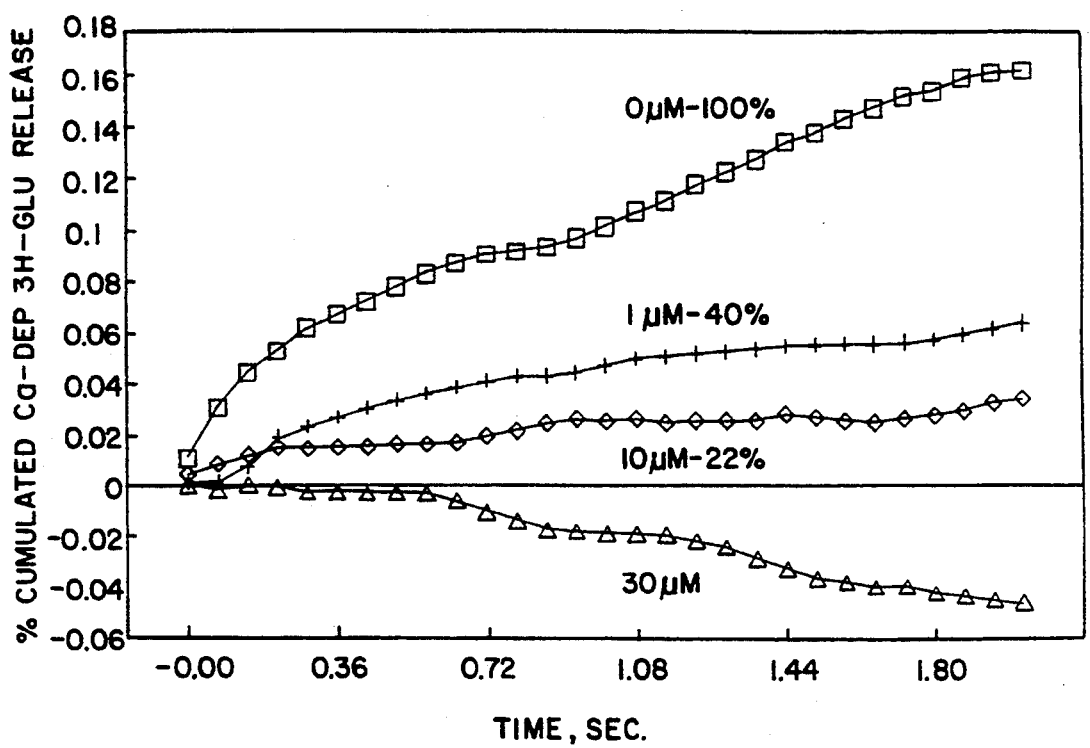
FIG. 5 depicts a graph showing the effects of various concentrations of N,N'-di-(adamantan-2-yl)guanidine on the $Ca^{2+}$-dependent glutamate release stimulated with the sodium channel activator veratridine.

Next, the effect of various concentrations of N,N'-di-(adamantan-2-yl)guanidine on $Ca^{2+}$ release of synaptosomes depolarized with veratridine was evaluated. As shown in FIG. 5, increasing concentrations of N,N'-di-(adamantan-2-yl)guanidine caused an inhibition of glutamate release in a dose dependent manner.

Example 12

The Effect of N,N'-di(5-acenaphthyl)guanidine on Sodium Currents in Neuroblastoma Cells Whole cell sodium currents were elicited in voltage clamped N1E-115 neuroblastoma cells, using the stimulus protocol shown on the top of FIG. 7. Pressure ejection of 30 uM N,N'-di(5-acenaphthyl)guanidine onto these cells (N=5) blocked inward sodium currents by an average of 40% (49% inhibition in the cell shown, the results for which are depicted in FIG. 7). The effects of this drug were partially reversed following washout.

Example 13

Figure 8:
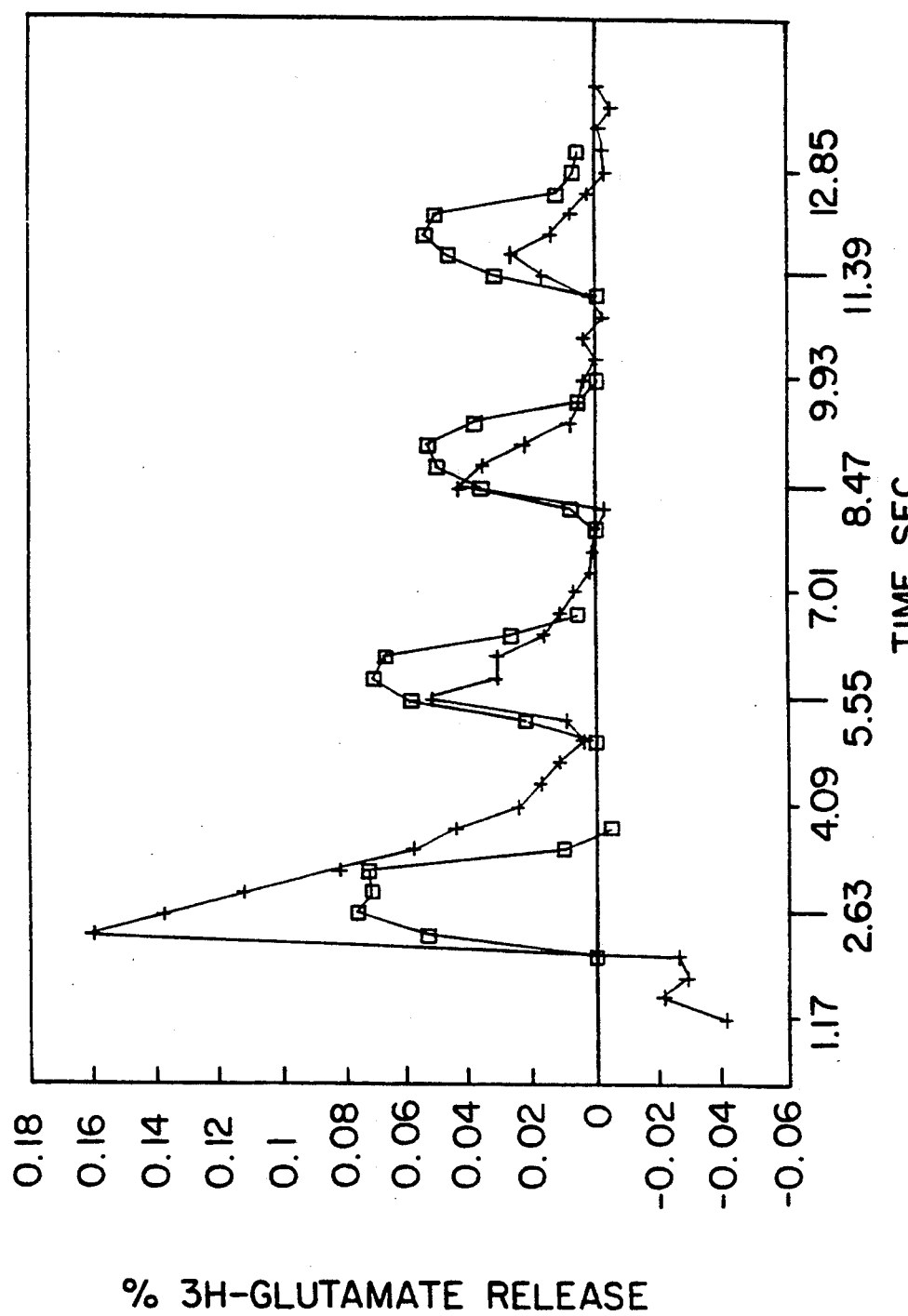
FIG. 8 depicts a graph showing the Ca-independent and Ca-dependent recovery of $^3$H-glutamate release from synaptosomes over time.
Figure 9:
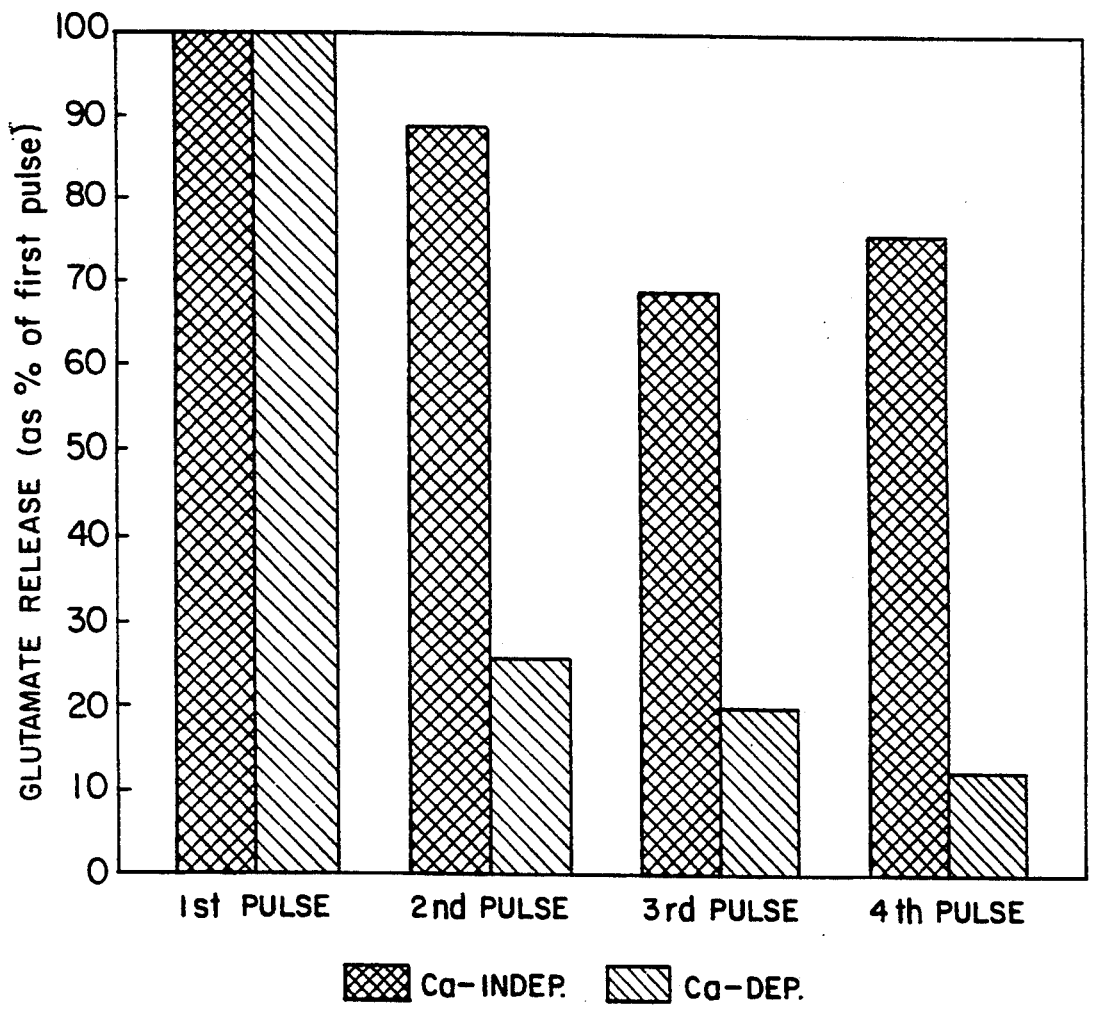
FIG. 9 depicts a graph showing the Ca-independent and Ca-dependent recovery of $^3$H-glutamate release from synaptosomes, as a percentage of the first pulse.

Monitoring of the Use-Dependence with the Superfusion System $^3$H-glutamate loaded synaptosomes were washed for 10 sec. to washout the exterior radioactivity and the superfusion was started. The superfusion consisted of 2 sec. low-K+ (3 mM) buffer flow followed by 1 sec. of high-K+ (55 mM) flow. This was repeated three more timed followed by 2 sec. of low-K+ buffer. The results are shown in FIGS. 8 and 9. Ca-independent and Ca-dependent glutamate release in the later pulses were expressed as a percent of their initial fluxes. FIGS. 8 and 9 show that Ca-independent glutamate release is fairly constant whereas the Ca-dependent component decays and requires time to recover.

Example 14

Electrophysiology Studies on N-type Channels

Figure 10:
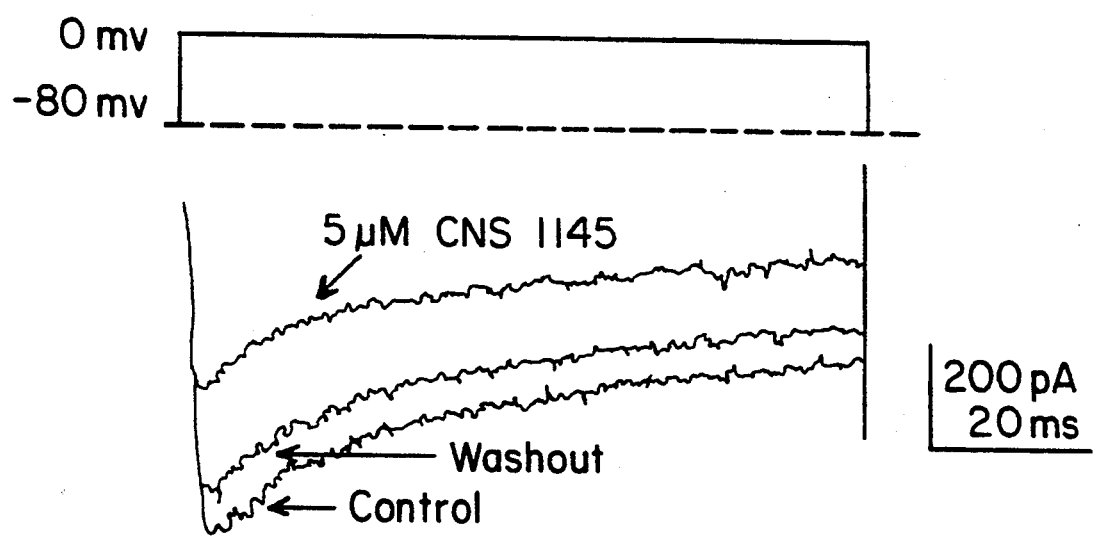
FIG. 10 depicts a graph showing an electrophysiology study on N-type channels of single bullfrog dorsal root ganglion cells treated with 5 uM of N,N'-di(acenaphthyl)guanidine.

Single bullfrog dorsal root ganglion cells, which express ω-conotoxin-sensitive N-type calcium channels, were treated with 5 uM of N,N'-di(acenaphthyl)guanidine. The solution also contained (in mM) CsCl, 90; creatine phosphate, 5; MgATP, 5; tris GTP, 0.3; EGTA, 10; HEPES, 10; pH 7.2. As shown in FIG. 10, this compound inhibited about 40% of the current. At 20 uM, this compound inhibited nearly all of the current (not shown). Most of the inhibition was reversed in about 6 minutes (not shown). Calcium channel rundown during the recording period may account for the lack of complete reversal of inhibition. This further supports the hypothesis that certain substituted guanidines inhibit neurotransmitter release by clocking presynaptic calcium channels.

Example 15

Electrophysiology Studies on Excitatory Synaptic Transmission

Figure 11:
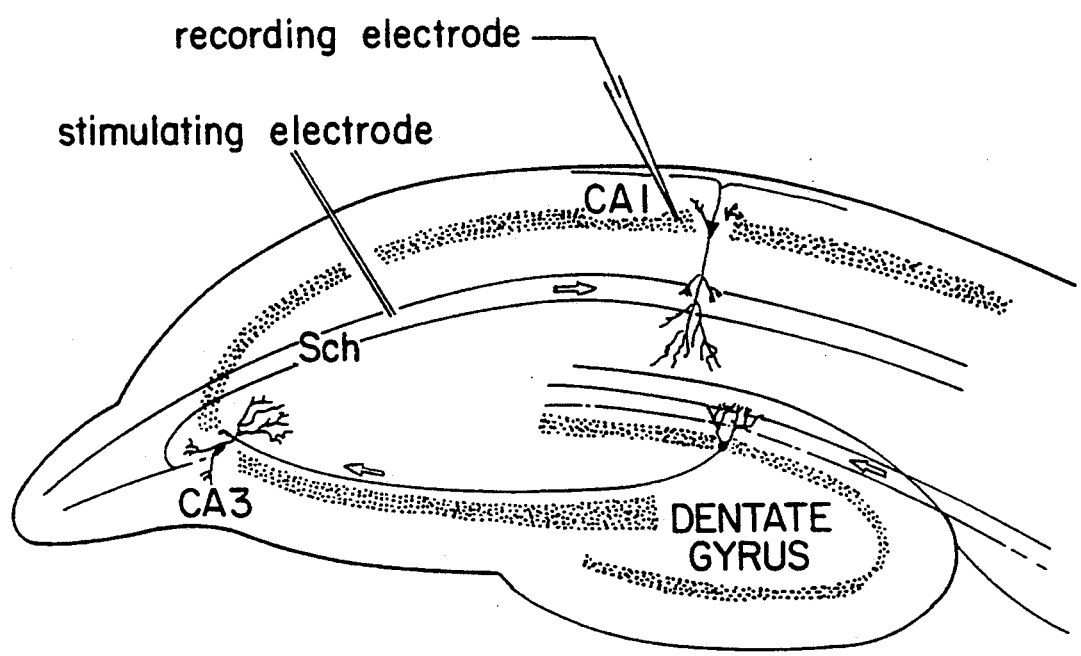
FIG. 11 depicts a hippocampal slice preparation containing a stimulating and recording electrode.

Transverse sections of hippocampus were obtained from 4–6 week old Sprague-Dawley rats and maintained under standard conditions. As shown in FIG. 11, synaptic potentials were elicited by application of constant current electrical stimuli delivered through concentric bipolar platinum/iridium electrodes placed in the *stratum radiatum* to ensure full stimulation of the Schaffer collaterals. Extracellular excitatory post synaptic potentials (EPSP's) were recorded by placing a saline-filled glass microelectrode in either the *stratum radiatum* or *stratum lacunosum*. Population spikes were recorded by placing an electrode in the *stratum pyramidole*.

Figures 12A, 12B:
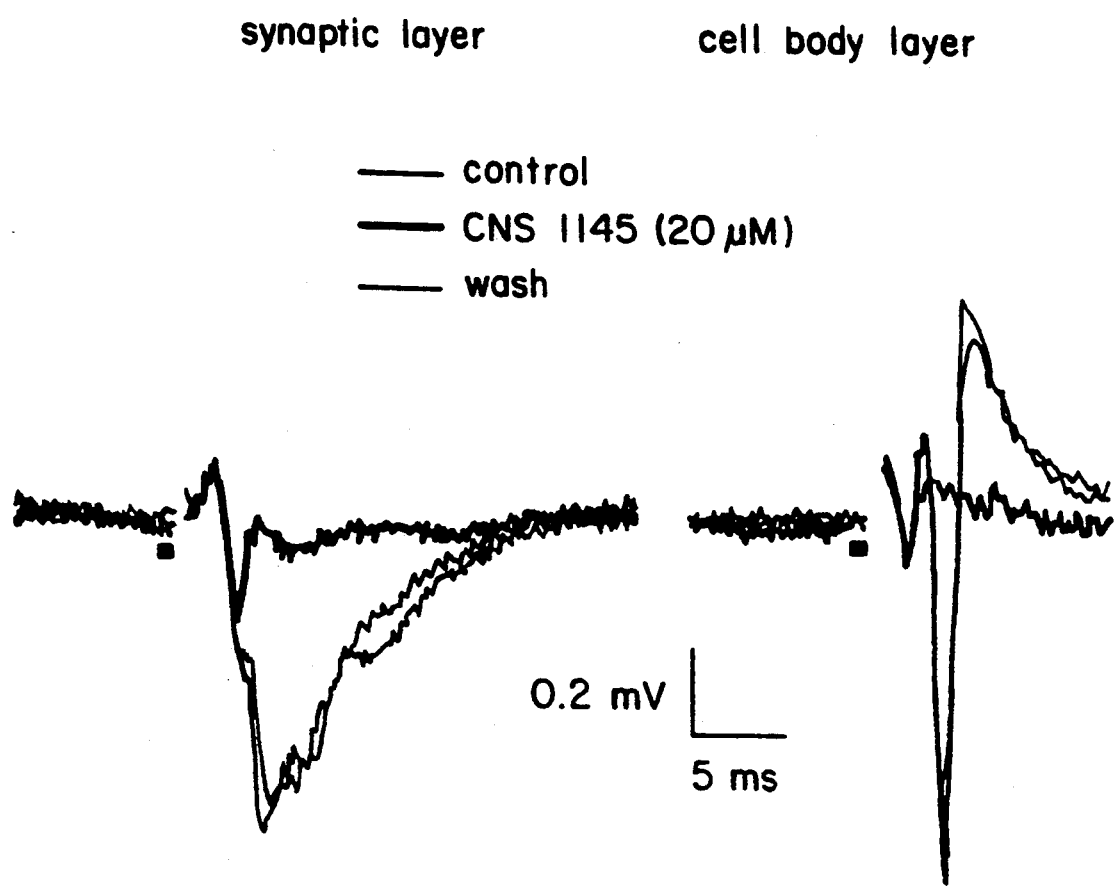
FIG. 12A depicts a graph showing the results from the bath application of N,N'-di(5-acenaphthyl)guanidine on population spikes and field EPSP.
FIG. 12B depicts a graph showing the results from the bath application of N,N'-di(5-acenaphthyl)guanidine on the field EPSP after electrical stimulation.

As shown in FIG. 12A, the bath application of N,N'-di(5-acenaphthyl)guanidine completely eliminated population spikes. This effect is completely reversible following washout. The upwardly going field EPSP was also reversibly blocked by bath perfusion of the drug.

As shown in FIG. 12B, the bath application of N,N'-di(5-acenaphthyl)guanidine almost completely eliminated the field EPSP. This effect is fully reversible following washout. Small population spikes are also evident superimposed on the late phase of the EPSP. The bath perfusion of this compound also reversibly blocked these population spikes.

Figure 12C:
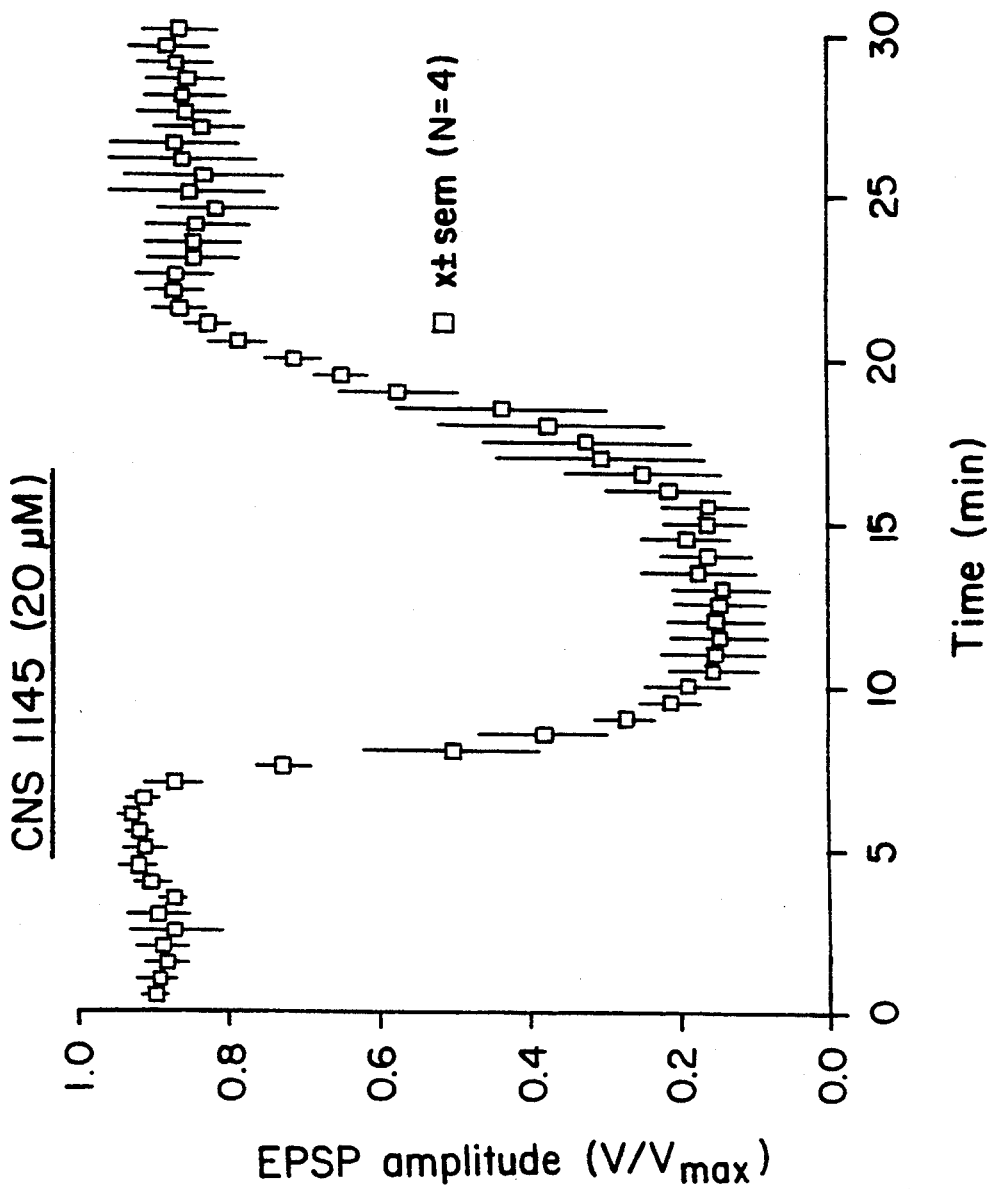
FIG. 12C depicts the effect of 20 uM of N,N'-di(5-acenaphthyl)guanidine on the amplitude of the response to an electrical stimulus.

FIG. 12C depicts the effect of 20 uM of N,N'-di(5-acenaphthyl)guanidine on the amplitude of the response to an electrical stimulus. EPSP amplitude was reduced between 80–90% and the response was fully recovered following washout.

Figure 13A:
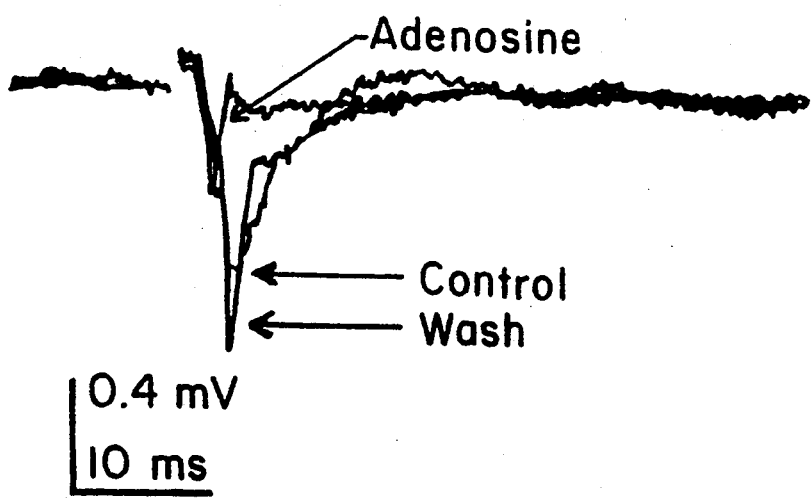
FIG. 13A depicts a graph showing the results from the bath application of adenosine on the field EPSP after electrical stimulation.

FIG. 13 depicts two graphs showing the effect of 1 mM adenosine (a known presynaptic transmitter release blocker) on EPSP amplitude in hippocampal slices. FIG. 13A shows that the bath application of adenosine almost completely eliminated field EPSP's in a fully reversible fashion. There was a noticeable overshoot following recovery. Population spikes occurring during the late phase of EPSP were totally blocked by adenosine but did not appear to return following washout. The presence and duration of the presynaptic volley was unaffected by adenosine; however, there appeared to be a small reversible change in amplitude. While transmitter release may be blocked, there is no measurable effect on the afferent volley. In addition, this experimental paradigm cannot distinguish between presynaptically and postsynaptically mediated reductions of extracellularly measured synaptic potentials.

Figure 13B:
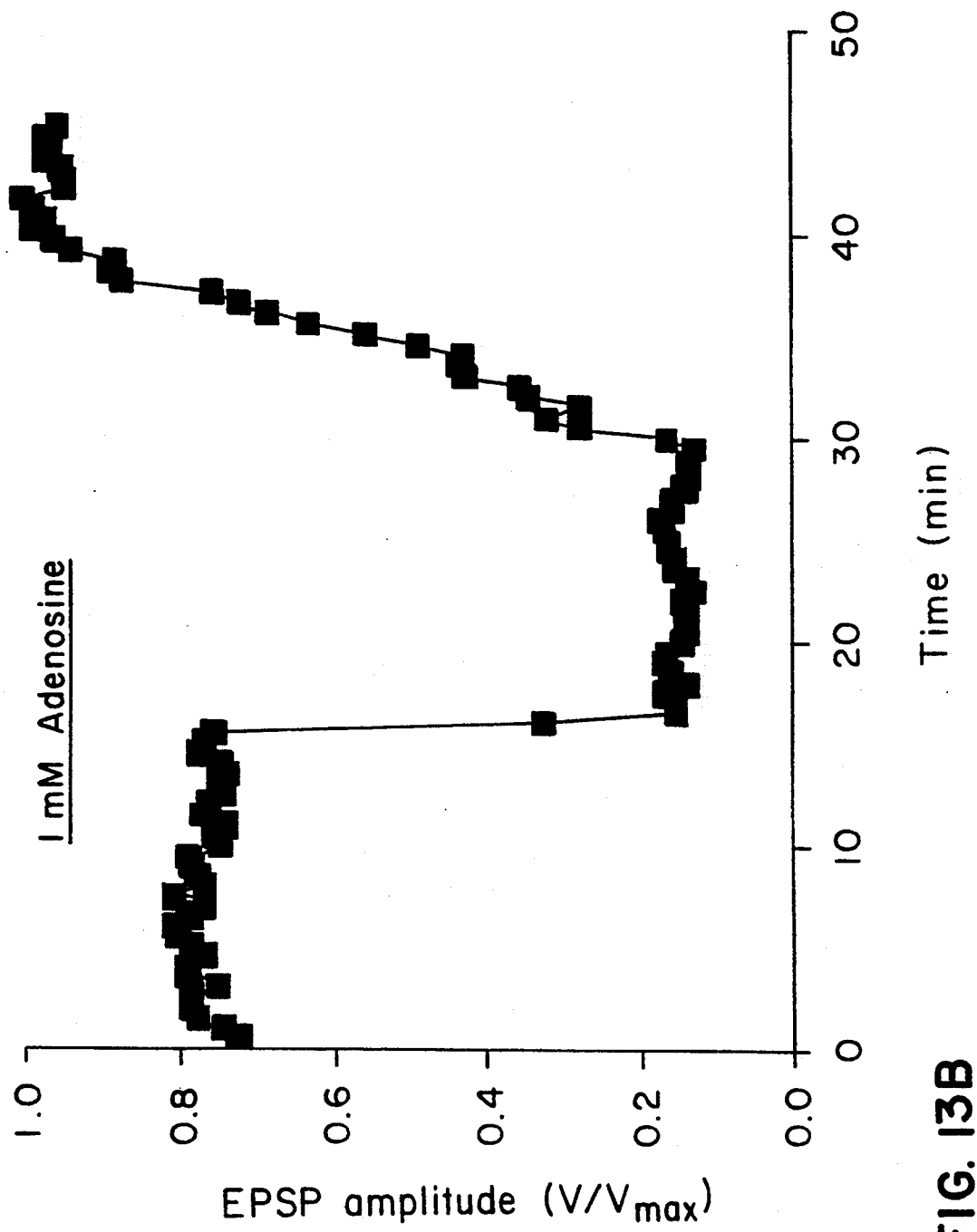
FIG. 13B depicts the effect of adenosine on the amplitude of the response to an electrical signal.

FIG. 13B shows the effect of 1 mM adenosine on normalized EPSP amplitude (measured EPSP amplitude divided by maximum EPSP amplitude in millivolts) over time. Bath application of adenosine caused a 90% reduction in the EPSP amplitude of the field EPSP (first response to paired stimuli shown here). This effect is fully reversible following washout with some overshoot evident in this slice.

The results of the hippocampal slice recordings lead to the following conclusions. The bath application of N,N'-di(5-acenaphthyl)guanidine (20 uM) substantially and reversibly reduced the amplitude of both field EPSP's and population spikes by 80–90%. The effects of this compound were fully reversible, The effects of this compound qualitatively resembles the actions of adenosine, an agonist of the presynaptic adenosine receptors which is known to block glutamate release. This is consistent with presynaptic inhibition of neurotransmitter release by the compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for treating or preventing nerve cell death comprising the administration to a mammal exhibiting symptoms of nerve cell death or susceptible to nerve cell death, an effective amount of a compound having the formula:

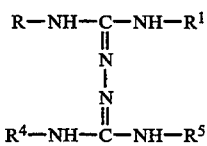

or a tautomer thereof,
wherein R, $R^1$, $R^4$ and $R^5$ are the same or different and are cycloalkyl of 3 to 12 carbon atoms, carbocyclic aryl, alkaryl, aralkyl or heterocyclic, wherein R, $R^1$, $R^4$ or $R^5$ may be optionally substituted by hydroxy, amino, lower $C_{1-6}$ alkyl, lower $C_{1-6}$ alkyl amino, alkoxy of 1–6 carbon atoms, di-lower $C_{2-12}$ alkyl amino, nitro, azido, sulfhydryl, cyano, isocyanato, halogen, amido, or carbamido.

2. The method of claim 1 where one or more of R, $R^1$, $R^4$ and $R^5$ is cyclopropyl, cyclopentyl, cyclohexyl, cyclohexenyl, cycloheptyl, 1,4-methylenecyclohexyl, 1-adamantyl, 2-adamantyl, exo 2-norbornyl, endo 2-norbornyl, exo 2-isobornyl, endo 2-isobornyl, menthyl, cyclopentyl-methyl, cyclohexylmethyl, 1-cyclohexylethyl, 2-cyclohexylethyl, 1-cyclohexylpropyl, 2-cyclohexylpropyl or 3-cyclohexylpropyl.

3. The method of claim 1 where one or more R, $R^1$, $R^4$ and $R^5$ is heterocyclic having from 6 to 18 carbons atoms and containing 1–3 separate or fused rings, and 0–5 O, N and/or S ring atoms in an aryl, alicyclic or mixed ring system.

4. The method of claim 3 where said heterocyclic aryl, alicyclic or mixed ring system is phenyl, benzyl, 1-phenylethyl, 2-phenylethyl, 1-phenylpropyl, 2-phenylpropyl, 3-phenylpropyl, o-tolyl, m-tolyl, p-tolyl, m,m'-dimethylphenyl, o-ethylphenyl, m-ethylphenyl, p-ethylphenyl, m,m'-diethylphenyl, m-methyl-m'-ethylphenyl, o-propylphenyl, 1-naphthyl, 2-naphthyl, biphenyl, indanyl, indenyl, 3-acenaphthyl, 5-acenaphthyl, 3-acenaphthylene, 5-acenaphthylene, indolyl, benzthiazole, quinolinyl, isoquinolinyl, pyridyl, pyrimidinyl, pyrazinyl, furanyl, thienyl, pyrrolyl, thiazolyl, oxazolyl, coumarinyl or imidazolyl.

5. The method of claim 1, wherein said compound is N,N',N'',N'''-tetracyclohexylhydrazine-dicarboximidamide, N,N',N'',N'''-tetraphenylhydrazine-dicarboximidamide, N,N'-di-(adamantan-1-yl)-N'',N'''-dicyclohexylhydrazine-dicarboximidamide, N,N',N'',N'''-tetra-(adamantan-1-yl)hydrazinedicarboximidamide, N,N',N'',N'''-tetra-(adamantan-2-yl)-hydrazinedicarbox-imidamide, N,N'-di-(adamantan-1-yl)-N'',N'''-di-(adamantan-2-yl)hydrazinedicarboximidamide, N,N'-di(2-norbornyl)-N''N'''-dicyclohexylhydrazine-dicarboximidamide, N,N'-di-(2-isobornyl)-N'',N'''-dicyclohexylhydrazinedicarboximidamide, N,N'-di-(2-isobornyl)-N'',N'''-di-(adamantan-1-yl)hydrazinedicarboximidamide, N,N'-di-(2-isobornyl)-N'',N'''-di-(adamantan-2-yl)hydrazinedicarboximidamide, N,N',N'',N'''-tetra-(acenaphth-5-yl)hydrazine-dicarboximidamide, N,N',N''N'''-tetra-(acenaphthylen-5-yl)-hydrazinedicarboximidamide, N,N'-di(acenaphth-5-yl)-N'',N'''-di-(acenaphthylen-5-yl)hydrazine-dicarboximidamide, N,N'-di-(2-norbornyl)-N'',N'''-di-(acenaphth-5-yl)hydrazinedicarboximidamide, N,N'-di-(2-norbornyl)-N'',N'''-di-(acenaphthylen-5-yl)hydrazine-dicarboximidamide, N,N'-di-(2-isobornyl)-N'',N'''-di-(acenaphth-5-yl)hydrazinedicarboximidamide, N,N'-di-(2-isobornyl)-N'',N'''-di-(acenaphthylen-5-yl)hydrazinedicarboximidamide, N,N'-dicyclohexyl -N''N'''-di-(acenaphth-5-yl)hydrazinedicarboximidamide, or N,N'-dicyclohexyl-N'',N'''-di-(acenaphthylen-5-yl)hydrazine-dicarboximidamide.

6. A method for treating or preventing nerve cell death comprising the administration to a mammal exhibiting symptoms of nerve cell death or susceptible to nerve cell death, an effective amount of a compound having the formula:

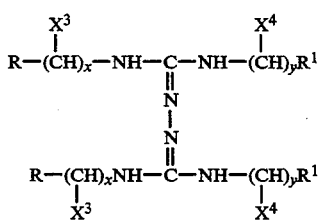

or a tautomer thereof,
wherein R and $R^1$ are the same or different and are cycloalkyl of 3 to 12 carbon atoms, carbocyclic aryl, alkaryl, aralkyl or heterocyclic, $X^3$ and $X^4$ are the same or different and are selected from the group consisting of hydrogen, hydroxy, amino, lower $C_{1-6}$ alkyl, lower $C_{1-6}$ alkyl amino, alkoxy of 1–6 carbon atoms, di-lower $C_{2-12}$ alkyl amino, nitro, azido, sulfhydryl, cyano, isocyanato, halogen, amido, or carbamido;
wherein R and $R^1$ are optionally substituted by hydroxy, amino, lower $C_{1-6}$ alkyl, lower $C_{1-6}$ alkyl amino, alkoxy of 1–6 carbon atoms, di-lower $C_{2-12}$ alkyl amino, nitro, azido, sulfhydryl, cyano, isocyanato, halogen, amido, or carbamido;
x and y are the same or different and are 0, 1, 2, 3 or 4.

7. The method of claim 6 where one or both of R and $R^1$ is cyclopropyl, cyclopentyl, cyclohexyl, cyclohexenyl, cycloheptyl, 1,4-methylenecyclohexyl, 1-adamantyl, 2-adamantyl, exo 2-norbornyl, endo 2-norbornyl, exo 2-isobornyl, endo 2-isobornyl, menthyl, cyclopentyl-methyl, cyclohexylmethyl, 1-cyclohexylethyl, 2-cyclohexylethyl, 1-cyclohexylpropyl, 2-cyclohexylpropyl, or 3-cyclohexylpropyl.

8. The method of claim 6 where one or both of R and $R^1$ is heterocyclic having from 6 to 18 carbon atoms and containing from 1–3 separate or fused rings, and 0–5 O, N and/or S ring atoms in an aryl, alicyclic or mixed ring system.

9. The method of claim 8 where said heterocyclic aryl, alicyclic or mixed ring system is phenyl, benzyl, 1-phenylethyl, 2-phenylethyl, 1-phenylpropyl, 2-phenylpropyl, 3-phenylpropyl, o-tolyl, m-tolyl, p-tolyl, m,m'-dimethylphenyl, o-ethylphenyl, m-ethylphenyl, p-ethylphenyl, m,m'-diethylphenyl, m-methyl-m'-ethylphenyl, o-propylphenyl, 1-naphthyl, 2-naphthyl, biphenyl, indanyl, indenyl, 3-acenaphthyl, 5-acenaphthyl, 3-acenaphthylene, 5-acenaphthylene, indolyl, benzthiazole, quinolinyl, isoquinolinyl, pyridyl, pyrimidinyl, pyrazinyl, furanyl, thienyl, pyrrolyl, thiazolyl, oxazolyl, coumarinyl or imidazolyl.

10. The method of any one of claims 1–9, wherein said compound is administered as part of a pharmaceutical composition comprising a pharmaceutically acceptable carrier.

11. The method of any one of claims 1–9, wherein said nerve cell death results from hypoxia, hypoglycemia, brain or spinal cord ischemia, brain or spinal chord trauma, stroke, heart attack, or drowning.

12. A method for treating or preventing a disease of the nervous system in which the pathophysiology of the disorder involves excessive release of a neurotransmitter from neuronal cells comprising the administration to a mammal exhibiting symptoms of such disorders or susceptible to such disorders, an effective amount of a compound having the formula:

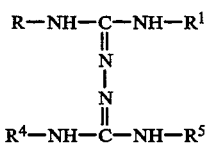

or a tautomer thereof,
wherein R, $R^1$, $R^4$ and $R^5$ are the same or different and are cycloalkyl of 3 to 12 carbon atoms, carbocyclic aryl, alkaryl, aralkyl or heterocyclic;
wherein R, $R^1$, $R^4$ or $R^5$ are each optionally substituted by hydroxy, acetate, oxo, amino, lower $C_{1-6}$ alkyl, lower $C_{1-6}$ alkyl amino, alkoxy of 1–6 carbon atoms, di-lower $C_{2-12}$ alkyl amino, nitro, azido, sulfhydryl, cyano, isocyanato, halogen, amido, sulfonato or carbamido.

13. A method for treating or preventing a disease of the nervous system in which the pathophysiology of the disorder involves excessive release of a neurotransmitter from neuronal cells comprising the administration to a mammal exhibiting symptoms of such disorders or susceptible to such disorders, an effective amount of a compound having the formula:

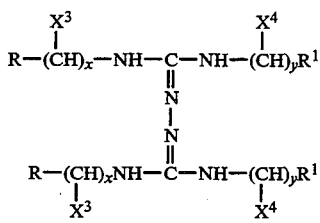

or a tautomer thereof,
wherein R and R¹ are the same or different and are cycloalkyl of 3 to 12 carbon atoms, carbocyclic aryl, alkaryl, aralkyl or heterocyclic, X³ and X⁴ are the same or different and are selected from the group consisting of hydrogen, hydroxy, acetate, oxo, amino, lower $C_{1-6}$ alkyl, lower $C_{1-6}$ alkyl amino, alkoxy of 1-6 carbon atoms, di-lower $C_{2-12}$ alkyl amino, nitro, azido, sulfhydryl, cyano, isocyanato, halogen, amido, sulfonato or carbamido;
wherein R and R¹ are optionally substituted by hydroxy, acetate, oxo, amino, lower $C_{1-6}$ alkyl, lower $C_{1-6}$ alkyl amino, alkoxy of 1-6 carbon atoms, di-lower $C_{2-12}$ alkyl amino, nitro, azido, sulfhydryl, cyano, isocyanato, halogen, amido, or carbamido;
x and y are the same or different and are 0, 1, 2, 3 or 4.

14. A method of treating or preventing a disease selected from the group consisting of Huntington's disease, Amyotrophic Lateral Sclerosis, Alzheimer's disease, Down's Syndrome, Korsakoff's diease, olivopontocerebellar atrophy, HIV-induced dementia, HIV-induced blindness, or multi-infarct demetia, the method comprising administering to a mammal exhibiting symptoms of said disease or susceptible to said disease an effective of a compound having the formula:

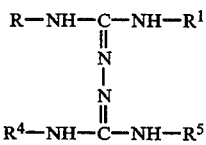

or a tautomer thereof,
wherein R, R¹, R⁴ and R⁵ are the same or different and are cycloalkyl of 3 to 12 carbon atoms, carbocyclic aryl, alkaryl, aralykl or heterocyclic, wherein R, R¹, R⁴ and R⁵ may be optionally substituted by hydroxy, amino, lower $C_{1-6}$ alkyl, lower $C_{1-6}$ alkyl amino, alkoxy of 1-6 carbon atoms, dilower C2-12 alkyl amino, nitro, azido, sulfhydryl, cyano, isocyanato, halogen, amido, or carbamido.

15. The method of claim 12 or claim 14 where one or more of R, R¹, R⁴ and R⁵ is cyclopropyl, cyclopentyl, cyclohexyl, cyclohexenyl, cycloheptyl, 1,4-methylenecyclohexyl, 1-adamantyl, 2-adamantyl, exo 2-norbornyl, endo 2-norbornyl, exo 2-isobornyl, endo 2-isobornyl, menthyl, cyclopentyl-methyl, cyclohexyl-methyl, 1-cyclohexylethyl, 2-cyclohexylethyl, 1-cyclohexylpropyl, 2-cyclohexylpropyl, or 3-cyclohexylpropyl.

16. The method of claim 12 or claim 14 where one or more of R, R¹, R⁴ and R⁵ is heterocyclic having from 6 to 18 carbons atoms and containing 1-3 separate or fused rings, and 0-5 O, N and/or S ring atoms in an aryl, alicyclic or mixed ring system.

17. The method of claim 16 where said heterocyclic aryl, alicyclic or mixed ring system is phenyl, benzyl, 1-phenylethyl, 2-phenylethyl, 1-phenylpropyl, 2-phenylpropyl, 3-phenylpropyl, o-tolyl, m-tolyl, p-tolyl, m,m'-dimethylphenyl, o-ethylphenyl, m-ethylphenyl, p-ethylphenyl, m,m'-diethylphenyl, m-methyl-m'-ethylphenyl, o-propylphenyl, 1-naphthyl, 2-naphthyl, biphenyl, indanyl, indenyl, 3-acenaphthyl, 5-acenaphthyl, 3-acenaphthylene, 5-acenaphthylene, indolyl, benzthiazole, quinolinyl, isoquinolinyl, pyridyl, pyrimidinyl, pyrazinyl, furanyl, thienyl, pyrrolyl, thiazolyl, oxazolyl, coumarinyl or imidazolyl.

18. The method of claim 12 or claim 14, wherein said compound is N,N',N'',N'''-tetracyclohexylhydrazinedicarboximidamide, N,N',N'',N'''-tetraphenylhydrazinedicarboximidamide, N,N'-di-(adamantan-1-yl)-N'',N'''-dicyclohexylhydrazinedicarboximidamide, N,N',N'',N'''-tetra-(adamantan-1-yl)hydrazinedicarboximidamide, N,N',N'',N'''-tetra-(adamantan-2-yl)-hydrazinedicarboximidamide, N,N'-di-(adamantan-1-yl)-N'',N'''-di-(adamantan-2-yl)hydrazinedicarboximidamide, N,N'-di-(2-norbornyl)-N'',N'''-dicyclohexylhydrazinedicarboximidamide, N,N'-di-(2-isobornyl)-N'',N'''-dicyclohexylhydrazinedicarboximidamide, N,N'-di-(2-isobornyl)-N'',N'''-di-(adamantan-1-yl)hydrazinedicarboximidamide, N,N'-di-(2-isobornyl)-N'',N'''-di-(adamantan-2-yl)hydrazinedicarboximidamide, N,N',N'',N'''-tetra-(acenaphth-5-yl)hydrazinedicarboximidamide, N,N',N'',N'''-tetra-(acenaphthylen-5-yl)hydrazinedicarboximidamide, N,N'-di-(acenaphth-5-yl)-N'',N'''-di-(acenaphthylen-5-yl)hydrazinedicarboximidamide, N,N'-di-(2-norbornyl)-N'',N'''-di-(acenaphth-5-yl)hydrazinedicarboximidamide, N,N'-di-(2-norbornyl)-N'',N'''-di-(acenaphthylen-5-yl)hydrazinedicarboximidamide, N,N'-di-(2-isobornyl)-N'',N'''-di-(acenaphth-5-yl)hydrazinedicarboximidamide, N,N'-di-(2-isobornyl)-N'',N'''-di-(acenaphthylen-5-yl)hydrazinedicarboximidamide, N,N'-dicyclohexyl-N'',N'''-di-(acenaphth-5-yl)hydrazinedicarboximidamide, or N,N'-dicyclohexyl-N'',N'''-di-(acenaphthylen-5-yl)hydrazinedicarboximidamide.

19. A method of treating or preventing a disease selected from the group consisting of Huntington's disease, Amyotrophic Lateral Sclerosis, Alzheimer's disease, Down's Syndrome, Korsakoff's diease, olivopontocerebellar atrophy, HIV-induced dementia, HIV-induced blindness, or multi-infarct demetia, the method comprising administering to a mammal exhibiting symptoms of said disease or susceptible to said disease an effective of a compound having the formula:

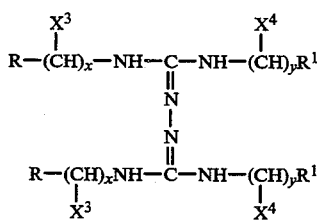

or a tautomer thereof,
wherein R and R¹ are the same or different and are cycloalkyl of 3 to 12 carbon atoms, carbocyclic aryl, alkaryl, aralkyl or heterocyclic, X³ and X⁴ are the same or different and are selected from the group consisting of hydrogen, hydroxy, amino, lower $C_{1-6}$ alkyl, lower $C_{1-6}$ alkyl amino, alkoxy of 1-6 carbon atoms, di-lower C2-12 alkyl amino, nitro, azido, sulfhydryl, cyano, isocyanato, halogen, amido, or carbamido; wherein R and $R^1$ may be optionally substituted by hydroxy, amino, lower $C_{1-6}$ alkyl, lower $C_{1-6}$ alkyl amino, alkoxy of 1-6 carbon atoms, di-lower C2-12 alkyl amino, nitro, azido, sulfhydryl, cyano, isocyanato, halogen, amido, or carbamido; x and y are the same or different and are 0, 1, 2, 3 or 4.

20. The method of claim 13 or claim 19 where one or both of R and $R^1$ is cyclopropyl, cyclopentyl, cyclohexyl, cyclohexenyl, cycloheptyl, 1,4-methylenecyclohexyl, 1-adamantyl, 2-adamantyl, exo 2-norbornyl, endo 2-norbornyl, exo 2-isobornyl, endo 2-isobornyl, menthyl, cyclopentyl-methyl, cyclohexylmethyl, 1-cyclohexylethyl, 2-cyclohexylethyl, 1-cyclohexylpropyl, 2-cyclohexylpropyl, or 3-cyclohexylpropyl.

21. The method of claim 13 or claim 19 where one or both of R and $R^1$ is heterocyclic having 6 to 18 carbon atoms and containing 1-3 separate or fused rings, and 0-5 O, N and/or S ring atoms in an aryl, alicyclic or mixed ring system.

22. The method of claim 21 where said heterocyclic aryl, alicyclic or mixed ring system is phenyl, benzyl, 1-phenylethyl, 2-phenylethyl, 1-phenylpropyl, 2-phenylpropyl, 3-phenylpropyl, o-tolyl, m-tolyl, p-tolyl, m,m'-dimethylphenyl, o-ethylphenyl, m-ethylphenyl, p-ethylphenyl, m,m'-diethylphenyl, m-methyl-m'-ethylphenyl, o-propylphenyl, 1-naphthyl, 2-naphthyl, biphenyl, indanyl, indenyl, 3-acenaphthyl, 5-acenaphthyl, 3-acenaphthylene, 5-acenaphthylene, indolyl, benzthiazole, quinolinyl, isoquinolinyl, pyridyl, pyrimidinyl, pyrazinyl, furanyl, thienyl, pyrrolyl, thiazolyl, oxazolyl, coumarinyl or imidazolyl.

23. The method of claim 13 or claim 19 wherein the compound is N,N',N'',N'''-tetra-cyclohexylhydrazinedicarboximidamide; N,N',N''N'''-tetraphenylhydrazinedicarboximidamide; N,N'-di-(adamantan-1-yl)-N'',N'''-dicyclohexylhydrazinedicarboximidamide; N,N'-di-(adamantan-2-yl)-N'',N'''-dicyclohexylhydrazinedicarboximidamide; N,N',N'',N'''-tetra-(adamantan-1-yl)-hydrazinedicarboximidamide; N,N',N'',N'''-tetra-(adamantan-2-yl)-hydrazinedicarbox-imidamide; N,N'-di-(adamantan-1-yl)-N'',N'''-di-(adamantan-2-yl)hydrazinedicarboximidamide; N,N'-di-(2-norbornyl)-N'',N'''-dicyclohexylhydrazinedicarboximidamide; N,N'-di-(2-isobornyl)-N'',N'''dicyclohexylhydrazinedicarboximidamide; N,N'-di -(2-isobornyl)-N'',N'''-di -(adamantan-1-yl)hydrazinedicarboximidamide; or N,N'-di-(2-isobornyl)-N'',N'''-di-(adamantan-2-yl)hydrazinedicarboximidamide.

24. The method of claims 12 or 13, wherein said disorder is a neurodegenerative disease selected from the group consisting of Huntington's disease, Amyotrophic Lateral Sclerosis, Alzheimer's disease, Down's Syndrome, Korsakoff's disease, olivopontocerebellar atrophy, HIV-induced dementia, HIV-induced blindness, or multi-infarct dementia.

25. The method of claims 12 or 13, wherein said disorder is nausea which may result from chemotherapy, epilepsy, convulsions, carbon monoxide poisoning, cyanide poisoning, toxic brain damage caused by tetrodotoxin or shell fish toxins, amnesia, migraine or river blindness.

26. The method of claim 15, wherein said disorder is a neurodegenerative disease selected from the group consisting of Huntington's disease, Amyotrophic Lateral Sclerosis, Alzheimer's disease, Down's Syndrome, Korsakoff's disease, olivopontocerebellar atrophy, HIV-induced dementia, HIV-induced blindness, or multi-infarct dementia.

27. The method of claim 16, wherein said disorder is a neurodegenerative disease selected from the group consisting of Huntington's disease, Amyotrophic Lateral Sclerosis, Alzheimer's disease, Down's Syndrome, Korsakoff's disease, olivopontocerebellar atrophy, HIV-induced dementia, HIV-induced blindness, or multi-infarct dementia.

28. The method of claim 20, wherein said disorder is a neurodegenerative disease selected from the group consisting of Huntington's disease, Amyotrophic Lateral Sclerosis, Alzheimer's disease, Down's Syndrome, Korsakoff's disease, olivopontocerebellar atrophy, HIV-induced dementia, HIV-induced blindness, or multi-infarct dementia.

29. The method of claim 21, wherein said disorder is a neurodegenerative disease selected from the group consisting of Huntington's disease, Amyotrophic Lateral Sclerosis, Alzheimer's disease, Down's Syndrome, Korsakoff's disease, olivopontocerebellar atrophy, HIV-induced dementia, HIV-induced blindness, or multi-infarct dementia.

30. The method of claim 23, wherein said disorder is a neurodegenerative disease selected from the group consisting of Huntington's disease, Amyotrophic Lateral Sclerosis, Alzheimer's disease, Down's Syndrome, Korsakoff's disease, olivopontocerebellar atrophy, HIV-induced dementia, HIV-induced blindness, or multi-infarct dementia.

31. The method of claim 18, wherein said disorder is a neurodegenerative disease selected from the group consisting of Huntington's disease, Amyotrophic Lateral Sclerosis, Alzheimer's disease, Down's Syndrome, Korsakoff's disease, olivopontocerebellar atrophy, HIV-induced dementia, HIV-induced blindness, or multi-infarct dementia.

32. The method of claim 15, wherein said disorder is nausea which may result from chemotherapy, epilepsy, convulsions, carbon monoxide poisoning, cyanide poisoning, toxic brain damage caused by tetrodotoxin or shell fish toxins, amnesia, migraine or river blindness.

33. The method of claim 16, wherein said disorder is nausea which may result from chemotherapy, epilepsy, convulsions, carbon monoxide poisoning, cyanide poisoning, toxic brain damage caused by tetrodotoxin or shell fish toxins, amnesia, migraine or river blindness.

34. The method of claim 20, wherein said disorder is nausea which may result from chemotherapy, epilepsy, convulsions, carbon monoxide poisoning, cyanide poisoning, toxic brain damage caused by tetrodotoxin or shell fish toxins, amnesia, migraine or river blindness.

35. The method of claim 21, wherein said disorder is nausea which may result from chemotherapy, epilepsy, convulsions, carbon monoxide poisoning, cyanide poisoning, toxic brain damage caused by tetrodotoxin or shell fish toxins, amnesia, migraine or river blindness.

36. The method of claim 23, wherein said disorder is nausea which may result from chemotherapy, epilepsy, convulsions, carbon monoxide poisoning, cyanide poisoning, toxic brain damage caused by tetrodotoxin or shell fish toxins, amnesia, migraine or river blindness.

37. The method of claim 18, wherein said disorder is nausea which may result from chemotherapy, epilepsy, convulsions, carbon monoxide poisoning, cyanide poisoning, toxic brain damage caused by tetrodotoxin or shell fish toxins, amnesia, migraine or river blindness.

* * * * *